US005866779A

United States Patent [19]
Sun et al.

[11] Patent Number: 5,866,779
[45] Date of Patent: Feb. 2, 1999

[54] RECOMBINANT GIBBERELLIN DNA AND USES THEREOF

[75] Inventors: Tai-Ping Sun, Durham, N.C.; Howard M. Goodman, Newton Centre; Frederick M. Ausubel, Newton, both of Mass.

[73] Assignee: The General Hospital Corporation, Boston, Mass.

[21] Appl. No.: 326,286

[22] Filed: Oct. 20, 1994

Related U.S. Application Data

[63] Continuation-in-part of Ser. No. 261,769, Jun. 17, 1994, abandoned, which is a continuation-in-part of Ser. No. 8,996, Jan. 27, 1993, abandoned, which is a continuation-in-part of Ser. No. 844,300, Feb. 18, 1992, abandoned.

[51] Int. Cl.$^6$ .............................. A01H 5/00; A01H 5/10; C12N 15/29; C12N 15/82; C12N 5/04
[52] U.S. Cl. .................. 800/205; 800/255; 800/DIG. 15; 536/23.2; 536/23.6; 536/24.5; 435/69.1; 435/172.3; 435/252.3; 435/254.2; 435/320.1; 435/419
[58] Field of Search .................................. 536/23.2, 23.6, 536/24.1, 24.5; 435/69.1, 70.1, 172.3, 240.4, 320.1, 252.3, 254.2, 419; 800/205, 255, DIG. 15

[56] References Cited

U.S. PATENT DOCUMENTS 4,897,345   1/1990   Harris et al. .................................. 435/7

FOREIGN PATENT DOCUMENTS

WO 93/16096   8/1993   WIPO .

OTHER PUBLICATIONS

Sun, T.–P. and Y. Kamiya, "The Arabidopsis GA1 Locus Encodes the Cyclase ent–Kaurene Synthetase A of Gibberellin Biosynthesis," *Pl. Cell* 6: 1509–1518 (Oct. 1994).
Barendse, G.W.M., et al., "Biosynthesis of the Gibberellin Precursor ENT–Kaurene in Cell–Free Enzyme Preparations from Gibberellin–Sensitive Arabidopsis Mutants," *Arabidopis Inf. Service Newsletter* 19:25–28 (1982).
Barendse, G.W.M., et al., "The role of endogenous gibberellins during fruit and seed development: Studies on gibberellin–deficient genotypes of *Arabidopsis thaliana*," *Physiol. Plant.* 67:315–319 (1986).
Bevan, M., "Binary Agrobacterium vectors for plant transformation," *Nucl. Acids Res.* 12:8711–8721 (1984).
Cornelissen, M., "Nuclear and cytoplasmic sites for the anti–sense control," *Nucl. Acids. Res.* 17(18):7203–7209 (1989).
Duncan, J.D., et al., "Properties of Kaurene Synthetase from *Marah macrocarpus* Endosperm: Evidence for the Participation of Separate but Interacting Enzymes," *Plant Physiol.* 68:1128–1134 (1981).
Giraudat, J., et al., "Isolation of the Arabidopsis AB13 gene by positional cloning," *Plant Cell* 4:1251–1261 (Oct. 1992).
Graebe, J.E., et al., "Gibberellin Biosynthesis and Control," *Ann. Rev. Plant Physiol.* 38:419–465 (1987).

Hauge, B.M., et al., "An integrated genetic/RFLP map of the *Arabidopsis thaliana* genome," *Plant J.* 3:745–754 (1993).
Hiatt, A., et al., "Monoclonal antibody engineering in plants," *FEBS Letts.* 307(1):71–75 (Jul. 1992).
Jennings, S.M., et al., "Molecular cloning and characterization of the yeast gene for squalene synthetase," *Proc. Natl. Acad. Sci. USA* 88:6038–6042 (Jul. 1991).
Koornneef, M., et al., "EMS– and radiation–induced mutation frequencies at individual loci in *Arabidopsis thaliana* (L.) Heynh," *Mutation Res.* 93:109–123 (1982).
Koornneef, M., et al., "Genetic fine–structure of the GA–1 locus in the higher plant *Arabidopsis thaliana* (L.) Heynh," *Genet. Res. Camb.* 41:57–68 (1983).
Koornneef, M., et al., "Induction and Analysis of Gibberellin Sensitive Mutants in *Arabidopsis thaliana* (L.) Heynh," *Theor. Appl. Genet.* 58:257–263 (1980).
Moore, T.C., and Moore, J.A., "Induction of ent–kaurene biosynthesis by low temperature in dwarf peas," *J. Plant Growth Regul.* 10:91–95 (Spring 1991).
Ochs, D., et al., "Cloning, expression, and sequencing of squalene–hopene cyclase, a key enzyme in triterpenoid metabolism," *J. Bacteriol.* 174:298–302 (Jan. 1992).
Railton, I.D., et al., "ent–Kaurene synthesis in chloroplasts from higher plants," *Phytochemistry* 23:1261–1267 (1984).
Saito, T., et al., "Effects of deoxygibberellin–c (dgc) and 16–deoxo–dgc on gibberellin 3–beta–hydroxylase and plant growth," *Plant & Cell Physiol.* 32:239–245 (Mar. 1991).
Schindler, U., et al., "Photoregulated gene expression may involve ubiquitous DNA binding proteins," *EMBO J.* 9(11):3415–3427 (1990).
Silver, P.H. et al., "Amino terminus of the yeast GAL4 gene product is sufficient for nuclear localization," *Proc. Natl. Acad. Sci. USA* 81:5951–5955 (1984).
Straus, D. et al., "Genomic subtraction for cloning DNA corresponding to deletion mutations," *Proc. Natl. Acad. Sci. USA* 87:1889–1893 (1990).
Sun, T., et al., abstract of "Cloning the Arabidopsis GA1 Locus by Genomic Substraction," presented at Cold Spring Harbor, New York, Oct. 2–6, 1991.
Sun, T. et al., "Cloning the Arabidopsis GA1 Locus by Genomic Subtraction," *Plant Cell* 4:119–128 (Feb. 1992).
Sun, T. et al., "Molecular biology of Signal Transduction in Plants," Abstract presented at meeting No. 1 at The Pennsylvania State University, University Park, PA (Jul., 1991) and at meeting No. 2., Cold Spring Harbor Laboratory, Cold Spring Harbor, New York (Nov., 1991).
Bensen et al. 1995. Plant Cell 7:75–84.
Ait–Ali et al. 1997. Plant Journal 11(3):443–454.
Kim et al. 1994. Plant Mol. Biol. 24:105–117.
Chang et al. 1985. Mol. Cell. Biol. 5(9):2341–2348.
Sheehy et al. 1988. Proc. Natl. Acad. Sci. USA 85(23):8805–8809.
Smith et al. 1988. Nature 334:724–726.

*Primary Examiner*—David T. Fox
*Attorney, Agent, or Firm*—Sterne, Kessler, Goldstein & Fox P.L.L.C.

[57] ABSTRACT

The present invention concerns the cloning and sequencing of DNA corresponding to the GA1 locus of *A. thaliana* which encodes ent-kaurene synthetase, to vectors containing said DNA, to vectors capable of expressing said DNA, and to hosts transformed with said vectors. The invention further concerns the use of the GA1 gene, and regulatory regions thereof, in the generation of chimeric and transgenic plants.

35 Claims, 20 Drawing Sheets

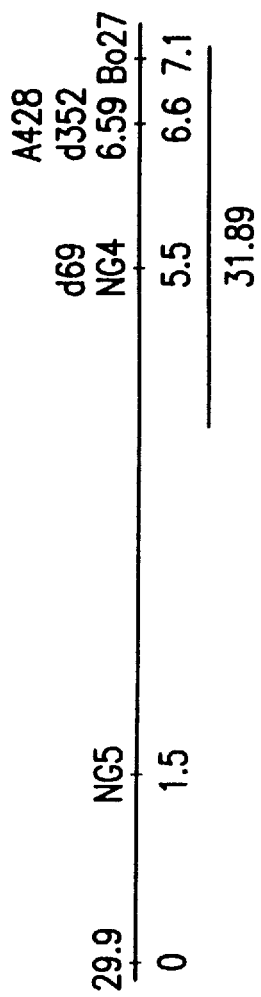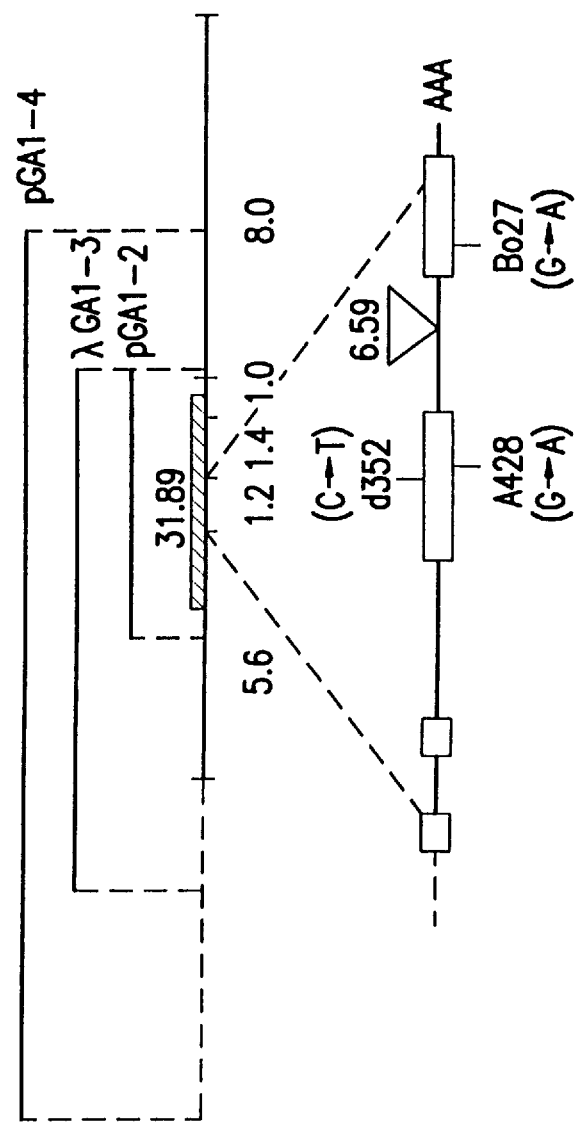
FIG.2A
FIG.2B

```
  1  CTGCAGGAAT TCCTTTTTTT TTTTTTTTT  TGGCTTTGAG TGAAGTACAT
 51  AGGACCCATC TATATATACT TGAAATATA  TTCATATAAA AATAGAATGT
101  TCAAATGTAT ATTTTTTGGC CCAACACACA AACCTTGTAA GCTTTAGCTC
151  TTTCTTGGCG TATATATCTT TTAAGACCGG AGAATCGTAC GGTACATCAA
201  TGTTTATTCC TCGAGCTATC TCAAGCAACG ATGGGAATGC TACTTCGAAT
251  CCGATTGGCA TATGCTCATC ATTTCGTCT  TGTTGCATTG AGATTCCATG
301  CCGGAAAAAC GTGATTCCTT GCAAGGGTAT TGATGAGACG ATCATGATAA
351  ATCTTAGAGC AACGACGCAT CCAAGAACCA TCGGAAAGTT GGTTCTCGGC
401  GAGAAGAGAT ACGGCGGAGG GAAACGCCGG AGTTTTATCT CCGGCATCGA
451  GATCCATTTC ACGGCATCTCC TCGTAAGCCG ATATCGTAAT TTCCCCGTCC
501  TCAATGCAAC CCAAGCTGTA TCGTAAGCCG ATATCGTAAT TTCCCCGTCC
551  GTTAGGTTTC TCAAGATCGT TTTCACACTC TTCACTGCTT CTTTGAATGC
601  ATTACTATTA CTTCCAACAC TAATCTGAGG AGCATCTTCT CCTTGAAGCT
```

FIG. 6A

```
651  GTTGCCACTC ATGTATTAGA GGCAAATCAT GTTGAACCTC TTGAGAATTA
701  ATGTATTCTT GAGTTCGAAG CTTTGAACAA TGTATGGAAC CGCTTCTGGA
751  TTTGTCTCTA GCGACATTGA GAGGAGATCC TGAGATGGTA AGGAAAGAAG
801  AAGATATTGT TGTTTTAGTA GAACTGAGAA AGGTTGTACT TGGAATGGAG
851  TTTAGAACAT GATACTGAAG AGACATGGCT TTAAAAAAAA AAAAAGGAA
901  TTC
```

FIG. 6B

```
  1 GAATTCCTTT TTTTTTTTT TAAAGCCATG TCTCTTCAGT ATCATGTTCT
 51 AAACTCCATT CCAAGTACAA CCTTTCTCAG TTCTACTAAA ACAACAATAT
101 CTTCTTCTTT CCTTACCATC TCAGGATCTC CTCTCAATGT CGCTAGAGAC
151 AAATCCAGAA GCGGTTCCAT ACATTGTTCA AAGCTTCGAA CTCAAGAATA
201 CATTAATTCT CAAGAGGTTC AACATGATTT GCCTCTAATA CATGAGTGGC
251 AACAGCTTCA AGGAGAAGAT GCTCCCTCAGA TTAGTGTTGG AAGTAATAGT
301 AATGCATTCA AAGAAGCAGT GAAGAGTGTG GAAGAGATCT TGAGAAACCT
351 AACGGACGGG GAAATTACGA TATCGGCTTA CGATACAGCT TGGGTTGCAT
401 TGATCGATGC CGGAGATAAA ACTCCGGCGT TTCCCTCCGC CGTGAAATGG
451 ATCGCCGAGA ACCAACTTTC CGATGGTTCT TGGGGAGATG CGTATCTCTT
501 CTCTTATCAT GATCGTCTCA TCAATACCCT TGCATGCGTC GTTGCTCTAA
551 GATCATGGAA TCTCTTTCCT CATCAATGCA ACAAAGGAAT CACGTTTTC
601 CGGGAAAATA TTGGGAAGCT AGAAGACGAA AATGATGAGC ATATGCCAAT
```

FIG. 7A

651 CGGATTCGAA GTAGCATTCC CATCGTTGCT TGAGATAGCT CGAGGAATAA

701 ACATTGATGT ACCGTACGAT TCTCCGGTCT TAAAAGATAT ATACGCCAAG

751 AAAGAGCTAA AGCTTACAAG GTTTGTGTGT TGGGCCAAAA AATATACATT

801 TGAACATTCT ATTTTTATAT GAATATATTT CAAAGTATAT ATAGATGGGT

851 CCTATGTACT TCACTCAAAG CCAAAAAAAA AAAAAAAAAA GGAATTCCTG

901 CAG

FIG. 7B

1   MSLQYHVLNSIPSTTFLSSTKTTISSSFLTISGSPLNVARDKSRSGS   47

48  IHCSKLRTQEYINSQEVQHDLPLIHEWQQLQGEDAPQISVGSNSNAFK  95

96  EAVKSVKTILRNLTDGEITISAYDTAWVALIDAGDKTPAFPSAVKW    141

142 IAENQLSDGSWGDAYLFSYHDRLINTLACVVALRSWNLFPHQCNKGITFF 191

192 RENIGKLEDENDEHMPIGFEVAFPSLLEIARGINIDVPYDSPVLKDIYA  240

241 KKELKLTRIPKEIMHKIPTTLLHSLEGMRDLDWEKLLKLQSQDGSFLFSP 290

291 SSTAFAFMQTRDSNCLEYLRNAVKRFNGGVPNVFPVDLFEHIWIVDRLQR 340

341 LGISRYFEEEIKECLDYVHRYWTDNGICWARCSHVQDIDDTAMAFRLLRQ 390

391 HGYQVSADVFKNFEKEGEFFCFVGQSNQAVTGMFNLYRASQLAFPREEIL 440

441 KNAKEFSYNYLLEKREREELIDKWIIMKDLPGEIGFALEIPWYASLPRVE 490

491 TRFYIDQYGGENDVWIGKTLYRMPYVNNNGYLELAKQDYNNCQAQHQLEW 540

541 DIFQKWYEENRLSEWGVRRSELLECYYLAAATIFESERSHERMVWAKSSV 590

591 LVKAISSSFGESSDSRRSFSDQFHEYIANARRSDHHFNDRNMRLDRPGS  639

640 VQASRLAGVLIGTLNQMSFDLFMSHGRDVNNLLYLSWGDWME        681

682 KWKLYGDEGEGELMVKMIILMKNNDLTNFFT                   712

713 HTHFVRLAEIINRICLPRQYLKARRNDEKEKTIKSMEKEMGKMVELALS  761

762 ESDTFRDVSITFLDVAKAFYYFALCGDHLQTHISKVLFQKV         802

FIG.8

-47         CTTCTTCACTAAATACTTAGACAGAGAAAACAGAGCTTTTTAAAGCC

1 ATGTCTCTTCAGTATCATGTTCTAAACTCCATTCCAAGTACAACCTTTCTCAGTTCTACT
    M  S  L  Q  Y  H  V  L  N  S  I  P  S  T  T  F  L  S  S  T
                                                ▽
 61 AAAACAACAATATCTTCTTCTTTCCTTACCATCTCAGGATCTCCTCTCAATGTCGCTAGA
    K  T  T  I  S  S  S  F  L  T  I  S  G  S  P  L  N  V  A  R
                                             ▽
121 GACAAATCCAGAAGCGGTTCCATACATTGTTCAAAGCTTCGAACTCAAGAATACATTAAT
    D  K  S  R  S  G  S  I  H  C  S  K  L  R  T  Q  E  Y  I  N

181 TCTCAAGAGGTTCAACATGATTTGCCTCTAATACATGAGTGGCAACAGCTTCAAGGAGAA
    S  Q  E  V  Q  H  D  L  P  L  I  H  E  W  Q  Q  L  Q  G  E
              ▽
241 GATGCTCCTCAGATTAGTGTTGGAAGTAATAGTAATGCATTCAAAGAAGCAGTGAAGAGT
    D  A  P  Q  I  S  V  G  S  N  S  N  A  F  K  E  A  V  K  S

301 GTGAAAACGATCTTGAGAAACCTAACGGACGGGGAAATTACGATATCGGCTTACGATACA
    V  K  T  I  L  R  N  L  T  D  G  E  I  T  I  S  A  Y  D  T

361 GCTTGGGTTGCATTGATCGATGCCGGAGATAAAACTCCGGCGTTTCCCTCCGCCGTGAAA
    A  W  V  A  L  I  D  A  G  D  K  T  P  A  F  P  S  A  V  K
                                (gal-6)T    A(gal-8)
421 TGGATCGCCGAGAACCAACTTTCCGATGGTTCTTGGGGAGATGCGTATCTCTTCTCTTAT
    W  I  A  E  N  Q  L  S  D  G  S  W  G  D  A  Y  L  F  S  Y 481 CATGATCGTCTCATCAATACCCTTGCATGCGTCGTTGCTCTAAGATCATGGAATCTCTTT
    H  D  R  L  I  N  T  L  A  C  V  V  A  L  R  S  W  N  L  F
                             ▽
541 CCTCATCAATGCAACAAAGGAATCACGTTTTTCCGGGAAAATATTGGGAAGCTAGAAGAC
    P  H  Q  C  N  K  G  I  T  F  F  R  E  N  I  G  K  L  E  D
                                A(gal-7)
601 GAAAATGATGAGCATATGCCAATCGGATTCGAAGTAGCATTCCCATCGTTGCTTGAGATA
    E  N  D  E  H  M  P  I  G  F  E  V  A  F  P  S  L  L  E  I 661 GCTCGAGGAATAAACATTGATGTACCGTACGATTCTCCGGTCTTAAAAGATATATACGCC
    A  R  G  I  N  I  D  V  P  Y  D  S  P  V  L  K  D  I  Y  A
                            ▽
721 AAGAAAGAGCTAAAGCTTACAAGGATACCAAAAGAGATAATGCACAAGATACCAACAACA
    K  K  E  L  K  L  T  R  I  P  K  E  I  M  H  K  I  P  T-T
                                    A(gal-9)
781 TTGTTGCATAGTTTGGAGGGGATGCGTGATTTAGATTGGGAAAAGCTCTTGAAACTTCAA
    L  L  H  S  L  E  G  M  R  D  L  D  W  E  K  L  L  K  L  Q

FIG.9A

```
 841 TCTCAAGACGGATCTTTCCTCTTCTCTCCTTCCTCTACCGCTTTTGCATTCATGCAGACC
      S  Q  D  G  S  F  L  F  S  P  S  S  T  A  F  A  F  M  Q  T

901 CGAGACAGTAACTGCCTCGAGTATTTGCGAAATGCCGTCAAACGTTTCAATGGAGGAGTT
      R  D  S  N  C  L  E  Y  L  R  N  A  V  K  R  F  N  G  G  V

961 CCCAATGTCTTTCCCGTGGATCTTTTCGAGCACATATGGATAGTGGATCGGTTACAACGT
      P  N  V  F  P  V  D  L  F  E  H  I  W  I  V  D  R  L  Q  R

1021 TTAGGGATATCGAGATACTTTGAAGAAGAGATTAAAGAGTGTCTTGACTATGTCCACAGA
      L  G  I  S  R  Y  F  E  E  E  I  K  E  C  L  D  Y  V  H  R

1081 TATTGGACCGACAATGGCATATGTTGGGCTAGATGTTCCCATGTCCAAGACATCGATGAT
      Y  W  T  D  N  G  I  C  W  A  R  C  S  H  V  Q  D  I  D  D

1141 ACAGCCATGGCATTTAGGCTCTTAAGACAACATGGATACCAAGTGTCCGCAGATGTATTC
      T  A  M  A  F  R  L  L  R  Q  H  G  Y  Q  V  S  A  D  V  F

1201 AAGAACTTTGAGAAAGAGGGAGAGTTTTTCTGCTTTGTGGGGCAATCAAACCAAGCAGTA
      K  N  F  E  K  E  G  E  F  F  C  F  V  G  Q  S  N  Q  A  V

1261 ACCGGTATGTTCAACCTATACCGGGCATCACAATTGGCGTTTCCAAGGGAAGAGATATTG
      T  G  M  F  N  L  Y  R  A  S  Q  L  A  F  P  R  E  E  I  L

1321 AAAAACGCCAAAGAGTTTTCTTATAATTATCTGCTAGAAAAACGGGAGAGAGAGGAGTTG
      K  N  A  K  E  F  S  Y  N  Y  L  L  E  K  R  E  R  E  E  L

1381 ATTGATAAGTGGATTATAATGAAAGACTTACCTGGCGAGATTGGGTTTGCGTTAGAGATT
      I  D  K  W  I  I  M  K  D  L  P  G  E  I  G  F  A  L  E  I

1441 CCATGGTACGCAAGCTTGCCTCGAGTAGAGACGAGATTCTATATTGATCAATATGGTGGA
      P  W  Y  A  S  L  P  R  V  E  T  R  F  Y  I  D  Q  Y  G  G

1501 GAAAACGACGTTTGGATTGGCAAGACTCTTTATAGGATGCCATACGTGAACAATAATGGA
      E  N  D  V  W  I  G  K  T  L  Y  R  M  P  Y  V  N  N  G

1561 TATCTGGAATTAGCAAAACAAGATTACAACAATTGCCAAGCTCAGCATCAGCTCGAATGG
      Y  L  E  L  A  K  Q  D  Y  N  N  C  Q  A  Q  H  Q  L  E  W

1621 GACATATTCCAAAAGTGGTATGAAGAAAATAGGTTAAGTGAGTGGGGTGTGCCGCAGAAGT
      D  I  F  Q  K  W  Y  E  E  N  R  L  S  E  W  G  V  R  R  S

1681 GAGCTTCTCGAGTGTTACTACTTAGCCGGCTGCAACTATATTTGAATCAGAAAGGTCACAT
      E  L  L  E  C  Y  Y  L  A  A  A  T  I  F  E  S  E  R  S  H
```

FIG.9B

```
1741 GAGAGAATGGTTTGGGCTAAGTCAAGTGTATTGGTTAAAGCCATTTCTTCTTCTTTTGGG
      E  R  M  V  W  A  K  S  S  V  L  V  K  A  I  S  S  S  F  G

1801 GAATCCTCTGACTCCAGAAGAAGCTTCTCCGATCAGTTTCATGAATACATTGCCAATGCT
      E  S  S  D  S  R  R  S  F  S  D  Q  F  H  E  Y  I  A  N  A
                                        ▽
1861 CGACGAAGTGATCATCACTTTAATGACAGGAACATGAGATTGGACCGACCAGGATCGGTT
      R  R  S  D  H  H  F  N  D  R  N  M  R  L  D  R  P  G  S  V

1921 CAGGCCAGTCGGCTTGCCGGAGTGTTAATCGGGACTTTGAATCAAATGTCTTTTGACCTT
      Q  A  S  R  L  A  G  V  L  I  G  T  L  N  Q  M  S  F  D  L
                                  ▽
1981 TTCATGTCTCATGGCCGTGACGTTAACAATCTCCTCTATCTATCGTGGGGAGATTGGATG
      F  M  S  H  G  R  D  V  N  N  L  L  Y  L  S  W  G  D  W  M

2041 GAAAAATGGAAACTATATGGAGATGAAGGAGAAGGAGAGCTCATGGTGAAGATGATAATT
      E  K  W  K  L  Y  G  D  E  G  E  G  E  L  M  V  K  M  I  I

2101 CTAATGAAGAACAATGACCTAACTAACTTCTTCACCCACACTCACTTCGTTCGTCTCGCG
      L  M  K  N  N  D  L  T  N  F  F  T  H  T  H  F  V  R  L  A
                                                ▽
2161 GAAATCATCAATCGAATCTGTCTTCCTCGCCAATACTTAAAGGCAAGGAGAAACGATGAG
      E  I  I  N  R  I  C  L  P  R  Q  Y  L  K  A  R  R  N  D  E

2221 AAGGAGAAGACAATAAAGAGTATGGAGAAGGAGATGGGGAAAATGGTTGAGTTAGCATTG
      K  E  K  T  I  K  S  M  E  K  E  M  G  K  M  V  E  L  A  L

2281 TCGGAGAGTGACACATTTCGTGACGTCAGCATCACGTTTCTTGATGTAGCAAAAGCATTT
      S  E  S  D  T  F  R  D  V  S  I  T  F  L  D  V  A  K  A  F
                                         ◄── gal-4 ──►
2341 TACTACTTTGCTTTATGTGGCGATCATCTCCAAACTCACATCTCCAAAGTCTTGTTTCAA
      Y  Y  F  A  L  C  G  D  H  L  Q  T  H  I  S  K  V  L  F  Q 2401 AAAGTCTAGTAACCTCATCATCATCATCGATCCATTAACAATCAGTGGATCGATGTATCC
      K  V  *  *

2461 ATAGATGCGTGAATAATATTTCATGTAGAGAAGGAGAACAAATTAGATCATGTAGGGTTA

2521 TCAAAAAAAAAAAAAAAAAA
```

FIG.9C

```
tobsqpc     8   KLADTLNLID IIERLGISYH FEKEIDEILD QI..YNQN.. .SN.....CN
cosbene   112   DSVETVILID LLCRLGVSYH FENDIEELLS KI..FNSQ.. .PDLVDEKEC
limonene  105   DQIRQLELID DLQRMGLSDH FQNEFKEILS SI..YLDHHY YKNPFPKEER
gal       327   DLFEHIWIVD RLQRLGISRY FEEEIKECLD YVHRYWTDNG ICWARCSHVQ
consensus       dl.e.....D .IqRlGiS.. Fe.eikE.Ld ....y..... ..........

tobsqpc    48   DLCTSALQFR LLRQHGFNIS PEIFSKFQDE NG..KFKESL ASDVLGLLNL
cosbene   157   DLYTAAIVFR VFRQHGFKMS SDVFSKFKDS DG..KFKESL RGDAKGMLSL
limonene  153   DLYSTSLAFR LLREHGFQVA QEVFDSFKNE EG..EFKESL SDDTRGLLQL
gal       377   DIDDTAMAFR LLRQHGYQVS ADVFKNFEKE GEFFCFVGQS NQAVTGMFNL
consensus       D...to.oFR llRqHG.qvs .dvF..F..e .....F.... ...v.Gm.nL tobsqpc    96   YEASHVRTHA DDILEDALAF STIHL..... .ESAAPH..L KSPLREQVTH
cosbene   205   FEASHLSVHG EDILEEAFAF TKDYL..... .QSSAVE..L FPNLKRHITN
limonene  201   YEASFLLTEG ETTLESAREF ATKFL..... .EEKVNEGGV DGDLLTRIAY
gal       427   YRASQLAFPR EEILKNAKEF SYNYLLEKRE REELIDKWII MKDLPGEIGF
consensus       y.AS.l.... e.iL..A.eF s..yL..... .ee....... ..dL...i..

tobsqpc   138   ALEQCLHKGV PRVETRFFIS SIYDKEQSK. .......... .NNVLLRFAK
cosbene   247   ALEQPFHSGV PRLEARKFID LYEADIECR. .......... .NETLLEFAK
limonene  245   SLDIPLHWRI KRPNAPVWIE WYRKRPD.M. .......... .NPVVLELAI
gal       477   ALEIPWYASL PRVETRFYID QYGGENDVWI GKTLYRMPYV NNNGYLELAK
consensus       oLeip..... pRvetrf.Id .y....d... .......... .Nn..LelAk tobsqpc   176   LDFNLLQMLH KQELAQVSRW WKDLDFVTTL PYARDRVVEC YFWALGVYFE
cosbene   285   LDYNRVQLLH QQELCQFSKW WKDLNLASDI PYARDRMAEI FFWAVAMYFE
limonene  282   LDLNIVQAQF QEELKESFRW WRNTGFVEKL PFARDRLVEC YFWNTGIIEP
gal       527   QDYNNCQAQH QLEWDIFQKW YEENRL.SEW GVRRSELLEC YYLAAATIFE
consensus       .DyN..Qoqh q.E...f.kW .....l.s.. ...R..l.Ec y..o.o.ife tobsqpc   226   PQYSQARVML VKTISMISIV DDTFDAYGT
cosbene   335   PDYAHTRMII AKVVLLISLI DDTIDAYAT
limonene  332   RQHASARIMM GKVNALITVI DDIYDVYGT
gal       576   SERSHERMVW AKSSVLVKAI SSSFGESSD
consensus       ...sh.Rm.. oK...l...i ...f.....
```

FIG.15

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 903 base pairs
        ( B ) TYPE: nucleic acid
        ( C ) STRANDEDNESS: single
        ( D ) TOPOLOGY: linear ( i i ) MOLECULE TYPE: cDNA to mRNA ( v i ) ORIGINAL SOURCE:

(A) ORGANISM: Arabidopsis thaliana (x i) SEQUENCE DESCRIPTION: SEQ ID NO:1:

| | | | | | |
|---|---|---|---|---|---|
| CTGCAGGAAT | TCCTTTTTTT | TTTTTTTTT | TGGCTTTGAG | TGAAGTACAT | AGGACCCATC | 60 |
| TATATATACT | TTGAAATATA | TTCATATAAA | AATAGAATGT | TCAAATGTAT | ATTTTTTGGC | 120 |
| CCAACACACA | AACCTTGTAA | GCTTTAGCTC | TTTCTTGGCG | TATATATCTT | TTAAGACCGG | 180 |
| AGAATCGTAC | GGTACATCAA | TGTTTATTCC | TCGAGCTATC | TCAAGCAACG | ATGGGAATGC | 240 |
| TACTTCGAAT | CCGATTGGCA | TATGCTCATC | ATTTCGTCT | TCTAGCTTCC | CAATATTTTC | 300 |
| CCGGAAAAAC | GTGATTCCTT | TGTTGCATTG | ATGAGGAAAG | AGATTCCATG | ATCTTAGAGC | 360 |
| AACGACGCAT | GCAAGGGTAT | TGATGAGACG | ATCATGATAA | GAGAAGAGAT | ACGCATCTCC | 420 |
| CCAAGAACCA | TCGGAAAGTT | GGTTCTCGGC | GATCCATTTC | ACGGCGGAGG | GAAACGCCGG | 480 |
| AGTTTTATCT | CCGGCATCGA | TCAATGCAAC | CCAAGCTGTA | TCGTAAGCCG | ATATCGTAAT | 540 |
| TTCCCCGTCC | GTTAGGTTTC | TCAAGATCGT | TTTCACACTC | TTCACTGCTT | CTTTGAATGC | 600 |
| ATTACTATTA | CTTCCAACAC | TAATCTGAGG | AGCATCTTCT | CCTTGAAGCT | GTTGCCACTC | 660 |
| ATGTATTAGA | GGCAAATCAT | GTTGAACCTC | TTGAGAATTA | ATGTATTCTT | GAGTTCGAAG | 720 |
| CTTTGAACAA | TGTATGGAAC | CGCTTCTGGA | TTTGTCTCTA | GCGACATTGA | GAGGAGATCC | 780 |
| TGAGATGGTA | AGGAAGAAG | AAGATATTGT | TGTTTAGTA | GAACTGAGAA | AGGTTGTACT | 840 |
| TGGAATGGAG | TTTAGAACAT | GATACTGAAG | AGACATGGCT | TTAAAAAAAA | AAAAAAGGAA | 900 |
| TTC | | | | | | 903 |

(2) INFORMATION FOR SEQ ID NO:2:

(i) SEQUENCE CHARACTERISTICS:
  (A) LENGTH: 903 base pairs
  (B) TYPE: nucleic acid
  (C) STRANDEDNESS: single
  (D) TOPOLOGY: linear (i i) MOLECULE TYPE: cDNA (v i) ORIGINAL SOURCE:
  (A) ORGANISM: Arabidopsis thaliana (x i) SEQUENCE DESCRIPTION: SEQ ID NO:2:

| | | | | | |
|---|---|---|---|---|---|
| GAATTCCTTT | TTTTTTTTT | TAAAGCCATG | TCTCTTCAGT | ATCATGTTCT | AAACTCCATT | 60 |
| CCAAGTACAA | CCTTTCTCAG | TTCTACTAAA | ACAACAATAT | CTTCTTCTTT | CCTTACCATC | 120 |
| TCAGGATCTC | CTCTCAATGT | CGCTAGAGAC | AAATCCAGAA | GCGGTTCCAT | ACATTGTTCA | 180 |
| AAGCTTCGAA | CTCAAGAATA | CATTAATTCT | CAAGAGGTTC | AACATGATTT | GCCTCTAATA | 240 |
| CATGAGTGGC | AACAGCTTCA | AGGAGAAGAT | GCTCCTCAGA | TTAGTGTTGG | AAGTAATAGT | 300 |
| AATGCATTCA | AAGAAGCAGT | GAAGAGTGTG | AAAACGATCT | TGAGAAACCT | AACGGACGGG | 360 |
| GAAATTACGA | TATCGGCTTA | CGATACAGCT | TGGGTTGCAT | TGATCGATGC | CGGAGATAAA | 420 |
| ACTCCGGCGT | TTCCCTCCGC | CGTGAAATGG | ATCGCCGAGA | ACCAACTTTC | CGATGGTTCT | 480 |
| TGGGGAGATG | CGTATCTCTT | CTCTTATCAT | GATCGTCTCA | TCAATACCCT | TGCATGCGTC | 540 |
| GTTGCTCTAA | GATCATGGAA | TCTCTTTCCT | CATCAATGCA | ACAAAGGAAT | CACGTTTTTC | 600 |
| CGGGAAAATA | TTGGGAAGCT | AGAAGACGAA | AATGATGAGC | ATATGCCAAT | CGGATTCGAA | 660 |
| GTAGCATTCC | CATCGTTGCT | TGAGATAGCT | CGAGGAATAA | ACATTGATGT | ACCGTACGAT | 720 |
| TCTCCGGTCT | TAAAAGATAT | ATACGCCAAG | AAAGAGCTAA | AGCTTACAAG | GTTTGTGTGT | 780 |
| TGGGCCAAAA | AATATACATT | TGAACATTCT | ATTTTTATAT | GAATATATTT | CAAAGTATAT | 840 |

| ATAGATGGGT | CCTATGTACT | TCACTCAAAG | CCAAAAAAAA | AAAAAAAAAA | GGAATTCCTG | 900 |

CAG  903

(2) INFORMATION FOR SEQ ID NO:3:

(i) SEQUENCE CHARACTERISTICS:
     (A) LENGTH: 2587 base pairs
     (B) TYPE: nucleic acid
     (C) STRANDEDNESS: single
     (D) TOPOLOGY: linear (ii) MOLECULE TYPE: cDNA (vi) ORIGINAL SOURCE:
     (A) ORGANISM: Arabidopsis thaliana (ix) FEATURE:
     (A) NAME/KEY: CDS
     (B) LOCATION: 48..2453

(xi) SEQUENCE DESCRIPTION: SEQ ID NO:3:

| CTTCTTCACT | AAATACTTAG | ACAGAGAAAA | CAGAGCTTTT | TAAAGCC | ATG Met 1 | TCT Ser | CTT Leu | 56 |

| CAG | TAT | CAT | GTT | CTA | AAC | TCC | ATT | CCA | AGT | ACA | ACC | TTT | CTC | AGT | TCT | 104 |
| Gln | Tyr 5 | His | Val | Leu | Asn | Ser 10 | Ile | Pro | Ser | Thr | Thr 15 | Phe | Leu | Ser | Ser | |

| ACT | AAA | ACA | ACA | ATA | TCT | TCT | TCT | TTC | CTT | ACC | ATC | TCA | GGA | TCT | CCT | 152 |
| Thr 20 | Lys | Thr | Thr | Ile | Ser 25 | Ser | Ser | Phe | Leu | Thr 30 | Ile | Ser | Gly | Ser | Pro 35 | |

| CTC | AAT | GTC | GCT | AGA | GAC | AAA | TCC | AGA | AGC | GGT | TCC | ATA | CAT | TGT | TCA | 200 |
| Leu | Asn | Val | Ala | Arg 40 | Asp | Lys | Ser | Arg | Ser 45 | Gly | Ser | Ile | His | Cys 50 | Ser | |

| AAG | CTT | CGA | ACT | CAA | GAA | TAC | ATT | AAT | TCT | CAA | GAG | GTT | CAA | CAT | GAT | 248 |
| Lys | Leu | Arg | Thr 55 | Gln | Glu | Tyr | Ile | Asn 60 | Ser | Gln | Glu | Val | Gln 65 | His | Asp | |

| TTG | CCT | CTA | ATA | CAT | GAG | TGG | CAA | CAG | CTT | CAA | GGA | GAA | GAT | GCT | CCT | 296 |
| Leu | Pro | Leu 70 | Ile | His | Glu | Trp | Gln 75 | Gln | Leu | Gln | Gly | Glu 80 | Asp | Ala | Pro | |

| CAG | ATT | AGT | GTT | GGA | AGT | AAT | AGT | AAT | GCA | TTC | AAA | GAA | GCA | GTG | AAG | 344 |
| Gln | Ile 85 | Ser | Val | Gly | Ser | Asn 90 | Ser | Asn | Ala | Phe | Lys 95 | Glu | Ala | Val | Lys | |

| AGT | GTG | AAA | ACG | ATC | TTG | AGA | AAC | CTA | ACG | GAC | GGG | GAA | ATT | ACG | ATA | 392 |
| Ser 100 | Val | Lys | Thr | Ile | Leu 105 | Arg | Asn | Leu | Thr | Asp 110 | Gly | Glu | Ile | Thr | Ile 115 | |

| TCG | GCT | TAC | GAT | ACA | GCT | TGG | GTT | GCA | TTG | ATC | GAT | GCC | GGA | GAT | AAA | 440 |
| Ser | Ala | Tyr | Asp | Thr 120 | Ala | Trp | Val | Ala | Leu 125 | Ile | Asp | Ala | Gly | Asp 130 | Lys | |

| ACT | CCG | GCG | TTT | CCC | TCC | GCC | GTG | AAA | TGG | ATC | GCC | GAG | AAC | CAA | CTT | 488 |
| Thr | Pro | Ala | Phe 135 | Pro | Ser | Ala | Val | Lys 140 | Trp | Ile | Ala | Glu | Asn 145 | Gln | Leu | |

| TCC | GAT | GGT | TCT | TGG | GGA | GAT | GCG | TAT | CTC | TTC | TCT | TAT | CAT | GAT | CGT | 536 |
| Ser | Asp | Gly 150 | Ser | Trp | Gly | Asp | Ala 155 | Tyr | Leu | Phe | Ser | Tyr 160 | His | Asp | Arg | |

| CTC | ATC | AAT | ACC | CTT | GCA | TGC | GTC | GTT | GCT | CTA | AGA | TCA | TGG | AAT | CTC | 584 |
| Leu | Ile 165 | Asn | Thr | Leu | Ala | Cys 170 | Val | Val | Ala | Leu | Arg 175 | Ser | Trp | Asn | Leu | |

| TTT | CCT | CAT | CAA | TGC | AAC | AAA | GGA | ATC | ACG | TTT | TTC | CGG | GAA | AAT | ATT | 632 |
| Phe | Pro | His 180 | Gln | Cys | Asn | Lys | Gly 185 | Ile | Thr | Phe | Phe | Arg 190 | Glu | Asn | Ile 195 | |

| GGG | AAG | CTA | GAA | GAC | GAA | AAT | GAT | GAG | CAT | ATG | CCA | ATC | GGA | TTC | GAA | 680 |
| Gly | Lys | Leu | Glu | Asp 200 | Glu | Asn | Asp | Glu | His 205 | Met | Pro | Ile | Gly | Phe 210 | Glu | |

```
GTA GCA TTC CCA TCG TTG CTT GAG ATA GCT CGA GGA ATA AAC ATT GAT       728
Val Ala Phe Pro Ser Leu Leu Glu Ile Ala Arg Gly Ile Asn Ile Asp
            215                 220                 225

GTA CCG TAC GAT TCT CCG GTC TTA AAA GAT ATA TAC GCC AAG AAA GAG       776
Val Pro Tyr Asp Ser Pro Val Leu Lys Asp Ile Tyr Ala Lys Lys Glu
        230                 235                 240

CTA AAG CTT ACA AGG ATA CCA AAA GAG ATA ATG CAC AAG ATA CCA ACA       824
Leu Lys Leu Thr Arg Ile Pro Lys Glu Ile Met His Lys Ile Pro Thr
    245                 250                 255

ACA TTG TTG CAT AGT TTG GAG GGG ATG CGT GAT TTA GAT TGG GAA AAG       872
Thr Leu Leu His Ser Leu Glu Gly Met Arg Asp Leu Asp Trp Glu Lys
260                 265                 270                 275

CTC TTG AAA CTT CAA TCT CAA GAC GGA TCT TTC CTC TTC TCT CCT TCC       920
Leu Leu Lys Leu Gln Ser Gln Asp Gly Ser Phe Leu Phe Ser Pro Ser
                280                 285                 290

TCT ACC GCT TTT GCA TTC ATG CAG ACC CGA GAC AGT AAC TGC CTC GAG       968
Ser Thr Ala Phe Ala Phe Met Gln Thr Arg Asp Ser Asn Cys Leu Glu
            295                 300                 305

TAT TTG CGA AAT GCC GTC AAA CGT TTC AAT GGA GGA GTT CCC AAT GTC      1016
Tyr Leu Arg Asn Ala Val Lys Arg Phe Asn Gly Gly Val Pro Asn Val
        310                 315                 320

TTT CCC GTG GAT CTT TTC GAG CAC ATA TGG ATA GTG GAT CGG TTA CAA      1064
Phe Pro Val Asp Leu Phe Glu His Ile Trp Ile Val Asp Arg Leu Gln
325                 330                 335

CGT TTA GGG ATA TCG AGA TAC TTT GAA GAA GAG ATT AAA GAG TGT CTT      1112
Arg Leu Gly Ile Ser Arg Tyr Phe Glu Glu Glu Ile Lys Glu Cys Leu
340                 345                 350                 355

GAC TAT GTC CAC AGA TAT TGG ACC GAC AAT GGC ATA TGT TGG GCT AGA      1160
Asp Tyr Val His Arg Tyr Trp Thr Asp Asn Gly Ile Cys Trp Ala Arg
            360                 365                 370

TGT TCC CAT GTC CAA GAC ATC GAT GAT ACA GCC ATG GCA TTT AGG CTC      1208
Cys Ser His Val Gln Asp Ile Asp Asp Thr Ala Met Ala Phe Arg Leu
        375                 380                 385

TTA AGA CAA CAT GGA TAC CAA GTG TCC GCA GAT GTA TTC AAG AAC TTT      1256
Leu Arg Gln His Gly Tyr Gln Val Ser Ala Asp Val Phe Lys Asn Phe
    390                 395                 400

GAG AAA GAG GGA GAG TTT TTC TGC TTT GTG GGG CAA TCA AAC CAA GCA      1304
Glu Lys Glu Gly Glu Phe Phe Cys Phe Val Gly Gln Ser Asn Gln Ala
    405                 410                 415

GTA ACC GGT ATG TTC AAC CTA TAC CGG GCA TCA CAA TTG GCG TTT CCA      1352
Val Thr Gly Met Phe Asn Leu Tyr Arg Ala Ser Gln Leu Ala Phe Pro
420                 425                 430                 435

AGG GAA GAG ATA TTG AAA AAC GCC AAA GAG TTT TCT TAT AAT TAT CTG      1400
Arg Glu Glu Ile Leu Lys Asn Ala Lys Glu Phe Ser Tyr Asn Tyr Leu
            440                 445                 450

CTA GAA AAA CGG GAG AGA GAG GAG TTG ATT GAT AAG TGG ATT ATA ATG      1448
Leu Glu Lys Arg Glu Arg Glu Glu Leu Ile Asp Lys Trp Ile Ile Met
        455                 460                 465

AAA GAC TTA CCT GGC GAG ATT GGG TTT GCG TTA GAG ATT CCA TGG TAC      1496
Lys Asp Leu Pro Gly Glu Ile Gly Phe Ala Leu Glu Ile Pro Trp Tyr
    470                 475                 480

GCA AGC TTG CCT CGA GTA GAG ACG AGA TTC TAT ATT GAT CAA TAT GGT      1544
Ala Ser Leu Pro Arg Val Glu Thr Arg Phe Tyr Ile Asp Gln Tyr Gly
    485                 490                 495

GGA GAA AAC GAC GTT TGG ATT GGC AAG ACT CTT TAT AGG ATG CCA TAC      1592
Gly Glu Asn Asp Val Trp Ile Gly Lys Thr Leu Tyr Arg Met Pro Tyr
500                 505                 510                 515

GTG AAC AAT AAT GGA TAT CTG GAA TTA GCA AAA CAA GAT TAC AAC AAT      1640
Val Asn Asn Asn Gly Tyr Leu Glu Leu Ala Lys Gln Asp Tyr Asn Asn
            520                 525                 530
```

```
TGC  CAA  GCT  CAG  CAT  CAG  CTC  GAA  TGG  GAC  ATA  TTC  CAA  AAG  TGG  TAT    1688
Cys  Gln  Ala  Gln  His  Gln  Leu  Glu  Trp  Asp  Ile  Phe  Gln  Lys  Trp  Tyr
          535                      540                      545

GAA  GAA  AAT  AGG  TTA  AGT  GAG  TGG  GGT  GTG  CGC  AGA  AGT  GAG  CTT  CTC    1736
Glu  Glu  Asn  Arg  Leu  Ser  Glu  Trp  Gly  Val  Arg  Arg  Ser  Glu  Leu  Leu
          550                      555                      560

GAG  TGT  TAC  TAC  TTA  GCG  GCT  GCA  ACT  ATA  TTT  GAA  TCA  GAA  AGG  TCA    1784
Glu  Cys  Tyr  Tyr  Leu  Ala  Ala  Ala  Thr  Ile  Phe  Glu  Ser  Glu  Arg  Ser
     565                      570                      575

CAT  GAG  AGA  ATG  GTT  TGG  GCT  AAG  TCA  AGT  GTA  TTG  GTT  AAA  GCC  ATT    1832
His  Glu  Arg  Met  Val  Trp  Ala  Lys  Ser  Ser  Val  Leu  Val  Lys  Ala  Ile
580                      585                      590                      595

TCT  TCT  TCT  TTT  GGG  GAA  TCC  TCT  GAC  TCC  AGA  AGA  AGC  TTC  TCC  GAT    1880
Ser  Ser  Ser  Phe  Gly  Glu  Ser  Ser  Asp  Ser  Arg  Arg  Ser  Phe  Ser  Asp
               600                      605                      610

CAG  TTT  CAT  GAA  TAC  ATT  GCC  AAT  GCT  CGA  CGA  AGT  GAT  CAT  CAC  TTT    1928
Gln  Phe  His  Glu  Tyr  Ile  Ala  Asn  Ala  Arg  Arg  Ser  Asp  His  His  Phe
          615                      620                      625

AAT  GAC  AGG  AAC  ATG  AGA  TTG  GAC  CGA  CCA  GGA  TCG  GTT  CAG  GCC  AGT    1976
Asn  Asp  Arg  Asn  Met  Arg  Leu  Asp  Arg  Pro  Gly  Ser  Val  Gln  Ala  Ser
          630                      635                      640

CGG  CTT  GCC  GGA  GTG  TTA  ATC  GGG  ACT  TTG  AAT  CAA  ATG  TCT  TTT  GAC    2024
Arg  Leu  Ala  Gly  Val  Leu  Ile  Gly  Thr  Leu  Asn  Gln  Met  Ser  Phe  Asp
645                      650                      655

CTT  TTC  ATG  TCT  CAT  GGC  CGT  GAC  GTT  AAC  AAT  CTC  CTC  TAT  CTA  TCG    2072
Leu  Phe  Met  Ser  His  Gly  Arg  Asp  Val  Asn  Asn  Leu  Leu  Tyr  Leu  Ser
660                      665                      670                      675

TGG  GGA  GAT  TGG  ATG  GAA  AAA  TGG  AAA  CTA  TAT  GGA  GAT  GAA  GGA  GAA    2120
Trp  Gly  Asp  Trp  Met  Glu  Lys  Trp  Lys  Leu  Tyr  Gly  Asp  Glu  Gly  Glu
               680                      685                      690

GGA  GAG  CTC  ATG  GTG  AAG  ATG  ATA  ATT  CTA  ATG  AAG  AAC  AAT  GAC  CTA    2168
Gly  Glu  Leu  Met  Val  Lys  Met  Ile  Ile  Leu  Met  Lys  Asn  Asn  Asp  Leu
          695                      700                      705

ACT  AAC  TTC  TTC  ACC  CAC  ACT  CAC  TTC  GTT  CGT  CTC  GCG  GAA  ATC  ATC    2216
Thr  Asn  Phe  Phe  Thr  His  Thr  His  Phe  Val  Arg  Leu  Ala  Glu  Ile  Ile
          710                      715                      720

AAT  CGA  ATC  TGT  CTT  CCT  CGC  CAA  TAC  TTA  AAG  GCA  AGG  AGA  AAC  GAT    2264
Asn  Arg  Ile  Cys  Leu  Pro  Arg  Gln  Tyr  Leu  Lys  Ala  Arg  Arg  Asn  Asp
     725                      730                      735

GAG  AAG  GAG  AAG  ACA  ATA  AAG  AGT  ATG  GAG  AAG  GAG  ATG  GGG  AAA  ATG    2312
Glu  Lys  Glu  Lys  Thr  Ile  Lys  Ser  Met  Glu  Lys  Glu  Met  Gly  Lys  Met
740                      745                      750                      755

GTT  GAG  TTA  GCA  TTG  TCG  GAG  AGT  GAC  ACA  TTT  CGT  GAC  GTC  AGC  ATC    2360
Val  Glu  Leu  Ala  Leu  Ser  Glu  Ser  Asp  Thr  Phe  Arg  Asp  Val  Ser  Ile
               760                      765                      770

ACG  TTT  CTT  GAT  GTA  GCA  AAA  GCA  TTT  TAC  TAC  TTT  GCT  TTA  TGT  GGC    2408
Thr  Phe  Leu  Asp  Val  Ala  Lys  Ala  Phe  Tyr  Tyr  Phe  Ala  Leu  Cys  Gly
          775                      780                      785

GAT  CAT  CTC  CAA  ACT  CAC  ATC  TCC  AAA  GTC  TTG  TTT  CAA  AAA  GTC           2453
Asp  His  Leu  Gln  Thr  His  Ile  Ser  Lys  Val  Leu  Phe  Gln  Lys  Val
          790                      795                      800

TAGTAACCTC  ATCATCATCA  TCGATCCATT  AACAATCAGT  GGATCGATGT  ATCCATAGAT             2513

GCGTGAATAA  TATTTCATGT  AGAGAAGGAG  AACAAATTAG  ATCATGTAGG  GTTATCAAAA             2573

AAAAAAAAAA  AAAA                                                                   2587
```

( 2 ) INFORMATION FOR SEQ ID NO:4:

( i ) SEQUENCE CHARACTERISTICS:
        ( A ) LENGTH: 802 amino acids
        ( B ) TYPE: amino acid ( D ) TOPOLOGY: linear ( i i ) MOLECULE TYPE: protein ( x i ) SEQUENCE DESCRIPTION: SEQ ID NO:4:

| Met | Ser | Leu | Gln | Tyr | His | Val | Leu | Asn | Ser | Ile | Pro | Ser | Thr | Thr | Phe |
|---|---|---|---|---|---|---|---|---|---|---|---|---|---|---|---|
| 1 | | | | 5 | | | | | 10 | | | | | 15 | |
| Leu | Ser | Ser | Thr | Lys | Thr | Thr | Ile | Ser | Ser | Ser | Phe | Leu | Thr | Ile | Ser |
| | | | 20 | | | | 25 | | | | | | 30 | | |
| Gly | Ser | Pro | Leu | Asn | Val | Ala | Arg | Asp | Lys | Ser | Arg | Ser | Gly | Ser | Ile |
| | | 35 | | | | | 40 | | | | | 45 | | | |
| His | Cys | Ser | Lys | Leu | Arg | Thr | Gln | Glu | Tyr | Ile | Asn | Ser | Gln | Glu | Val |
| | 50 | | | | | 55 | | | | | 60 | | | | |
| Gln | His | Asp | Leu | Pro | Leu | Ile | His | Glu | Trp | Gln | Gln | Leu | Gln | Gly | Glu |
| 65 | | | | | 70 | | | | | 75 | | | | | 80 |
| Asp | Ala | Pro | Gln | Ile | Ser | Val | Gly | Ser | Asn | Ser | Asn | Ala | Phe | Lys | Glu |
| | | | | 85 | | | | | 90 | | | | | 95 | |
| Ala | Val | Lys | Ser | Val | Lys | Thr | Ile | Leu | Arg | Asn | Leu | Thr | Asp | Gly | Glu |
| | | | 100 | | | | 105 | | | | | 110 | | | |
| Ile | Thr | Ile | Ser | Ala | Tyr | Asp | Thr | Ala | Trp | Val | Ala | Leu | Ile | Asp | Ala |
| | | 115 | | | | | 120 | | | | | 125 | | | |
| Gly | Asp | Lys | Thr | Pro | Ala | Phe | Pro | Ser | Ala | Val | Lys | Trp | Ile | Ala | Glu |
| | 130 | | | | | 135 | | | | | 140 | | | | |
| Asn | Gln | Leu | Ser | Asp | Gly | Ser | Trp | Gly | Asp | Ala | Tyr | Leu | Phe | Ser | Tyr |
| 145 | | | | | 150 | | | | | 155 | | | | | 160 |
| His | Asp | Arg | Leu | Ile | Asn | Thr | Leu | Ala | Cys | Val | Val | Ala | Leu | Arg | Ser |
| | | | | 165 | | | | | 170 | | | | | 175 | |
| Trp | Asn | Leu | Phe | Pro | His | Gln | Cys | Asn | Lys | Gly | Ile | Thr | Phe | Phe | Arg |
| | | | 180 | | | | | 185 | | | | | 190 | | |
| Glu | Asn | Ile | Gly | Lys | Leu | Glu | Asp | Glu | Asn | Asp | Glu | His | Met | Pro | Ile |
| | | 195 | | | | | 200 | | | | | 205 | | | |
| Gly | Phe | Glu | Val | Ala | Phe | Pro | Ser | Leu | Leu | Glu | Ile | Ala | Arg | Gly | Ile |
| | 210 | | | | | 215 | | | | | 220 | | | | |
| Asn | Ile | Asp | Val | Pro | Tyr | Asp | Ser | Pro | Val | Leu | Lys | Asp | Ile | Tyr | Ala |
| 225 | | | | | 230 | | | | | 235 | | | | | 240 |
| Lys | Lys | Glu | Leu | Lys | Leu | Thr | Arg | Ile | Pro | Lys | Glu | Ile | Met | His | Lys |
| | | | | 245 | | | | | 250 | | | | | 255 | |
| Ile | Pro | Thr | Thr | Leu | Leu | His | Ser | Leu | Glu | Gly | Met | Arg | Asp | Leu | Asp |
| | | | 260 | | | | | 265 | | | | | 270 | | |
| Trp | Glu | Lys | Leu | Leu | Lys | Leu | Gln | Ser | Gln | Asp | Gly | Ser | Phe | Leu | Phe |
| | | 275 | | | | | 280 | | | | | 285 | | | |
| Ser | Pro | Ser | Ser | Thr | Ala | Phe | Ala | Phe | Met | Gln | Thr | Arg | Asp | Ser | Asn |
| | 290 | | | | | 295 | | | | | 300 | | | | |
| Cys | Leu | Glu | Tyr | Leu | Arg | Asn | Ala | Val | Lys | Arg | Phe | Asn | Gly | Gly | Val |
| 305 | | | | | 310 | | | | | 315 | | | | | 320 |
| Pro | Asn | Val | Phe | Pro | Val | Asp | Leu | Phe | Glu | His | Ile | Trp | Ile | Val | Asp |
| | | | | 325 | | | | | 330 | | | | | 335 | |
| Arg | Leu | Gln | Arg | Leu | Gly | Ile | Ser | Arg | Tyr | Phe | Glu | Glu | Glu | Ile | Lys |
| | | | 340 | | | | | 345 | | | | | 350 | | |
| Glu | Cys | Leu | Asp | Tyr | Val | His | Arg | Tyr | Trp | Thr | Asp | Asn | Gly | Ile | Cys |
| | | 355 | | | | | 360 | | | | | 365 | | | |
| Trp | Ala | Arg | Cys | Ser | His | Val | Gln | Asp | Ile | Asp | Asp | Thr | Ala | Met | Ala |
| | 370 | | | | | 375 | | | | | 380 | | | | |
| Phe | Arg | Leu | Leu | Arg | Gln | His | Gly | Tyr | Gln | Val | Ser | Ala | Asp | Val | Phe |
| 385 | | | | | 390 | | | | | 395 | | | | | 400 |

| | | | | | | | | | | | | | | |
|---|---|---|---|---|---|---|---|---|---|---|---|---|---|---|
| Lys | Asn | Phe | Glu | Lys<br>405 | Glu | Gly | Glu | Phe<br>410 | Phe | Cys | Phe | Val | Gly<br>415 | Ser |
| Asn | Gln | Ala | Val<br>420 | Thr | Gly | Met | Phe<br>425 | Asn | Leu | Tyr | Arg | Ala<br>430 | Ser | Gln | Leu |
| Ala | Phe | Pro<br>435 | Arg | Glu | Glu | Ile | Leu<br>440 | Lys | Asn | Ala | Lys<br>445 | Glu | Phe | Ser | Tyr |
| Asn | Tyr<br>450 | Leu | Leu | Glu | Lys | Arg<br>455 | Glu | Arg | Glu | Glu | Leu<br>460 | Ile | Asp | Lys | Trp |
| Ile<br>465 | Ile | Met | Lys | Asp | Leu<br>470 | Pro | Gly | Glu | Ile<br>475 | Gly | Phe | Ala | Leu | Glu | Ile<br>480 |
| Pro | Trp | Tyr | Ala | Ser<br>485 | Leu | Pro | Arg | Val | Glu<br>490 | Thr | Arg | Phe | Tyr | Ile<br>495 | Asp |
| Gln | Tyr | Gly | Gly<br>500 | Glu | Asn | Asp | Val | Trp<br>505 | Ile | Gly | Lys | Thr | Leu<br>510 | Tyr | Arg |
| Met | Pro | Tyr<br>515 | Val | Asn | Asn | Asn | Gly<br>520 | Tyr | Leu | Glu | Leu | Ala<br>525 | Lys | Gln | Asp |
| Tyr | Asn<br>530 | Asn | Cys | Gln | Ala | Gln<br>535 | His | Gln | Leu | Glu | Trp<br>540 | Asp | Ile | Phe | Gln |
| Lys<br>545 | Trp | Tyr | Glu | Glu | Asn<br>550 | Arg | Leu | Ser | Glu | Trp<br>555 | Gly | Val | Arg | Arg | Ser<br>560 |
| Glu | Leu | Leu | Glu | Cys<br>565 | Tyr | Tyr | Leu | Ala | Ala<br>570 | Ala | Thr | Ile | Phe | Glu<br>575 | Ser |
| Glu | Arg | Ser | His<br>580 | Glu | Arg | Met | Val | Trp<br>585 | Ala | Lys | Ser | Ser | Val<br>590 | Leu | Val |
| Lys | Ala | Ile | Ser<br>595 | Ser | Ser | Ser | Phe | Gly<br>600 | Glu | Ser | Ser | Asp | Ser<br>605 | Arg | Arg | Ser |
| Phe | Ser<br>610 | Asp | Gln | Phe | His | Glu<br>615 | Tyr | Ile | Ala | Asn | Ala<br>620 | Arg | Arg | Ser | Asp |
| His<br>625 | His | Phe | Asn | Asp | Arg<br>630 | Asn | Met | Arg | Leu<br>635 | Asp | Arg | Pro | Gly | Ser | Val<br>640 |
| Gln | Ala | Ser | Arg | Leu<br>645 | Ala | Gly | Val | Leu | Ile<br>650 | Gly | Thr | Leu | Asn | Gln<br>655 | Met |
| Ser | Phe | Asp | Leu<br>660 | Phe | Met | Ser | His | Gly<br>665 | Arg | Asp | Val | Asn | Asn<br>670 | Leu | Leu |
| Tyr | Leu | Ser<br>675 | Trp | Gly | Asp | Trp | Met<br>680 | Glu | Lys | Trp | Lys | Leu<br>685 | Tyr | Gly | Asp |
| Glu | Gly<br>690 | Glu | Gly | Glu | Leu | Met<br>695 | Val | Lys | Met | Ile | Ile<br>700 | Leu | Met | Lys | Asn |
| Asn<br>705 | Asp | Leu | Thr | Asn | Phe<br>710 | Phe | Thr | His | Thr<br>715 | His | Phe | Val | Arg | Leu | Ala<br>720 |
| Glu | Ile | Ile | Asn | Arg<br>725 | Ile | Cys | Leu | Pro | Arg<br>730 | Gln | Tyr | Leu | Lys | Ala<br>735 | Arg |
| Arg | Asn | Asp | Glu | Lys<br>740 | Glu | Lys | Thr | Ile | Lys<br>745 | Ser | Met | Glu | Lys<br>750 | Glu | Met |
| Gly | Lys | Met<br>755 | Val | Glu | Leu | Ala | Leu<br>760 | Ser | Glu | Ser | Asp | Thr<br>765 | Phe | Arg | Asp |
| Val | Ser<br>770 | Ile | Thr | Phe | Leu | Asp<br>775 | Val | Ala | Lys | Ala | Phe<br>780 | Tyr | Tyr | Phe | Ala |
| Leu<br>785 | Cys | Gly | Asp | His | Leu<br>790 | Gln | Thr | His | Ile<br>795 | Ser | Lys | Val | Leu | Phe | Gln<br>800 |
| Lys | Val | | | | | | | | | | | | | | |

( 2 ) INFORMATION FOR SEQ ID NO:5:

(i) SEQUENCE CHARACTERISTICS:
(A) LENGTH: 279 amino acids
(B) TYPE: amino acid
(C) STRANDEDNESS: Not Relevant
(D) TOPOLOGY: Not Relevant (ii) MOLECULE TYPE: peptide (xi) SEQUENCE DESCRIPTION: SEQ ID NO:5:

```
Lys Leu Ala Asp Thr Leu Asn Leu Ile Asp Ile Ile Glu Arg Leu Gly
  1               5                  10                  15
Ile Ser Tyr His Phe Glu Lys Glu Ile Asp Glu Ile Leu Asp Gln Ile
                 20                  25                  30
Xaa Xaa Tyr Asn Gln Asn Xaa Xaa Xaa Ser Asn Xaa Xaa Xaa Xaa Xaa
             35                  40                  45
Cys Asn Asp Leu Cys Thr Ser Ala Leu Gln Phe Arg Leu Leu Arg Gln
 50                  55                  60
His Gly Phe Asn Ile Ser Pro Glu Ile Phe Ser Lys Phe Gln Asp Glu
 65                  70                  75                  80
Asn Gly Xaa Xaa Lys Phe Lys Glu Ser Leu Ala Ser Asp Val Leu Gly
                 85                  90                  95
Leu Leu Asn Leu Tyr Glu Ala Ser His Val Arg Thr His Ala Asp Asp
            100                 105                 110
Ile Leu Glu Asp Ala Leu Ala Phe Ser Thr Ile His Leu Xaa Xaa Xaa
            115                 120                 125
Xaa Xaa Xaa Glu Ser Ala Ala Pro His Xaa Xaa Leu Lys Ser Pro Leu
        130                 135                 140
Arg Glu Gln Val Thr His Ala Leu Glu Gln Cys Leu His Lys Gly Val
145                 150                 155                 160
Pro Arg Val Glu Thr Arg Phe Phe Ile Ser Ser Ile Tyr Asp Lys Glu
                165                 170                 175
Gln Ser Lys Xaa Xaa Xaa Xaa Xaa Xaa Xaa Xaa Xaa Xaa Xaa Xaa Asn
            180                 185                 190
Asn Val Leu Leu Arg Phe Ala Lys Leu Asp Phe Asn Leu Leu Gln Met
            195                 200                 205
Leu His Lys Gln Glu Leu Ala Gln Val Ser Arg Trp Trp Lys Asp Leu
    210                 215                 220
Asp Phe Val Thr Thr Leu Pro Tyr Ala Arg Asp Arg Val Val Glu Cys
225                 230                 235                 240
Tyr Phe Trp Ala Leu Gly Val Tyr Phe Glu Pro Gln Tyr Ser Gln Ala
                245                 250                 255
Arg Val Met Leu Val Lys Thr Ile Ser Met Ile Ser Ile Val Asp Asp
            260                 265                 270
Thr Phe Asp Ala Tyr Gly Thr
            275
```

(2) INFORMATION FOR SEQ ID NO:6:

(i) SEQUENCE CHARACTERISTICS:
(A) LENGTH: 279 amino acids
(B) TYPE: amino acid
(C) STRANDEDNESS: Not Relevant
(D) TOPOLOGY: Not Relevant (ii) MOLECULE TYPE: peptide (xi) SEQUENCE DESCRIPTION: SEQ ID NO:6:

```
Asp Ser Val Glu Thr Val Ile Leu Ile Asp Leu Leu Cys Arg Leu Gly
  1               5                  10                  15
```

Val Ser Tyr His Phe Glu Asn Asp Ile Glu Glu Leu Leu Ser Lys Ile
            20                  25                  30

Xaa Xaa Phe Asn Ser Gln Xaa Xaa Xaa Pro Asp Leu Val Asp Glu Lys
            35                  40                  45

Glu Cys Asp Leu Tyr Thr Ala Ala Ile Val Phe Arg Val Phe Arg Gln
    50                  55                  60

His Gly Phe Lys Met Ser Ser Asp Val Phe Ser Lys Phe Lys Asp Ser
65                  70                  75                  80

Asp Gly Xaa Xaa Lys Phe Lys Glu Ser Leu Arg Gly Asp Ala Lys Gly
                85                  90                  95

Met Leu Ser Leu Phe Glu Ala Ser His Leu Ser Val His Gly Glu Asp
            100                 105                 110

Ile Leu Glu Glu Ala Phe Ala Phe Thr Lys Asp Tyr Leu Xaa Xaa Xaa
            115                 120                 125

Xaa Xaa Xaa Gln Ser Ser Ala Val Glu Xaa Xaa Leu Phe Pro Asn Leu
    130                 135                 140

Lys Arg His Ile Thr Asn Ala Leu Glu Gln Pro Phe His Ser Gly Val
145                 150                 155                 160

Pro Arg Leu Glu Ala Arg Lys Phe Ile Asp Leu Tyr Glu Ala Asp Ile
            165                 170                 175

Glu Cys Arg Xaa Xaa Xaa Xaa Xaa Xaa Xaa Xaa Xaa Xaa Xaa Xaa Asn
            180                 185                 190

Glu Thr Leu Leu Glu Phe Ala Lys Leu Asp Tyr Asn Arg Val Gln Leu
            195                 200                 205

Leu His Gln Gln Glu Leu Cys Gln Phe Ser Lys Trp Trp Lys Asp Leu
    210                 215                 220

Asn Leu Ala Ser Asp Ile Pro Tyr Ala Arg Asp Arg Met Ala Glu Ile
225                 230                 235                 240

Phe Phe Trp Ala Val Ala Met Tyr Phe Glu Pro Asp Tyr Ala His Thr
            245                 250                 255

Arg Met Ile Ile Ala Lys Val Val Leu Leu Ile Ser Leu Ile Asp Asp
            260                 265                 270

Thr Ile Asp Ala Tyr Ala Thr
            275

( 2 ) INFORMATION FOR SEQ ID NO:7:

( i ) SEQUENCE CHARACTERISTICS:
        ( A ) LENGTH: 279 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:7:

Asp Gln Ile Arg Gln Leu Glu Leu Ile Asp Asp Leu Gln Arg Met Gly
1                   5                   10                  15

Leu Ser Asp His Phe Gln Asn Glu Phe Lys Glu Ile Leu Ser Ser Ile
            20                  25                  30

Xaa Xaa Tyr Leu Asp His His Tyr Tyr Lys Asn Pro Phe Pro Lys Glu
            35                  40                  45

Glu Arg Asp Leu Tyr Ser Thr Ser Leu Ala Phe Arg Leu Leu Arg Glu
    50                  55                  60

His Gly Phe Gln Val Ala Gln Glu Val Phe Asp Ser Phe Lys Asn Glu
65                  70                  75                  80

| | | | | | | | | | | | | | | | |
|---|---|---|---|---|---|---|---|---|---|---|---|---|---|---|---|
| Glu | Gly | Xaa | Xaa | Glu | Phe | Lys | Glu | Ser | Leu | Ser | Asp | Asp | Thr | Arg | Gly |
| | | | 85 | | | | | 90 | | | | | 95 | | |
| Leu | Leu | Gln | Leu | Tyr | Glu | Ala | Ser | Phe | Leu | Leu | Thr | Glu | Gly | Glu | Thr |
| | | | 100 | | | | | 105 | | | | | 110 | | |
| Thr | Leu | Glu | Ser | Ala | Arg | Glu | Phe | Ala | Thr | Lys | Phe | Leu | Xaa | Xaa | Xaa |
| | | | 115 | | | | | 120 | | | | | 125 | | |
| Xaa | Xaa | Xaa | Glu | Glu | Lys | Val | Asn | Glu | Gly | Gly | Val | Asp | Gly | Asp | Leu |
| | | | 130 | | | | | 135 | | | | | 140 | | |
| Leu | Thr | Arg | Ile | Ala | Tyr | Ser | Leu | Asp | Ile | Pro | Leu | His | Trp | Arg | Ile |
| 145 | | | | | 150 | | | | | 155 | | | | | 160 |
| Lys | Arg | Pro | Asn | Ala | Pro | Val | Trp | Ile | Glu | Trp | Tyr | Arg | Lys | Arg | Pro |
| | | | | 165 | | | | | 170 | | | | | 175 | |
| Asp | Xaa | Met | Xaa | Xaa | Xaa | Xaa | Xaa | Xaa | Xaa | Xaa | Xaa | Xaa | Xaa | Xaa | Asn |
| | | | | 180 | | | | | 185 | | | | | 190 | |
| Pro | Val | Val | Leu | Glu | Leu | Ala | Ile | Leu | Asp | Leu | Asn | Ile | Val | Gln | Ala |
| | | | 195 | | | | | 200 | | | | | 205 | | |
| Gln | Phe | Gln | Glu | Glu | Leu | Lys | Glu | Ser | Phe | Arg | Trp | Trp | Arg | Asn | Thr |
| | | | 210 | | | | | 215 | | | | | 220 | | |
| Gly | Phe | Val | Glu | Lys | Leu | Pro | Phe | Ala | Arg | Asp | Arg | Leu | Val | Glu | Cys |
| 225 | | | | | 230 | | | | | 235 | | | | | 240 |
| Tyr | Phe | Trp | Asn | Thr | Gly | Ile | Ile | Glu | Pro | Arg | Gln | His | Ala | Ser | Ala |
| | | | | 245 | | | | | 250 | | | | | 255 | |
| Arg | Ile | Met | Met | Gly | Lys | Val | Asn | Ala | Leu | Ile | Thr | Val | Ile | Asp | Asp |
| | | | 260 | | | | | 265 | | | | | 270 | | |
| Ile | Tyr | Asp | Val | Tyr | Gly | Thr | | | | | | | | | |
| | | | 275 | | | | | | | | | | | | |

( 2 ) INFORMATION FOR SEQ ID NO:8:

( i ) SEQUENCE CHARACTERISTICS:
        ( A ) LENGTH: 279 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:8:

| | | | | | | | | | | | | | | | |
|---|---|---|---|---|---|---|---|---|---|---|---|---|---|---|---|
| Asp | Leu | Phe | Glu | His | Ile | Trp | Ile | Val | Asp | Arg | Leu | Gln | Arg | Leu | Gly |
| 1 | | | | 5 | | | | | 10 | | | | | 15 | |
| Ile | Ser | Arg | Tyr | Phe | Glu | Glu | Glu | Ile | Lys | Glu | Cys | Leu | Asp | Tyr | Val |
| | | | 20 | | | | | 25 | | | | | 30 | | |
| His | Arg | Tyr | Trp | Thr | Asp | Asn | Gly | Ile | Cys | Trp | Ala | Arg | Cys | Ser | His |
| | | | 35 | | | | | 40 | | | | | 45 | | |
| Val | Gln | Asp | Ile | Asp | Asp | Thr | Ala | Met | Ala | Phe | Arg | Leu | Leu | Arg | Gln |
| | | | 50 | | | | | 55 | | | | | 60 | | |
| His | Gly | Tyr | Gln | Val | Ser | Ala | Asp | Val | Phe | Lys | Asn | Phe | Glu | Lys | Glu |
| 65 | | | | | 70 | | | | | 75 | | | | | 80 |
| Gly | Glu | Phe | Phe | Cys | Phe | Val | Gly | Gln | Ser | Asn | Gln | Ala | Val | Thr | Gly |
| | | | | 85 | | | | | 90 | | | | | 95 | |
| Met | Phe | Asn | Leu | Tyr | Arg | Ala | Ser | Gln | Leu | Ala | Phe | Pro | Arg | Glu | Glu |
| | | | 100 | | | | | 105 | | | | | 110 | | |
| Ile | Leu | Lys | Asn | Ala | Lys | Glu | Phe | Ser | Tyr | Asn | Tyr | Leu | Leu | Glu | Lys |
| | | | 115 | | | | | 120 | | | | | 125 | | |
| Arg | Glu | Arg | Glu | Glu | Leu | Ile | Asp | Lys | Trp | Ile | Ile | Met | Lys | Asp | Leu |
| | | | 130 | | | | | 135 | | | | | 140 | | |
| Pro | Gly | Glu | Ile | Gly | Phe | Ala | Leu | Glu | Ile | Pro | Trp | Tyr | Ala | Ser | Leu |

|     |     |     |     |     |     |     |     |     |     |     |     |     |     |     |     |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |
| Pro | Arg | Val | Glu | Thr | Arg | Phe | Tyr | Ile | Asp | Gln | Tyr | Gly | Gly | Glu | Asn |
|     |     |     |     | 165 |     |     |     |     | 170 |     |     |     |     | 175 |     |
| Asp | Val | Trp | Ile | Gly | Lys | Thr | Leu | Tyr | Arg | Met | Pro | Tyr | Val | Asn | Asn |
|     |     |     | 180 |     |     |     |     | 185 |     |     |     |     | 190 |     |     |
| Asn | Gly | Tyr | Leu | Glu | Leu | Ala | Lys | Gln | Asp | Tyr | Asn | Asn | Cys | Gln | Ala |
|     |     | 195 |     |     |     |     | 200 |     |     |     |     | 205 |     |     |     |
| Gln | His | Gln | Leu | Glu | Trp | Asp | Ile | Phe | Gln | Lys | Trp | Tyr | Glu | Glu | Asn |
|     | 210 |     |     |     |     | 215 |     |     |     |     | 220 |     |     |     |     |
| Arg | Leu | Xaa | Ser | Glu | Trp | Gly | Val | Arg | Arg | Ser | Glu | Leu | Leu | Glu | Cys |
| 225 |     |     |     |     | 230 |     |     |     |     | 235 |     |     |     |     | 240 |
| Tyr | Tyr | Leu | Ala | Ala | Ala | Thr | Ile | Phe | Glu | Ser | Glu | Arg | Ser | His | Glu |
|     |     |     |     | 245 |     |     |     |     | 250 |     |     |     |     | 255 |     |
| Arg | Met | Val | Trp | Ala | Lys | Ser | Ser | Val | Leu | Val | Lys | Ala | Ile | Ser | Ser |
|     |     |     | 260 |     |     |     |     | 265 |     |     |     |     | 270 |     |     |
| Ser | Phe | Gly | Glu | Ser | Ser | Asp |     |     |     |     |     |     |     |     |     |
|     |     | 275 |     |     |     |     |     |     |     |     |     |     |     |     |     |

( 2 ) INFORMATION FOR SEQ ID NO:9:

( i ) SEQUENCE CHARACTERISTICS:
        ( A ) LENGTH: 279 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:9:

|     |     |     |     |     |     |     |     |     |     |     |     |     |     |     |     |
|-----|-----|-----|-----|-----|-----|-----|-----|-----|-----|-----|-----|-----|-----|-----|-----|
| Asp | Leu | Xaa | Glu | Xaa | Xaa | Xaa | Xaa | Xaa | Asp | Xaa | Leu | Gln | Arg | Leu | Gly |
| 1   |     |     |     | 5   |     |     |     |     | 10  |     |     |     |     | 15  |     |
| Ile | Ser | Xaa | Xaa | Phe | Glu | Xaa | Glu | Ile | Lys | Glu | Xaa | Leu | Asp | Xaa | Xaa |
|     |     |     | 20  |     |     |     |     | 25  |     |     |     |     | 30  |     |     |
| Xaa | Xaa | Tyr | Xaa | Xaa | Xaa | Xaa | Xaa | Xaa | Xaa | Xaa | Xaa | Xaa | Xaa | Xaa | Xaa |
|     |     | 35  |     |     |     |     | 40  |     |     |     |     | 45  |     |     |     |
| Xaa | Xaa | Asp | Xaa | Xaa | Xaa | Thr | Ala | Xaa | Ala | Phe | Arg | Leu | Leu | Arg | Gln |
|     | 50  |     |     |     |     | 55  |     |     |     |     | 60  |     |     |     |     |
| His | Gly | Xaa | Gln | Val | Ser | Xaa | Asp | Val | Phe | Xaa | Xaa | Phe | Xaa | Xaa | Glu |
| 65  |     |     |     |     | 70  |     |     |     |     | 75  |     |     |     |     | 80  |
| Xaa | Xaa | Xaa | Xaa | Xaa | Phe | Xaa | Xaa | Xaa | Xaa | Xaa | Xaa | Xaa | Val | Xaa | Gly |
|     |     |     |     | 85  |     |     |     |     | 90  |     |     |     |     | 95  |     |
| Met | Xaa | Asn | Leu | Tyr | Xaa | Ala | Ser | Xaa | Leu | Xaa | Xaa | Xaa | Xaa | Glu | Xaa |
|     |     |     | 100 |     |     |     |     | 105 |     |     |     |     | 110 |     |     |
| Ile | Leu | Xaa | Xaa | Ala | Xaa | Glu | Phe | Ser | Xaa | Xaa | Tyr | Leu | Xaa | Xaa | Xaa |
|     |     | 115 |     |     |     |     | 120 |     |     |     |     | 125 |     |     |     |
| Xaa | Xaa | Xaa | Glu | Glu | Xaa | Xaa | Xaa | Xaa | Xaa | Xaa | Xaa | Xaa | Xaa | Asp | Leu |
|     | 130 |     |     |     |     | 135 |     |     |     |     | 140 |     |     |     |     |
| Xaa | Xaa | Xaa | Ile | Xaa | Xaa | Ala | Leu | Glu | Ile | Pro | Xaa | Xaa | Xaa | Xaa | Xaa |
| 145 |     |     |     |     | 150 |     |     |     |     | 155 |     |     |     |     | 160 |
| Pro | Arg | Val | Glu | Thr | Arg | Phe | Xaa | Ile | Asp | Xaa | Tyr | Xaa | Xaa | Xaa | Xaa |
|     |     |     |     | 165 |     |     |     |     | 170 |     |     |     |     | 175 |     |
| Asp | Xaa | Xaa | Xaa | Xaa | Xaa | Xaa | Xaa | Xaa | Xaa | Xaa | Xaa | Xaa | Xaa | Xaa | Asn |
|     |     |     | 180 |     |     |     |     | 185 |     |     |     |     | 190 |     |     |
| Asn | Xaa | Xaa | Leu | Glu | Leu | Ala | Lys | Xaa | Asp | Tyr | Asn | Xaa | Xaa | Gln | Ala |
|     |     | 195 |     |     |     |     | 200 |     |     |     |     | 205 |     |     |     |
| Gln | His | Gln | Xaa | Glu | Xaa | Xaa | Xaa | Phe | Xaa | Lys | Trp | Xaa | Xaa | Xaa | Xaa |
|     | 210 |     |     |     |     | 215 |     |     |     |     | 220 |     |     |     |     |

-continued

| | | | | | | | | | | | | | | | |
|---|---|---|---|---|---|---|---|---|---|---|---|---|---|---|---|
| Xaa 225 | Leu | Xaa | Ser | Xaa | Xaa 230 | Xaa | Xaa | Xaa | Arg | Xaa 235 | Xaa | Leu | Xaa | Glu | Cys 240 |
| Tyr | Xaa | Xaa | Ala | Xaa 245 | Ala | Xaa | Ile | Phe | Glu 250 | Xaa | Xaa | Xaa | Ser | His 255 | Xaa |
| Arg | Met | Xaa | Xaa 260 | Ala | Lys | Xaa | Xaa | Xaa 265 | Leu | Xaa | Xaa | Xaa | Ile 270 | Xaa | Xaa |
| Xaa | Phe | Xaa 275 | Xaa | Xaa | Xaa | Xaa | | | | | | | | | |

RECOMBINANT GIBBERELLIN DNA AND USES THEREOF

CROSS-REFERENCE TO RELATED PATENT APPLICATIONS

This application is a continuation-in-part of U.S. patent application Ser. No. 08/261,769 (filed Jun. 17, 1994) now abandoned, which is a continuation in part of U.S. patent application Ser. No. 08/008,996 (filed Jan. 27, 1993) now abandoned, which is a continuation-in-part of U.S. patent application Ser. No. 07/844,300 (filed Feb. 18, 1992) now abandoned, each of which are fully incorporated herein by reference.

Statement as to Rights to Inventions Made Under Federally-Sponsored Research and Development Part of the work performed during development of this invention utilized U.S. Government funds. The U.S. Government may have certain rights in this invention.

FIELD OF THE INVENTION

The invention pertains to recombinant DNA technology. Specifically, the invention relates to cDNA and genomic DNA corresponding to the GA1 locus of *Arabidopsis thaliana* which encodes ent-kaurene synthetase, expression vectors containing such genes, hosts transformed with such vectors, the regulatory regions of the GA1 gene, the use of such regulatory regions to direct the expression of operably-linked heterologous genes in transgenic plants, the GA1 protein substantially free of other *A. thaliana* proteins, antibodies capable of binding to the GA1 protein, and to methods of assaying for the expression of the GA1 gene and the presence of GA1 protein in plant cells and tissues.

BACKGROUND OF THE INVENTION

A. Gibberellins

Gibberellins (GAs) are a family of diterpenoid plant growth hormones some of which are bioactive growth regulators. GAs are required for controlling such diverse processes as seed germination, cell elongation and division, leaf expansion, stem elongation, flowering, and fruit set. GAs have been the subject of many physiological, and biochemical studies, and a variety of plant mutants with altered patterns of GA biosynthesis or response have been studied (Graebe, J. E., *Ann. Rev. Plant Physiol.* 38:419–465 (1987)). However, none of the genes involved in GA synthesis have yet been cloned.

Extensive biochemical studies on endogenous GA intermediates in GA-responsive dwarf mutants have allowed the determination of the GA biosynthetic pathway and several genetic loci involved in GA biosynthesis (reviewed by Graebe, J. E., *Ann. Rev. Plant Physiol.* 38:419–465 (1987)). A number of the GA responsive dwarf mutants have been isolated from various plant species, such as maize, pea, and Arabidopsis (Phinney, B. O. et al., "Chemical Genetics and the Gibberellin Pathway" in *Zea mays L. in Plant Growth Substance*, ed., P. F. Waering, New York: Academic (1982) pp. 101–110; Ingram, T. J. et al., *Planta* 160:455–463 (1984); Koornneef, M., *Arabidopsis Inf. Serv.* 15:17–20. (1978)). The dwarf mutants of maize (dwarf-1, dwarf-2, dwarf-3, dwarf-5) have been used to characterize the maize GA biosynthesis pathway by determining specific steps leading to biologically important metabolites (Phinney, B. O. et al., "Chemical Genetics and the Gibberellin Pathway" in *Zea mays L. in Plant Growth Substance*, ed., P. F. Waering, New York: Academic (1982) pp. 101–110; Fujioka, S. et al., *Plant Physiol.* 88:1367–1372 (1988)). Similar studies have been done with the dwarf mutants from pea (*Pisum sativum* L.) (Ingram, T. J. et al., *Planta* 160:455–463 (1984)). GA deficient mutants have also been isolated from Arabidopsis (ga1, ga2, ga3, ga4, ga5) (Koornneef, M., et al., *Theor. Appl. Genet.* 58:257–263 (1980)). One of the most extensive genetic studies of GA mutants has been carried out by Koornneef et al. (*Theor. Appl. Genet.* 58:257–263 (1980); Koornneef et al., *Genet. Res. Camb.* 41:57–68 (1983)) in the small crucifer, *Arabidopsis thaliana*. Using ethylmethanesulfonate (EMS) and fast neutron mutagenesis, Koornneef has isolated nine alleles mapping to the GA1 locus of *A. thaliana* (Koornneef et al. (*Theor. Appl. Genet.* 58:257–263 (1980); Koornneef et al., *Genet. Res. Camb.* 41:57–68 (1983)).

*A. thaliana* ga1 mutants are non-germinating, GA-responsive, male-sterile dwarfs, whose phenotype can be converted to wild-type by repeated application of GA (Koornneef and van der Veen, *Theor. Appl. Genet.* 58:257–263 (1980)). Koornneef et al. used three independent alleles generated by fast neutron bombardment (31.89, 29.9 and 6.59) and six independent alleles (NG4, NG5, d69, A428, d352 and Bo27) generated by ethyl methane sulfonate mutagenesis to construct a fine-structure genetic map of the *A. thaliana* GA1 locus (FIG. 2A). One of the fast-neutron-generated mutants, 31.89, failed to recombine with the six alleles indicated in FIG. 2A, and was classified as an intragenic deletion (Koornneef et al., *Genet. Res. Camb.* 41:57–68 (1983)).

The ga1 mutants contain reduced levels of GAs and the ent-kaurene synthetase activity in cell-free preparations from ga1 mutants is very low compared to wild type (Barendse et al., *Physiol. Plant.* 67: 315–319 (1986); Barendse and Koornneef, *Arab. Inf. Serv.* 19: 25–28 (1982)). Zeevaart, *Plant Research '86, Annual Report of the MSU-DOE Plant Research Laboratory*, (East Lansing, Mich.), pp. 130–131 (1986), reported that application of ent-kaurene also restored growth of the ga1 mutants, and that $^{14}$C-ent-kaurene was metabolized to GAs when applied to the leaves of these mutants. These results suggest that GA biosynthesis in the ga1 mutants is blocked prior to the formation of ent-kaurene, but the rest of the pathway is unaffected by the mutation. Since the ga1 mutants produce chlorophylls and carotenoids, it is unlikely that the mutation affects the synthesis of geranylgeranyl pyrophosphate (GGPP). Therefore, the GA1 locus is probably involved in the conversion of GGPP to ent-kaurene, encoding one of the ent-kaurene synthetases or a regulator needed for formation of the active enzyme. The GA1 locus has been isolated by genomic subtraction (Sun et al., *Plant Cell* 4:119–128 (1992)).

The enzyme encoded by the GA1 gene is involved in the conversion of GGPP to ent-kaurene (Barendse and Koornneef, *Arabidopsis Inf. Serv.* 19:25–28 (1982); Barendse et al., *Physiol. Plant.* 67:315–319 (1986); Zeevaart, J. A. D., in *Plant Research '86, Annual Report of the MSU-DOE Plant Research Laboratory*, 130–131 (East Lansing, Mich., 1986)), a key intermediate in the biosynthesis of GAs (Graebe, J. E., *Ann. Rev. Plant Physiol.* 38:419–465 (1987)).

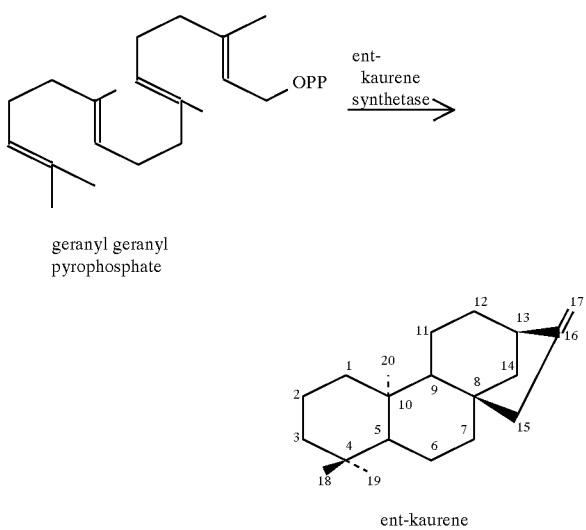

geranyl geranyl pyrophosphate ent-kaurene

Ent-kaurene synthetase has only been partially purified from a variety of plants (Duncan, *Plant Physiol.* 68:1128–1134 (1981)).

The synthesis of GGPP from mevalonate is common to terpenes. GGPP is a branch point metabolite which is not only the precursor of GAs, but also a precursor of other diterpenes, such as the phytol chain of chlorophylls, and tetraterpenes, such as the carotenoids. The first committed step of the GA pathway is the conversion of GGPP to ent-kaurene in a two-step cyclization reaction. GGPP is partially cyclized to the intermediate, copalyl pyrophosphate (CPP), by ent-kaurene synthetases A and CPP is immediately converted to ent-kaurene by ent-kaurene synthetase B. Since ent-kaurene is a key intermediate in the GA pathway, its synthesis is likely to be a regulatory point for GA biosynthesis. Indeed, ent-kaurene production has been shown to be altered by changes in photoperiod, temperature, and growth potential of tissues in certain species (Chung and Coolbaugh, 1986; Moore and Moore, 1991; Zeevaart and Gage, 1993).

By examining the molecular lesions in several ga1 alleles, a direct correlation of the genetic and physical maps of the GA1 locus was established and a recombination rate of $10^{-5}$ cM per nucleotide was determined for this region of the *A. thaliana* genome. (Koornneef, *Genet. Res. Comb.* 41:57–68 (1983)).

The difficulty associated with cloning the GA1 gene and other genes involved in GA biosynthesis has most been likely caused by the unavailability of efficient transformation/selection systems as well as the lack of available protein sequences. Although ga1 mutants have been available for some time, the cloning of the GA1 gene has remained elusive. The claimed invention solves, inter alia, this problem.

B. Gene Cloning

The ability to identify and clone a particular, desired gene sequence from a virus, prokaryote or eukaryote is of tremendous significance to molecular biology. Such cloned gene sequences can be used to express a desired gene product and therefore can potentially be used for applications ranging from catalysis to gene replacement.

A variety of methods have been developed for isolating and cloning desired gene sequences. Early methods permitted only the identification and isolation of gene sequences that possessed a unique property such as proximity to a prophage integration site, capacity for self-replication, distinctive molecular weight, extreme abundance, etc. (*The Bacteriophage Lambda*, A. D. Hershey, ed., Cold Spring Harbor Press, Cold Spring Harbor, N.Y. (1971); Miller, J. H. *Experiments in Molecular Genetics*, Cold Spring Harbor Press, Cold Spring Harbor, N.Y. (1972); *Molecular Biology of the Gene*, Watson, J. D. et al., (4th ed.) Benjamin/Cummings, Menlo Park, Calif. (1987); Darnell, J. et al. *Molecular Biology*, Scientific American Books, New York, N.Y. (1986)). Because these methods relied upon distinctive properties of a gene sequence, they were largely (or completely) unsuitable for identifying and cloning most gene sequences.

In order to identify desired gene sequences that lacked a distinctive property, well characterized genetic systems (such as *Escherichia coli, Saccharomyces cerevisiae*, maize, mammalian cells, etc.) have been exploited. In accordance with this methodology, cells are mutagenized by chemicals, such as UV light, hydroxylamine, etc. (Miller, J. H. *Experiments in Molecular Genetics*, Cold Spring Harbor Press, Cold Spring Harbor, N.Y. (1972)), or by genetic means, such as transposon tagging (Davis, R. W. et al. *A Manual for Genetic Engineering, Advanced Bacterial Genetics*, Cold Spring Harbor Press, Cold Spring Harbor, N.Y. (1980)), to produce mutants having discernible genetic deficiencies. A desired gene sequence is then identified by its capacity to complement (i.e. remedy) the genetic deficiencies of such mutant cells. Such genetic identification permitted the genetic characterization of the gene sequences, and the construction of genetic maps which localized the gene sequence to a region of a particular chromosome (Taylor, *Bacteriol. Rev.* 34:155 (1970)). With the advent of recombinant DNA technologies, it became possible to clone (i.e. to physically isolate) such genetically characterized gene sequences. Random fragments of a genome could be introduced into self-replicating vectors to produce gene libraries, each of whose members contain a unique DNA fragment (Maniatis, T. et al., In: *Molecular Cloning, a Laboratory Manual*, Cold Spring Harbor Press, Cold Spring Harbor, N.Y. (1982)). By screening the members of such libraries for those capable of complementing the deficiency of a mutant cell, it was possible to clone the desired gene sequence.

Although these methods permit the identification and cloning of many gene sequences, they may be employed only where a host cell exists that has a mutation conferring a discernible deficiency, and the gene sequence can be cloned into a gene sequence delivery system (such as a vector) capable of entering the host cell and being expressed.

The capacity to physically isolate certain gene sequences has led to the development of methods that are capable of isolating a desired gene sequence even in the absence of mutations or vectors.

In one such technique, known as "chromosome walking," a desired sequence can be obtained by isolating a gene sequence that is capable of hybridizing to a particular reference sequence. This isolated gene sequence is then employed as a reference sequence in a subsequent hybridization experiment in order to clone a gene sequence that is adjacent to, and that partially overlaps, the originally isolated sequence. This newly isolated sequence will be physically closer to the desired gene sequence than was the originally isolated sequence. This process is repeated until the desired gene sequence has been obtained. As will be appreciated, the ability to clone a gene sequence, in the absence of genetic mutants or vectors, requires some initial information concerning the nucleotide sequence or restriction endonuclease digestion profile of the desired sequence.

Alternatively, the chromosome of a virus or cell can be characterized to produce a physical map based on either nucleotide sequence or restriction endonuclease cleavage data (i.e. an RFLP map). Using such a map, restriction fragments of the chromosome can be cloned without any prior determination as to their genetic function.

More recently, gene cloning has been achieved by synthesizing oligonucleotide molecules using sequences deduced from the amino acid sequence of an isolated protein. cDNA copies of isolated RNA transcripts are made and differential colony or library subtractive hybridizations using either two different RNA sources, or cDNA and RNA is performed to identify the desired clone.

Although these methods may be employed even in the absence of mutants or a gene sequence delivery system, they permit a desired gene sequence to be identified and cloned only if sequences naturally linked to the desired sequence have been characterized and isolated, or if the sequence or restriction map of such sequences has been obtained. Since such data are often unavailable, these methods are often incapable of use in identifying and cloning a desired gene sequence.

Two general approaches have been described for cloning sequences that are present in one strain and absent in another. The first approach, differential screening, has been used to clone the esc gene from Drosophila. Using genomic DNA from strains with and without a deletion to probe replicas of a genomic library poses technical difficulties that become daunting for large genomes. In addition, the deletion must cover at least one entire insert in a genomic library that does not contain any repeated sequences.

The second approach, competitive hybridization, provides an alternative to differential screening. This technique was used by Lamar et al. (*Cell* 37:171–177 (1984)) to isolate clones specific for the human Y chromosome. In accordance with this method, an excess of sheared DNA from a human female is denatured and reannealed along with a small amount of DNA from a male (the male-derived DNA having been previously treated to have sticky ends). Most of the male DNA reassociated with the sheared DNA yielding unclonable fragments lacking sticky ends. Fragments unique to the Y chromosome, however, could only reassociate with the complementary restricted strand (derived from the Y chromosome). Such reassociation thus formed clonable fragments with sticky ends. This technique has also been used successfully to clone DNA corresponding to deletions in the Duchenne muscular dystrophy locus, and choroideremia.

Unfortunately, the competitive hybridization method does not provide a large enough degree of enrichment. For example, enrichments of about one hundred fold were obtained for the sequences of interest in the above experiments. With enrichments of such low magnitude, the technique is practical only when dealing with large deletions. Indeed, even if the deletion covered 0. 1% of the genome, many putative positive clones have to be tested individually by labeling and probing genomic Southern blots (Southern, J., *J. Molec. Biol.* 98:503–517 (1975)). The method as it stands, then, is not practical for deletions on the order of 1 kbp (kilobasepair) unless one is dealing with a small prokaryotic genome.

Thus, in summary, the ability to clone DNA corresponding to a locus defined only by a mutation is a relatively simply matter when working with *E. coli, S. cerevisiae* or other organisms in which transformation and complementation with genomic libraries is feasible. Chromosome walking techniques may be used in other organisms to clone genetically defined loci if the mutant was obtained by transposon tagging, if the locus can be linked to markers in an RFLP map, or if an ordered library for the genome exists. Unfortunately, there are numerous organisms in which mutants with interesting phenotypes have been isolated but for which such procedures have not been developed, such as the GA synthesis mutants of *A. thaliana*. Thus, many gene sequences cannot be isolated using the above methods.

C. Transgenic and Chimeric Plants

Recent advances in recombinant DNA and genetic technologies have made it possible to introduce and express a desired gene sequence in a recipient plant. Through the use of such methods, plants have been engineered to contain gene sequences that are not normally or naturally present in an unaltered plant. In addition, these techniques have been used to produce plants which exhibit altered expression of naturally present gene sequences.

The plants produced through the use of these methods are known as either "chimeric" or "transgenic" plants. In a "chimeric" plant, only some of the plant's cells contain and express the introduced gene sequence, whereas other cells remain unaltered. In contrast, all of the cells of a "transgenic" plant contain the introduced gene sequence.

Transgenic plants generally are generated from a transformed single plant cell. Many genera of plants have been regenerated from a single cell. (Friedt, W. et al. *Prog. Botany* 49:192–215 (1987); Brunold, C. et al., *Molec. Gen. Genet.* 208:469–473 (1987); Durand, J. et al., *Plant Sci.* 62:263–272 (1989) which references are incorporated herein by reference).

Several methods have been developed to deliver and express a foreign gene into a plant cell. These include engineered Ti plasmids from the soil bacterium *A. tumefaciens* (Czako, M. et al., *Plant Mol. Biol.* 6:101–109 (1986); Jones, J. D. G. et al., *EMBO J*. 4:2411–2418 (1985), engineered plant viruses such as the cauliflower mosaic virus (Shah, D. M. et al., *Science* 233:478–481 (1986)); Shewmaker, C. K. et al., *Virol.* 140:281–288 (1985)), microinjection of gene sequences into a plant cell (Crossway, A. et al., *Molec. Gen. Genet.* 202:179–185 (1986); Potrykus, I. et al., *Molec. Gen. Genet.* 199:169–177 (1985)), electroporation (Fromm, M. E. et al., *Nature* 319:791–793 (1986); Morikawa, H. et al., *Gene* 41:121–124 (1986)), and DNA coated particle acceleration (Bolik, M. et al. *Protoplasma* 162:61–68 (1991)).

The application of the technologies for the creation of transgenic and chimeric plants has the potential to produce plants that cannot be generated using classical genetics. For example, chimeric and transgenic plants have substantial use as probes of natural gene expression. When applied to food crops, the technologies have the potential of yielding improved food, fiber, etc.

Chimeric and transgenic plants having a specific temporal and spatial pattern of expression of the introduced gene sequence can be generated. The expression of an introduced gene sequence can be controlled through the selection of regulatory sequences to direct transcription and or translation in a temporal or spatial fashion.

SUMMARY OF THE INVENTION

The invention is directed to isolated genomic DNA and cDNA corresponding to the GA1 locus of *A. thaliana*, vectors containing such DNA, hosts transformed with such vectors, the regulatory regions that control the expression of the GA1 protein, and the use of such regulatory sequences to direct the expression of a heterologous gene.

The invention is further directed to GA1 antisense DNA, and to the GA1 antisense RNA transcribed from it.

The invention is further directed to vectors containing GA1 encoding DNA and to the expression of GA1 protein encoded by the GA1 DNA in a host cell.

The invention is further directed to vectors containing GA1 antisense DNA and to the expression of GA1 antisense RNA in a host cell.

The invention is further directed to host cells transformed with the GA1 encoding DNA of the invention, and to the use of such host cells for the maintenance of the GA1 DNA or expression of the GA1 protein of the invention.

The invention is further directed to host cells transformed with the GA1 antisense DNA of the invention, and to the use of such host cells for the maintenance of the GA1 DNA or inhibition of expression of the GA1 protein of the invention.

The invention is further directed to the GA1 protein, substantially free of other *A. thaliana* proteins, antibodies capable of binding the GA1 protein, and the use of such GA1 protein and antibodies thereto.

The invention is further directed to chimeric and transgenic plants transformed with the GA1 encoding or GA1 antisense DNA sequence, or transformed with a heterologous gene controlled by the regulatory sequences of the GA1 gene.

The invention is further directed to a method for altering plant growth, using the GA1 encoding or GA1 antisense DNA of the invention The invention is further directed to a method for altering plant growth, using the recombinantly made GA1 protein of the invention.

The invention further concerns the use of sequences encoding the GA1 protein and antibodies capable of binding to the GA1 protein to detect the expression of GA1 and to isolate the regulatory proteins which bind to GA1 gene sequences.

BRIEF DESCRIPTION OF THE FIGURES

FIGS. 2A–2B. Genetic and physical maps of the *A. thaliana* GA1 locus.

FIG. 2A: Genetic map in cM×$10^{-2}$ of nine *A. thaliana* ga-1 alleles (29.9, NG5, NG4, d69, A428, d325, 6.59, Bo27, 31.89) (Koornneef et al., Genet. Res. Camb. 41:57–68 (1983)). The presumptive deletion in 31.89 is indicated by the horizontal line.

FIG. 2B: Physical map of the GA1 region. The heavy horizontal line is a HindIII restriction map of the Landsberg erecta DNA encompassing the GA-1 locus. HindIII restriction sites are depicted by vertical ticks extending below the horizontal line. The numbers immediately below the heavy horizontal line represent the size, in kilobase pairs, of the respective HindIII restriction fragments. The location of the deletion in 31.89 is indicated by the hatched box. The horizontal lines above the restriction map indicate the extent of the sequences contained in the λ clone λGA1-3, the plasmid pGA1-2 (deposited Jan. 7, 1993 pursuant to the provisions of the Budapest Treaty on the International Recognition of the Deposit of Microorganisms For The Purposes of Procedure (Budapest Treaty) with the American Type Culture Collection (ATCC) in Rockville, Md., U.S.A. 20852, and identified by ATCC Accession No. 75394), and the cosmid clone pGA1-4 (deposited Jan. 7, 1993 pursuant to the provisions of the Budapest Treaty on the International Recognition of the Deposit of Microorganisms For The Purposes of Procedure (Budapest Treaty) with the American Type Culture Collection (ATCC) in Rockville, Md., U.S.A. 20852, and identified by ATCC Accession No. 75395). The diagram below the horizontal lines depicts the location of introns (lines) and exons (open boxes) of the GA1 gene within the 1.2 kb HindIII restriction fragment and the locations of the insertion mutation in allele 6.59 and the point mutations in alleles, d352, A428 and Bo27.

(FIG. 4A) Photograph of six-week-old *A. thaliana* Landsberg erecta plants. Left to right: a ga-1 mutant (31.89), a transgenic ga-1 mutant (31.89) plant containing the 20 kb insert from pGA1-4 (ATCC No. 75395), a wild-type Landsberg erecta plant. Autoradiograms are shown for Southern blots probed with (FIG. 4B) the 6 kb fragment from pGA1-2 (ATCC No. 75394), and (FIG. 4C) pOCA18 DNA, which is the vector for pGA1-4 (ATCC No. 75395) (see FIG. 2). Blots in FIGS. 4B and 4C contain HindIII-digested DNA from Landsberg erecta (lane 1 in FIG. 4B), Columbia (lane 2 in FIG. 4B, lane 1 in FIG. 4C), 31.89 (lane 3 in FIG. 4B, lane 2 in FIG. 4C), and two T3 generation transgenic ga-1 (31.89) plants transformed with pGA1-4 (ATCC No. 75395) (lane 4,5 in FIG. 4B; lanes 3,4 in FIG. 4C).

FIG. 6A–6B (SEQ ID NO: 1). Partial cDNA sequence of the GA1 gene. The GA1 DNA strand complementary to GA1 mRNA is shown in a 5'-3' orientation. The GA1 variant d352 has the identical sequence to that shown except for the substitution of an A for the G at position 425. The GA1 variant A428 has the identical sequence to that shown except for the substitution of a T for the C at position 420. The GA1 variant Bo27 has the identical sequence to that shown except for the substitution of a T for the C at position 246.

FIG. 7A–7B (SEQ ID NO: 2). Partial cDNA sequence of the GA1 gene. The GA1 DNA strand shown is analogous to GA1 mRNA and complementary to the strand shown in FIG. 6. The GA1 variant d352 has the identical sequence to that shown except for the substitution of a T for the C at position 479. The GA1 variant A428 has the identical sequence to that shown except for the substitution of an A for the G at position 484. The GA1 variant Bo27 has the identical sequence to that shown except for the substitution of an A for the G at position 658.

FIG. 8(SEQ ID NO: 4). The complete amino acid sequence of the GA1 protein is shown, as determined from the cDNA sequence of FIG. 9A–9C.

FIG. 9A–9C (SEQ ID NO: 3). Nucleotide sequences of 2.6 kb GA1 cDNA and predicted amino acid sequence. The nucleotide sequence has been submitted to GenBank as accession number U 11034. Nucleotide 1 corresponds to the start codon of the open reading frame of 2406 bps. The inverted triangles mark the position of introns as deduced by comparison of the cDNA and genomic DNA sequences. The locations of single nucleotide changes in ga1-6, 7, 8, and 9 alleles are indicated by underlines and the substituted bases are above the sequence. The ga1-4 allele contains a small deletion of 14 nucleotides from 2375 to 2388 as indicated by two arrows.

FIGS. 12A–12E are mass chromatograms at m/z 290 (molecular ion of GGol and copalol). FIGS. 12A–12B are authentic GGol and copalol standards, respectively. FIGS. 12C–12E contain hydrolyzed *E. coli* extracts from cells carrying only pACCRT-E (GGPP synthase), pACCRT-E and pGA1-40 (30 kD truncated GA1 protein), pACCRT-E and pGA1-43 (86 kD GA1 protein), respectively.

FIG. 15 (SEQ ID NO: 5–9). Sequence alignment of the GA1 protein compared to tobacco sesquiterpene cyclase (tobsqpc), casbene synthase, and limonene synthase. Letters in upper case in the consensus sequence indicate that all four proteins contain the same amino acid residue. When at least one letter in the first three peptides is the same as that of the GA1 protein, the consensus character is in the lower case. The dot indicates that there is no homology between the first three proteins and the GA1 protein. The putative divalent metal ion-pyrophosphate complex binding site (DDXXD) is marked by the box. The DXDDTA motif in the GA1 sequence is highlighted in boldface.

DESCRIPTION OF THE PREFERRED EMBODIMENTS

Figure 1:
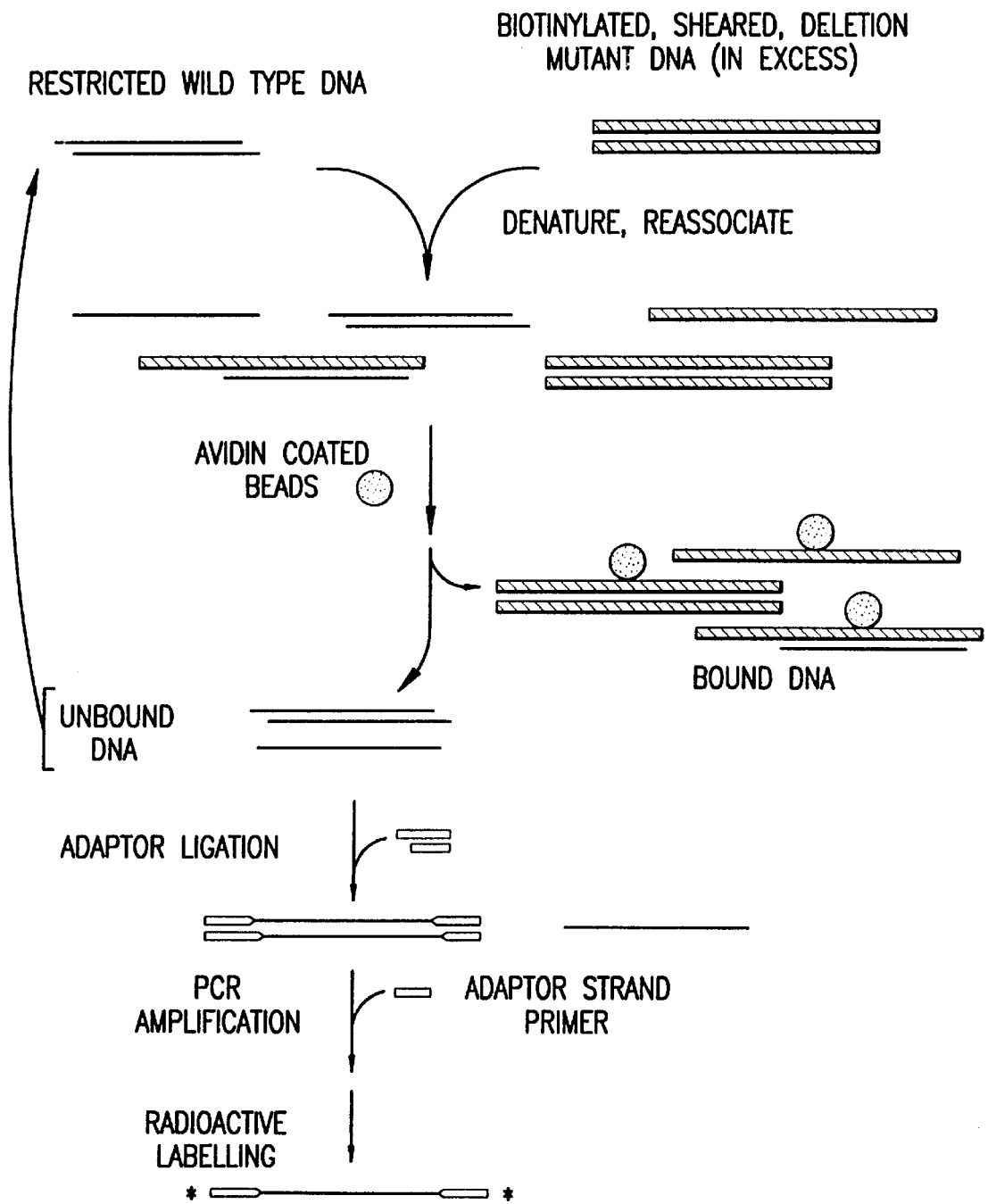
FIG. 1. A diagram of the enrichment and cloning method of the preferred embodiment of the present invention. DNA is depicted as a solid line; biotinylated DNA is depicted as a striped black/white line; Sau3a adaptors are shown as an open line; avidin beads are shown as speckled circles; radiolabelled fragments are shown with asterisks.

Using genomic subtraction, a gene involved in the synthesis of GA has been isolated. Genomic subtraction is a method for enriching, and clonally isolating, a gene sequence present in one nucleic acid population but absent in another. Following the procedures outlined herein that demonstrate the cloning of the GA1 gene, it is now also possible to isolate other genes involved in GA synthesis.

A. The GA1 gene from *A. thaliana*

Using the technique of genomic subtraction, a gene involved in the synthesis of GA, encoded by the GA1 locus of *A. thaliana*, has been cloned (hereinafter the GA1 gene, Example 1).

In one embodiment of the present invention, vectors containing genomic DNA or cDNA encoding the GA1 protein, or a fragment thereof, are provided. Specifically, such vectors are capable of generating large quantities of the GA1 sequence, substantially free of other *A. thaliana* DNA. As used herein plant should be understood as referring to a multicellular differentiated organism capable of photosynthesis including angiosperms (monocots and dicots) and gymnosperms.

As used herein plant cell should be understood as referring to the structural and physiological unit of plants. The term "plant cell" refers to any cell that is either part of or derived from a plant. Some examples of cells encompassed by the present invention include differentiated cells that are part of a living plant; differentiated cells in culture; undifferentiated cells in culture; the cells of undifferentiated tissue such as callus or tumors.

As used herein plant cell progeny should be understood as referring to any cell or tissue derived from plant cells including callus; plant parts such as stems, roots, fruits, leaves or flowers; plants; plant seed; pollen; and plant embryos.

Propagules should be understood as referring to any plant material capable of being sexually or asexually propagated, or being propagated in vivo or in vitro. Such propagules preferably consist of the protoplasts, cells, calli, tissues, embryos or seeds of the regenerated plants.

Transgenic plant should be understood as referring to a plant having stably incorporated exogenous DNA in its genetic material. The term also includes exogenous DNA that may be introduced into a cell or protoplast in various forms, including, for example, naked DNA in circular, linear or supercoiled form, DNA contained in nucleosomes or chromosomes or nuclei or parts thereof, DNA complexed or associated with other molecules, DNA enclosed in liposomes, spheroplasts, cells or protoplasts.

A mutation should be understood as referring to a detectable change in the genetic material that may be transmitted to daughter cells and possibly even to succeeding generations giving rise to mutant cells or mutant organisms. If the descendants of a mutant cell give rise only to somatic cells in multicellular organisms, a mutant spot or area of cells arises. Mutations in the germ line of sexually reproducing organisms may be transmitted by the gametes to the next generation resulting in an individual with the new mutant condition in both its somatic and germ cells. A mutation may be any (or a combination of) detectable, unnatural change affecting the chemical or physical constitution, mutability, replication, phenotypic function, or recombination of one or more deoxyribonucleotides; nucleotides may be added, deleted, substituted for, inverted, or transposed to new positions with and without inversion. Mutations may occur spontaneously and can be induced experimentally by application of mutagens. A mutant variation of a nucleic acid molecule results from a mutation. A mutant polypeptide may result from a mutant nucleic acid molecule.

A species should be understood as referring to a group of actually or potentially interbreeding natural populations. A species variation within a nucleic acid molecule or protein is a change in the nucleic acid or amino acid sequence that occurs among species and may be determined by DNA sequencing of the molecule in question.

Vectors for propagating a given sequence in a variety of host systems are well known and can readily be altered by one of skill in the art such that the vector will contain the GA1 sequence and will be propagated in a desired host. Such vectors include plasmids and viruses and such hosts include eukaryotic organisms and cells, for example yeast, insect, plant, mouse or human cells, and prokaryotic organisms, for example *E. coli* and *B. subtillus*.

As used herein, a sequence is said to be "substantially free of other *A. thaliana* DNA" when the only *A. thaliana* DNA present in the sample or vector is of the specificically referenced sequence.

As used herein, a "DNA construct" refers to a recombinant, man-made DNA.

As used herein, "a fragment thereof" relates to any polynucleotide subset of the entire GA1 sequence. The most preferred fragments are those containing the active site of the enzyme encoded by GA1, or the regulatory regions of the GA1 protein and gene respectively.

In a further embodiment of the present invention, expression vectors are described that are capable of expressing and producing large quantities of the GA1 protein, substantially free of other *A. thaliana* proteins.

As used herein, a protein is said to be "substantially free of other *A. thaliana* proteins" when the only *A. thaliana* protein present in the sample is the expressed protein. Though proteins may be present in the sample that are homologous to other *A. thaliana* proteins, the sample is still said to be "substantially free of other *A. thaliana* proteins" as long as the homologous proteins contained in the sample are not expressed from genes obtained from *A. thaliana*.

A nucleic acid molecule, such as DNA, is said to be "capable of expressing" a polypeptide if it contains nucleotide sequences that contain transcriptional and translational regulatory information and such sequences are "operably linked" to nucleotide sequences that encode the polypeptide. An operable linkage is a linkage in which the regulatory DNA sequences and the DNA sequence sought to be expressed are connected in such a way as to permit gene sequence expression. The precise nature of the regulatory regions needed for gene sequence expression may vary from organism to organism, but shall in general include a promoter region which, in prokaryotes, contains both the promoter (that directs the initiation of RNA transcription) as well as the DNA sequences that, when transcribed into RNA, will signal the initiation of gene synthesis. Such regions will normally include those 5'-non-coding sequences involved with initiation of transcription and translation, such as the TATA box, capping sequence, CAAT sequence, and the like.

If desired, the non-coding region 3' to the gene sequence coding for the GA1 gene may be obtained by the above-described methods. This region may be retained for its transcriptional termination regulatory sequences, such as termination and polyadenylation. Thus, by retaining the 3'-region naturally contiguous to the DNA sequence coding for the GA1 gene, the transcriptional termination signals may be provided. Where the transcriptional termination signals are not satisfactorily functional in the expression host cell, then a 3' region functional in the host cell may be substituted.

Two DNA sequences (such as a promoter region sequence and the GA1 gene encoding sequence) are said to be operably linked if the nature of the linkage between the two DNA sequences does not (1) result in the introduction of a frame-shift mutation, (2) interfere with the ability of the promoter region sequence to direct the transcription of the GA1 gene sequence, or (3) interfere with the ability of the GA1 gene sequence to be transcribed by the promoter region sequence. Thus, a promoter region would be operably linked to a DNA sequence if the promoter were capable of effecting transcription of that DNA sequence.

As used herein, stringent hybridization conditions should be understood to be those conditions normally used by one of skill in the art to establish at least a 90% homology between complementary pieces of DNA or DNA and RNA. Lesser homologies, such as at least 70% homology or preferably at least 80% may also be desired and obtained by varying the hybridization conditions.

There are only three requirements for hybridization to a denatured strand of DNA to occur. (1) There must be complementary single strands in the sample. (2) The ionic strength of the solution of single-stranded DNA must be fairly high so that the bases can approach one another; operationally, this means greater than 0.2M. (3) The DNA concentration must be high enough for intermolecular collisions to occur at a reasonable frequency. The third condition only affects the rate, not whether renaturation/hybridization will occur.

Conditions routinely used by those of skill in the art are set out in readily available procedure texts, e.g., *Current Protocol in Molecular Biology*, Vol. 1, Chap. 2.10, John Wiley & Sons, Publishers (1994) or Sambrook et al., *Molecular Cloning*, Cold Spring Harbor (1989), incorporated herein by reference. As would be known by one of skill in the art, the ultimate hybridization stringency reflects both the actual hybridization conditions as well as the washing conditions following the hybridization, and ways in which to change these conditions to obtain a desired result are well known. A prehybridization solution should contain sufficient salt and nonspecific DNA to allow for hybridization to non-specific sites on the solid matrix, at the desired temperature and in the desired prehybridization time.

For example, known hybridization mixtures, such as that of Church and Gilbert, *Proc. Natl. Acad. Sci.* USA 81:1991–1995 (1984), comprising the following composition can also be used: 1% crystalline grade bovine serum albumin/1 mM EDTA/0.5M $NaHPO_4$, pH 7.2/7% SDS. Prehybridization and hybridization occurs at 65° C. Washing is done two times for 5 minutes with 2× Sodium Chloride, Sodium Citrate solution (SSC) (1× SSC is 0.15M NaCl, 0.015M Na citrate; pH 7.0) at 65° C., then two times for 30 minutes with 2× SSC and 1% SDS at 65° C., and then two times for 5 minutes at room temperature with 0.1× SSC.

Alternatively, for stringent hybridization, such prehybridization solution can contain 6× single strength citrate (SSC), 5× Denhardt's solution, 0.05% sodium pyrophosphate and 100 μg per ml of a non-specific DNA, RNA or protein, such as herring sperm DNA. An appropriate stringent hybridization mixture can then contain 6× SSC, 1× Denhardt's solution, 100 μg per ml of a non-specific DNA, RNA or protein, such as yeast tRNA and 0.05% sodium pyrophosphate.

Additional, alternative conditions for DNA-DNA analysis can entail the following:

1) prehybridization at room temperature and hybridization at 68° C.;
2) washing with 0.2× SSC/0.1% SDS at room temperature;
3) as desired, additional washes at 0.2× SSC/0.1% SDS at 42° C. (moderate-stringency wash); or
4) as desired, additional washes at 0.1× SSC/0.1% SDS at 68° C. (high stringency).

Additional, alternative but similar reaction conditions can also be found in Sambrook et al., *Molecular Cloning*, Cold Spring Harbor (1989). Formamide may also be included in prehybridization/hybridization solutions as desired.

It should be understood that these conditions are not meant to be definitive or limiting and may be adjusted as required by those of ordinary skill in the art to accomplish the desired objective.

Thus, to express the GA1 gene transcriptional and translational signals recognized by an appropriate host are necessary.

The present invention encompasses the expression of the GA1 gene protein (or a functional derivative thereof) in either prokaryotic or eukaryotic cells. Preferred prokaryotic hosts include bacteria such as *E. coli*, Bacillus, Streptomyces, Pseudomonas, Salmonella, Serratia, etc. The most preferred prokaryotic host is *E. coli*. Bacterial hosts of particular interest include *E. coli* K12 strain 294 (ATCC 31446), *E. coli* χ1776 (ATCC 31537), *E. coli* W3110 (F$^{31}$, lambda$^{31}$, prototrophic (ATCC 27325)), and other enterobacterium such as *Salmonella typhinurium* or *Serratia marcescens*, and various Pseudomonas species. Under such conditions, the GA1 gene will not be glycosylated. The procaryotic host must be compatible with the replicon and control sequences in the expression plasmid.

To express the GA1 gene (or a functional derivative thereof) in a prokaryotic cell (such as, for example, *E. coli, B. subtilis*, Pseudomonas, Streptomyces, etc.), it is necessary to operably link the GA1 gene encoding sequence to a functional prokaryotic promoter. Such promoters may be either constitutive or, more preferably, regulatable (i.e., inducible or derepressible). Examples of constitutive promoters include the int promoter of bacteriophage λ, the bla promoter of the β-lactamase gene sequence of pBR322, and the CAT promoter of the chloramphenicol acetyl transferase gene sequence of pBR325, etc. Examples of inducible prokaryotic promoters include the major right and left promoters of bacteriophage λ ($P_L$ and $P_R$), the trp, recA, lacZ, lacI, and gal promoters of *E. coli*, the α-amylase (Ulmanen, I., et al., *J. Bacteriol.* 162:176–182 (1985)) and the ζ-28-specific promoters of *B. subtilis* (Gilman, M. Z., et al., *Gene sequence* 32:11–20 (1984)), the promoters of the bacteriophages of Bacillus (Gryczan, T. J., In: *The Molecular Biology of the Bacilli*, Academic Press, Inc., N.Y. (1982)), and Streptomyces promoters (Ward, J. M., et al., *Mol. Gen. Genet.* 203:468–478 (1986)).

Prokaryotic promoters are reviewed by Glick, B. R., (*J. Ind. Microbiol.* 1:277–282 (1987)); Cenatiempo, Y. (*Biochimie* 68:505–516 (1986)); and Gottesman, S. (*Ann. Rev. Genet.* 18:415–442 (1984)).

Proper expression in a prokaryotic cell also requires the presence of a ribosome binding site upstream of the gene sequence-encoding sequence. Such ribosome binding sites are disclosed, for example, by Gold, L., et al. (*Ann. Rev. Microbiol.* 35:365–404 (1981)).

Preferred eukaryotic hosts include yeast, fungi, insect cells, mammalian cells either in vivo, or in tissue culture. Mammalian cells that can be useful as hosts include cells of fibroblast origin such as VERO or CHO-K1, or cells of lymphoid origin, such as the hybridoma SP2/0-AG14 or the myeloma P3x63Sg8, and their derivatives. Preferred mammalian host cells include SP2/0 and J558L, as well as neuroblastoma cell lines such as IMR 332 that may provide better capacities for correct post-translational processing.

For a mammalian host, several possible vector systems are available for the expression of the GA1 gene. A wide variety of transcriptional and translational regulatory sequences may be employed, depending upon the nature of the host. The transcriptional and translational regulatory signals may be derived from viral sources, such as adenovirus, bovine papilloma virus, Simian virus, or the like, where the regulatory signals are associated with a particular gene sequence which has a high level of expression. Alternatively, promoters from mammalian expression products, such as actin, collagen, myosin, etc., may be employed. Transcriptional initiation regulatory signals may be selected that allow for repression or activation, so that expression of the gene sequences can be modulated. Of interest are regulatory signals which are temperature-sensitive so that by varying the temperature, expression can be repressed or initiated, or are subject to chemical (such as metabolite) regulation.

Yeast provides substantial advantages in that it can also carry out post-translational peptide modifications. A number of recombinant DNA strategies exist that utilize strong promoter sequences and high copy number plasmids that can be utilized for production of the desired proteins in yeast. Yeast recognizes leader sequences on cloned mammalian gene sequence products and secretes peptides bearing leader sequences (i.e., pre-peptides).

Any of a series of yeast gene sequence expression systems incorporating promoter and termination elements from the actively expressed gene sequences coding for glycolytic enzymes produced in large quantities when yeast are grown in medium rich in glucose can be utilized. Known glycolytic gene sequences can also provide very efficient transcriptional control signals. For example, the promoter and terminator signals of the phosphoglycerate kinase gene sequence can be utilized.

Another preferred host is insect cells, for example the *Drosophila larvae*. Using insect cells as hosts, the Drosophila alcohol dehydrogenase promoter can be used. Rubin, G. M., *Science* 240:1453–1459 (1988). Alternatively, baculovirus vectors can be engineered to express large amounts of the GA1 gene in insects cells (Jasny, B. R., *Science* 238:1653 (1987); Miller, D. W., et al., in *Genetic Engineering* (1986), Setlow, J. K., et al., eds., Plenum, Vol. 8, pp. 277–297).

As discussed above, expression of the GA1 gene in eukaryotic hosts requires the use of eukaryotic regulatory regions. Such regions will, in general, include a promoter region sufficient to direct the initiation of RNA synthesis. Preferred eukaryotic promoters include the promoter of the mouse metallothionein I gene sequence (Hamer, D., et al., *J. Mol. Appl. Gen.* 1:273–288 (1982)); the TK promoter of Herpes virus (McKnight, S., *Cell* 31:355–365 (1982)); the SV40 early promoter (Benoist, C., et al., *Nature* (London) 290:304–310 (1981)); the yeast gal4 gene sequence promoter (Johnston, S. A., et al., *Proc. Natl. Acad. Sci.* (USA) 79:6971–6975 (1982); Silver, P. A., et al., *Proc. Natl. Acad. Sci.* (USA) 81:5951–5955 (1984)).

As is widely known, translation of eukaryotic mRNA is initiated at the codon that encodes the first methionine. For this reason, it is preferable to ensure that the linkage between a eukaryotic promoter and a DNA sequence that encodes the GA1 gene (or a functional derivative thereof) does not contain any intervening codons that are capable of encoding a methionine (i.e., AUG). The presence of such codons results either in the formation of a fusion protein (if the AUG codon is in the same reading frame as the GA1 gene encoding DNA sequence) or a frame-shift mutation (if the AUG codon is not in the same reading frame as the GA1 gene encoding sequence).

The GA1 gene encoding sequence and an operably linked promoter may be introduced into a recipient prokaryotic or eukaryotic cell either as a non-replicating DNA (or RNA) molecule, which may either be a linear molecule or, more preferably, a closed covalent circular molecule. Since such molecules are incapable of autonomous replication, the expression of the GA1 gene may occur through the transient expression of the introduced sequence. Alternatively, permanent expression may occur through the integration of the introduced sequence into the host chromosome.

In one embodiment, a vector is employed that is capable of integrating the desired gene sequences into the host cell chromosome. Cells that have stably integrated the introduced DNA into their chromosomes can be selected by also introducing one or more markers that allow for selection of host cells which contain the expression vector. The marker can provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements can also be needed for optimal synthesis of single chain binding protein mRNA. These elements can include splice signals, as well as transcription promoters, enhancers, and termination signals. cDNA expression vectors incorporating such elements include those described by Okayama, H., *Molec. Cell. Biol.* 3:280 (1983).

In a preferred embodiment, the introduced sequence is incorporated into a plasmid or viral vector capable of autonomous replication in the recipient host. Any of a wide variety of vectors can be employed for this purpose. Factors of importance in selecting a particular plasmid or viral vector include: the ease with which recipient cells that contain the vector can be recognized and selected from those recipient cells that do not contain the vector; the number of copies of the vector that are desired in a particular host; and whether it is desirable to be able to "shuttle" the vector between host cells of different species. Preferred prokaryotic vectors include plasmids such as those capable of replication in *E. coli* (such as, for example, pBR322, ColE1, pSC101, pACYC 184, πVX. Such plasmids are, for example, disclosed by Maniatis, T., et al. (In: *Molecular Cloning, A Laboratory Manual*, Cold Spring Harbor Press, Cold Spring Harbor, N.Y. (1982)). Bacillus plasmids include pC194, pC221, pT127, etc. Such plasmids are disclosed by Gryczan, T. (In: *The Molecular Biology of the Bacilli*, Academic Press, N.Y. (1982), pp. 307–329). Suitable Streptomyces plasmids include pIJ101 (Kendall, K. J., et al., *J. Bacteriol.* 169:4177–4183 (1987)), and streptomyces bacteriophages such as φC31 (Chater, K. F., et al., In: *Sixth International Symposium on Actinomycetales Biology*, Akademiai Kaido, Budapest, Hungary (1986), pp. 45–54). Pseudomonas plasmids are reviewed by John, J. F., et al. (*Rev. Infect. Dis.* 8:693–704 (1986)), and Izaki, K. (*Jpn. J. Bacteriol.* 33:729–742 (1978)).

Preferred eukaryotic plasmids include BPV, vaccinia, SV40, 2-micron circle, etc., or their derivatives. Such plasmids are well known in the art (Botstein, D., et al., *Miami Wntr. Symp.* 19:265–274 (1982); Broach, J. R., In: *The Molecular Biology of the Yeast Saccharomyces*: Life Cycle and Inheritance, Cold Spring Harbor Laboratory, Cold Spring Harbor, N.Y., p. 445–470 (1981); Broach, J. R., *Cell* 28:203–204 (1982); Bollon, D. P., et al., *J. Clin. Hematol. Oncol.* 10:39–48 (1980); Maniatis, T., In: *Cell Biology: A Comprehensive Treatise*, Vol. 3, Gene sequence Expression, Academic Press, N.Y., pp. 563–608 (1980)).

Once the vector or DNA sequence containing the construct(s) has been prepared for expression, the DNA construct(s) may be introduced into an appropriate host cell by any of a variety of suitable means: transformation, transfection, conjugation, protoplast fusion, electroporation, calcium phosphate-precipitation, direct microinjection, etc. After the introduction of the vector, recipient cells are grown in a selective medium, which selects for the growth of vector-containing cells. Expression of the cloned gene sequence(s) results in the production of the GA1 gene, or fragments thereof. This can take place in the transformed cells as such, or following the induction of these cells to differentiate (for example, by administration of bromodeoxyuracil to neuroblastoma cells or the like).

Following expression in an appropriate host, the GA1 protein can be readily isolated using standard techniques such as immunochromatography or HPLC to produce GA1 protein free of other *A. thaliana* proteins.

By employing chromosomal walking techniques, one skilled in the art can readily isolate other full length genomic copies of GA1 as well as clones containing the regulatory sequences 5' of the GA1 coding region.

As used herein, "full length genomic copies" refers to a DNA segment that contains a protein's entire coding region.

As used herein, "regulatory sequences" refers to DNA sequences that are capable of directing the transcription and/or translation of an operably linked DNA/RNA sequence. Such regulatory sequences can include, but are not limited to, a promoter, ribosome binding site, and regulatory protein binding site. One skilled in the art can readily identify certain regulatory sequences by comparing sequences found 5' to a coding region with known regulatory sequence motifs, such as those recognized by the computer programs "motif" and "consensus."

In detail, the GA1 DNA sequences disclosed herein were used to screen an *A. thaliana* genomic DNA library via chromosome walking. Genomic DNA libraries for *A. thaliana* are commercially available (Clontech Laboratories Inc, and American Type Culture Collection) or can be generated using a variety of techniques known in the art. (Sambrook et al., *Molecular Cloning: A Laboratory Manual*, Cold Spring Harbor Press (1989)). By isolating clones that overlap and occur 5' or 3' to a certain sequence, sequences hybridizing to the sequence of FIG. 6 were identified and isolated. Such sequences are contained in the vectors pGA1-4 (ATCC No. 75395) and λGA1-3.

Regulatory sequences generally occur 5' to a coding region. The preferred regulatory sequences of the present invention are those that appear from about −2 kb–0 bp 5' of the GA1 starting codon (ATG/Met). The more preferred sequences appear from about −500 bp–0 bp, the most preferred being sequences from about −250 bp–0 bp.

Using techniques known in the art and the clones described herein, it is now possible to generate functional derivatives of the GA1 gene as well as the regulatory sequence of this gene. Such derivatives allow one skilled in the art to associate a given biological activity with a specific sequence and/or structure and then design and generate derivatives with an altered biological or physical property. Such regulatory regions allow one skilled in the art to operably link non-homologous (i.e., not GA1) elements to the regulatory element functional derivative so as to provide desired hybrid structures having hybrid properties.

The preparation of functional derivatives can be achieved, for example, by site-directed mutagenesis. (Sambrook et al., *Molecular Cloning: A Laboratory Manual*, Cold Spring Harbor Press (1989)). Site-directed mutagenesis allows the production of a functional derivative through the use of a specific oligonucleotide that contains the desired mutated DNA sequence.

While the site for introducing a sequence variation is predetermined, the mutation per se need not be predetermined. For example, to optimize the performance of a mutation at a given site, random mutagenesis may be conducted at a target region and the newly generated sequences can be screened for the optimal combination of desired activity.

The functional derivatives created this way can exhibit the same qualitative biological activity as the naturally occurring sequence when operably linked to a heterologous gene. The derivative can however, differ substantially in such characteristics as to the level of induction in response to phytohormones.

One skilled in the art will recognize that the functionality of the derivative can be evaluated by routine screening assays. For example, a functional derivative made by site-directed mutagenesis can be operably linked to a reporter gene, such as β-glucuronidase (GUS), and the chimeric gene can then be quantitatively-screened for phytohormone responsiveness in chimeric or transgenic plants, or in a transient expression system.

Using a reporter gene and the GA1 regulatory elements, mutations that alter tissue specificity and strength of the GA1 promoter can be generated. By analyzing the sequence of the GA1 regulatory elements, one skilled in the art will recognize the various protein binding motifs present in the GA1 promoter, and direct mutagenesis activity to these regions.

In another embodiment of the present invention, antibodies that bind the GA1 protein are provided.

In detail, an antibody that binds to the GA1 protein can be generated in a variety of ways using techniques known in the art. Specifically, in one such method, GA1 protein purified from either an expression host or from plant tissue is used to immunize a suitable mammalian host. One skilled in the art will readily adapt known procedures in order to generate both polyclonal and monoclonal anti-GA1 antibodies. (Harlow, *Antibodies*, Cold Spring Harbor Press (1989)).

Alternatively, anti-GA1 antibodies can be generated using synthetic peptides. Using the deduced amino acid sequence encoded by the GA1 gene described herein, a synthetic peptide can be made, such that when administered to an appropriate host, antibodies will be generated which bind to the GA1 protein.

In a further embodiment of the present invention, a procedure is described for detecting the expression of the GA1 gene or the presence of the GA1 protein in a cell or tissue.

Specifically, using the antibodies and DNA sequences of the present invention, one skilled in the art can readily adapt known assay formats such as in situ hybridization, ELISA, and protein or nucleic acid blotting techniques, in order to detect the presence of RNA encoding GA1, or the GA1 protein itself. Utilizing such a detection system, it is now possible to identify the specific tissues and cells that transcribe or translate the GA1 gene.

B. Transgenic or chimeric plants containing genes whose expression mimics the GA1 gene.

In another embodiment of the invention, a method for creating a chimeric or transgenic plant is described in which the plant contains one or more exogenously supplied genes that are expressed in the same temporal and spatial manner as GA1.

In detail, a chimeric or transgenic plant is generated such that it contains an exogenously supplied expression module. The expression module comprises the regulatory elements of the GA1 gene, operably linked to a heterologous gene.

As described earlier, the regulatory region of the GA1 gene is contained in the region from about −2 kb to 0 bp, 5' to the GA1 start codon (Met). One skilled in the art can readily generate expression modules containing this region, or a fragment thereof.

Methods for linking a heterologous gene to a regulatory region and the subsequent expression of the heterologous gene in plants are well known in the art. (Weissbach et al., *Methods for Plant Molecular Biology*, Academic Press, San Diego, Calif. (1988)). One skilled in the art will readily adapt procedures for plant cell transformation, such as electroporation, Ti plasmid mediated transformation, particle acceleration, and plant regeneration to utilize the GA1 regulatory elements. In an expression module all plants from which protoplasts can be isolated and cultured to give whole regenerated plants can be transformed with the expression module of the present invention. The efficacy of expression will vary between plant species depending on the plant utilized. However, one skilled in the art can readily determine the plant varieties in which the GA1 regulatory elements will function.

In another embodiment of the present invention, a method of modulating the translation of RNA encoding GA1 in a chimeric or transgenic plant is described.

As used herein, modulation entails the enhancement or reduction of the naturally occurring levels of translation.

Specifically, the translation of GA1 encoding RNA can be reduced using the technique of antisense cloning. Antisense cloning has been demonstrated to be effective in plant systems and can be readily adapted by one of ordinary skill to utilize the GA1 gene. (Oeller et al., *Science* 254:437–439 (1991)).

In general, antisense cloning entails the generation of an expression module that encodes an RNA complementary (antisense) to the RNA encoding GA1 (sense). By expressing the antisense RNA in a cell which expresses the sense strand, hybridization between the two RNA species will occur resulting in the blocking of translation.

In another embodiment of the present invention, a method of modulating the activity of the GA1 protein is described.

Specifically, the activity of GA1 can be suppressed in a transgenic or chimeric plant by transforming a plant with an expression module which encodes an anti-GA1 antibody. The expressed antibody will bind the free GA1 and thus impair the protein's ability to function.

One skilled in the art will recognize that DNA encoding an anti-GA1 antibody can readily be obtained using techniques known in the art. In general, such DNA is obtained as cDNA, generated from mRNA that has been isolated from a hybridoma producing anti-GA1 antibodies. Methods of obtaining such a hybridoma are described earlier.

C. A system for the study of gene expression in plants

In another embodiment of the present invention, a method is described to identify the molecular interaction and the proteins responsible for the induction of the GA1 gene.

In detail, using the regulatory sequences of the GA1 gene, it is now possible to isolate the proteins that bind to these sequences.

Procedures for the isolation of regulatory factors capable of binding to a specific DNA sequence are well known in the art. One such method is affinity chromatography. DNA containing the regulatory sequence is immobilized on an appropriate matrix, such as Sepharose®, and used as an affinity matrix in chromatography (Arcangioli B., et al., *Eur. J. Biochem.* 179:359–364 (1989)).

Proteins that bind the GA1 regulatory element can be extracted from plant tissues expressing the GA1 gene. A protein extract obtained in such a fashion is applied to a column that contains immobilized GA1 regulatory region. Proteins that do not bind to the DNA sequence are washed off the column and proteins that bind to the DNA sequence are removed from the column using a salt gradient. The DNA binding protein obtained this way can be further purified using procedures such as ion exchange chromatography, high performance liquid chromatography, and size exclusion chromatography.

During the purification of the DNA binding protein, the protein can be readily assayed using a gel retardation assay (Garner, M. M. et al., *Nucl. Acid Res.* 9:3047 (1981) and Fried, M. et al., *Nucl. Acid Res.* 9:6506 (1981)).

Once the DNA binding protein has been purified, a partial amino acid sequence can be obtained from the N-terminal of the protein. Alternatively, the protein can be tryptic mapped and the amino acid sequence of one of the fragments can be determined.

Next, the deduced amino acid sequence is used to generate an oligonucleotide probe. The probe's sequence can be based on codons which are known to be more frequently used by the organism (codon preference), or, alternatively, the probe can consist of a mixture of all the possible codon combination which could encode the polypeptide (degenerate).

Such a probe can be used to screen either a cDNA or genomic library for sequences which encode the DNA binding protein. Once the gene encoding the DNA binding protein has been obtained, the sequence of the DNA encoding the binding protein can be determined, the gene can be used to obtain large amounts of the protein using an expression system, or in mutational analysis can be performed to further define the functional regions within the protein that interacts with the DNA.

Alternatively, proteins that bind to the GA1 regulatory elements can be isolated by identifying a clone expressing such a protein using the technique of Southwestern blotting (Sharp, Z. D. et al., *Biochim Biophys Acta*, 1048:306–309 (1990), Gunther, C. V. et al., *Genes Dev.* 4:667–679 (1990), and Walker, M. D. et al., *Nucleic Acids Res.* 18:1159–1166 (1990)).

In a Southwestern blot, a labeled DNA sequence is used to screen a cDNA expression library whose expressed proteins have been immobilized on a filter via colony or plaque transfer. The labeled DNA sequences will bind to colonies or plaques that express a protein capable of binding to the particular DNA sequence. Clones expressing a protein that binds to the labeled DNA sequence can be purified and the cDNA insert that encodes the DNA binding protein can be isolated and sequenced. The isolated DNA can be used to express large amounts of the protein for further purification and study, to isolate the genomic sequences corresponding to the cDNA, or to generate functional derivative of the binding protein.

D. DNA Homologous to GA1 Isolated From Other Plant Species

Using the DNA sequences isolated from *A. thaliana* thus far described, it is now possible to isolated homologous sequences from other plant varieties.

Specifically, using the GA1 DNA sequence of FIG. 6A–6B, or a fragment thereof, one skilled in the art can use routine procedures and screen either genomic or cDNA libraries from other plant varieties in order to obtain equivalent DNA sequences with significant homology to GA1. By obtaining such homologous sequences, it is now possible to study the evolution of the GA1 gene within the plant kingdom.

Additionally, by examining the differences in enzymatic activity of GA1 isolated from a variety of sources and correlation the differences with sequence divergence, it is now possible to associate specific functional variations with regions within the protein.

The invention thus far described has been directed to the GA1 gene. One skilled in the art will recognize that the procedures described herein can be used to obtain DNA encoding other enzymes responsible for GA synthesis.

Having now generally described the invention, the same will be more readily understood through reference to the following examples which are provided by way of illustration, and are not intended to be limiting of the present invention, unless specified.

EXAMPLES

Example 1

Genomic subtraction between *A. thaliana* Landsberg erecta DNA and ga1 31.89 DNA was performed as described previously (Straus and Ausubel, *Proc. Natl. Acad. Sci.* USA 87: 1889–1893 (1990)) with the following modifications.

*A. thaliana* Landsberg erecta DNA and ga1 mutant (31.89) DNA were isolated and purified by CsCl gradient centrifugation as described (Ausubel et al., in *Current Protocols in Molecular Biology*, Vol. 1 (Greene Publishing Associates/Wiley-Interscience, New York, 1990)). In the first cycle of subtraction, 0.25 $\mu$g of Landsberg erecta DNA digested with Sau3A was hybridized with 12.5 $\mu$g of the ga1 mutant 31.89 DNA that had been sheared and photobiotinylated. 10 $\mu$g of biotinylated 31.89 DNA was added in each additional cycle. Hybridizations were carried out for at least 20 hours at a concentration of 3 $\mu$g DNA/$\mu$l at 65° C. After five cycles of subtraction, the amplified products were ligated to Sau3A adaptors, amplified by PCR and ligated into the SmaI site of pUC 13.

After five cycles of subtractive hybridization, the remaining DNA fragments were enriched for sequences present in wild-type DNA but missing from 31.89 DNA. These DNA fragments were amplified by the polymerase chain reaction (PCR) and cloned. One of six clones examined (pGA1-1) contained a 250 bp Sau3A fragment that was deleted from 31.89 DNA.

1 $\mu$g HindIII-digested DNA from Landsberg erecta and ga1 alleles 31.89, 29.9, and 6.59 was fractionated on a 1% agarose gel, transferred to GeneScreen membrane (New England Nuclear), and probed with the 250 bp and 6 kb inserts in pGA1-1 and pGA1-2 (ATCC No. 75394) that had been gel-purified and labelled with $^{32}$P, FIG. 3. Hybridization conditions were the same as described in Church and Gilbert, *Proc. Natl. Acad. Sci.* USA 81:1991–1995 (1984).

Figure 3A:
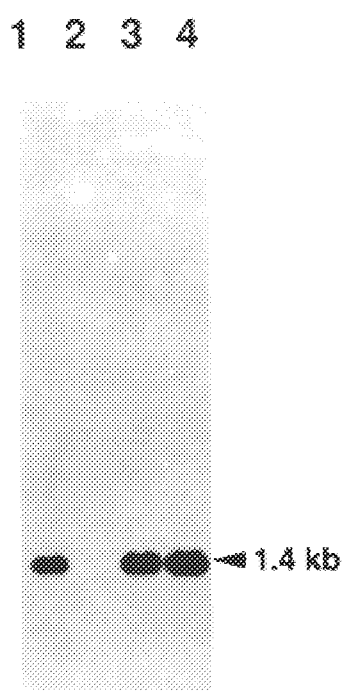
FIGS. 3A–3B. Detection of deletions and insertions in 31.89 and 6.59 DNA, respectively. Autoradiograms are shown for Southern blots probed with FIG. 3A the 250 bp Sau3A fragment from pGA1-1 (see Example 1), and FIG. 3B the 6 kb fragment from pGA1-2 (ATCC No. 75394) that covers the entire deleted region in 31.89 (FIG. 2B). Both blots A and B contain HindIII-digested DNA isolated from Landsberg erecta (lane 1), and three ga-1 mutants, 31.89 (lane 2), 29.9 (lane 3), and 6.59 (lane 4). The arrows in panel B indicate altered HindIII fragments in 31.89 (4.2 kb) and 6.59 (1.3 and 3.3 kb).

The insert in pGA1-1 hybridized to a 1.4 kb HindIII fragment in DNA samples isolated from wild-type Landsberg erecta and from the ga1 mutants 29.9 and 6.59 but did not hybridize to 31.89 DNA (FIG. 3A).

To determine the extent of the deletion in 31.89 DNA identified by pGA1-1, pGA1-1 DNA was used as a hybridization probe to isolate larger genomic fragments corresponding to the deletion in 31.89. These cloned fragments are shown in FIG. 2B.

λGA1-3 was isolated from a Landsberg erecta genomic library constructed in λFIX (Voytas et al., *Genetics* 126:713–721 (1990)) using $^{32}$P-labelled pGA1-1 as probe. pGA1-2 (ATCC No. 75394) was obtained by ligating a 6 kb SalI-EcoRI fragment from λGA1-3 into the XhoI and EcoRI sites of pBluescriptII SK (Stratagene). pGA1-4 (ATCC No. 75395) was isolated from a genomic library of *A. thaliana* ecotype Columbia DNA constructed in the binary vector pOCA18 (Olszewski et al., *Nucl. Acid Res.* 16:10765–10782 (1988)) which contains the T-DNA borders required for efficient transfer of cloned DNA into plant genomes (Olszewski et al., *Nucl. Acid Res.* 16:10765–10782 (1988)).

Figure 3B:
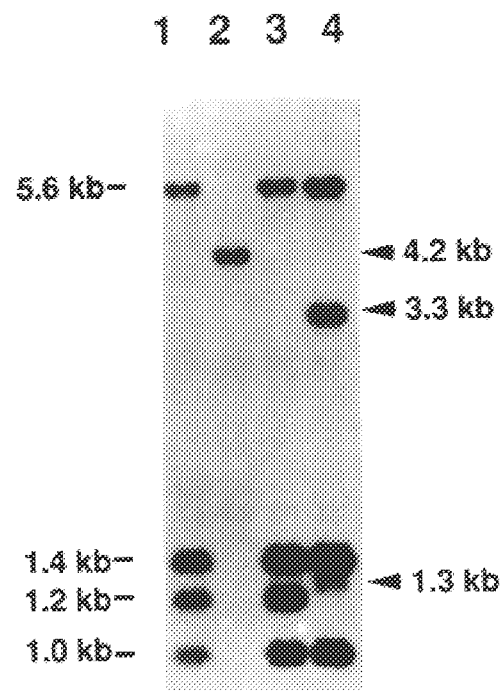

Plasmid pGA1-2 (ATCC No. 75394) containing a 6 kb fragment spanning the insert in pGA1-1 (FIG. 2B), was used to probe a Southern blot containing HindIII-digested DNA from wild-type *A. thaliana* and from several ga1 mutants. As shown in FIGS. 3B and 4B, pGA1-2 (ATCC No. 75394) hybridized to four HindIII fragments (1.0 kb, 1.2 kb, 1.4 kb and 5.6 kb) in wild-type DNA that were absent in DNA from 31.89 mutants. The deletion mutation produces an extra HindIII fragment (4.2 kb) in 31.89 DNA. These results and additional restriction mapping (not shown) showed that the deletion in 31.89 DNA is 5 kb, corresponding to 0.005% of the *A. thaliana* genome (5 kb/$10^5$ kb) (See FIG. 2B).

Three lines of evidence indicate that the characterized 5.0 kb deletion in mutant 31.89 corresponds to the GA1 locus. First, RFLP mapping analysis carried out by the procedure detailed in Nam, H. G. et al. *Plant Cell* 1:699–705 (1989), using λGA1-3 (FIG. 2B) as a hybridization probe showed that λGA1-3 maps to the telomere proximal region at the top of chromosome 4, consistent with the location to which the GA1 locus had been mapped previously by Koornneef et al. (*J. Hered.* 74:265–272 (1983)).

Figure 4A:
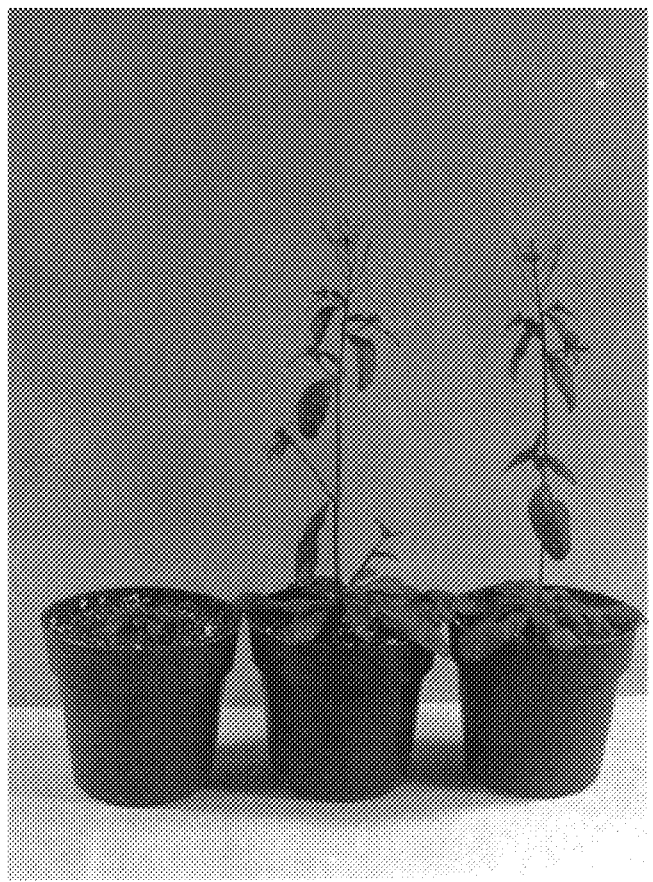
FIGS. 4A–4C. Photograph and Southern blots of wild-type and transgenic plants containing GA1 gene.
Figure 4B:
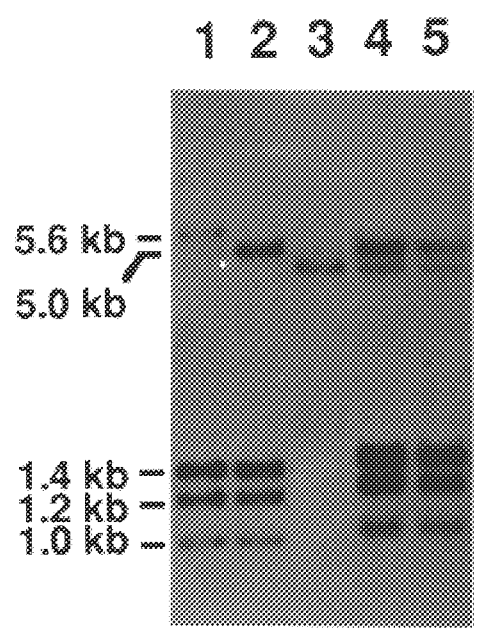

Second, a cosmid clone pGA1-4 (ATCC No. 75395) (FIG. 2B), which contains a 20 kb insert of wild-type (Columbia) DNA spanning the deletion in 31.89, complemented the ga-1 mutation in 31.89 as determined by the phenotype of *Agrobacterium tumefaciens*-mediated transformants (FIG. 4A).

The amino acid sequence of FIG. 8 (SEQ ID NO: 4), the partial cDNA sequence of FIGS. 6 and 7 (SEQ ID NOS: 1–2) and the full length cDNA sequence of FIG. 9 (SEQ ID NO: 3) are encoded by the cosmid clone pGA1-4 (ATCC No.75395). The sequence on the cosmid clone additionally contains DNA encoding GA1 introns.

*Agrobacterium tumefaciens* strain LBA4404 containing pGA1-4 was used to infect root explants of ga1 mutant 31.89 and kanamycin-resistant (Km$^r$) transgenic plants were selected as described (Valvekens et al., *Proc. Natl. Acad. Sci.* USA 85:5536–5540 (1988)). 130 Km$^r$ plants were regenerated that set seeds in the absence of exogenous GA (T1 generation). 50 to 300 seeds from each of 4 different T1 plants showed 100% linkage of the ga1 and Km$^r$ phenotypes that segregated approximately 3:1 to the ga1/Km$^s$ phenotype (T2 generation).

Seeds of transgenic ga1 and wild-type plants were germinated on agarose plates containing 1× Murashige & Skoog salts and 2% sucrose with or without kanamycin (MS plates). Seeds of the ga1 mutant 31.89 were soaked in 100 μM GA$_3$ for 4 days before being germinated on MS plates. Seven-day-old seedlings were transferred to soil.

To show the dwarf phenotype, no additional GA$_3$ was given to the mutant 31.89 after germination. Southern blot analyses were carried out as described for FIG. 3A–3B. The insert in pGA1-4 (ATCC No. 75395) was isolated from the Columbia ecotype. As seen in lanes 1 and 2 in FIG. 4B, pGA1-2 (ATCC No. 75394) detected an RFLP between the Landsberg (5.6 kb) and Columbia (5.0 kb) DNAs. The DNA in lanes 1, 2, and 3 in panel B was purified by CsCl density gradient centrifugation whereas the DNA in lanes 4 and 5 in FIG. 4B was purified by a miniprep procedure. This explains the minor differences in mobilities of the hybridizing bands in lanes 1, 2, and 3 compared to lanes 4 and 5.

Several independent T2 generation transgenic plants, containing the insert of pGA1-4 (ATCC No. 75395) integrated in the 31.89 genome, did not require exogenous GA for normal growth. Germination, stem elongation, and seed set were the same in the transgenic plants as in the wild-type plants without exogenous GA treatment. Southern blot analysis, using the 6 kb fragment from pGA 1-2 (ATCC No. 75394) as a probe, indicated that both the endogenous ga1 31.89 locus (4.2 kb) and wild-type GA1 DNA (5.0, 1.4, 1.2 and 1.0 kb HindIII fragments) were present in two independent T3 generation transgenic plants (FIG. 4B).

Figure 4C:
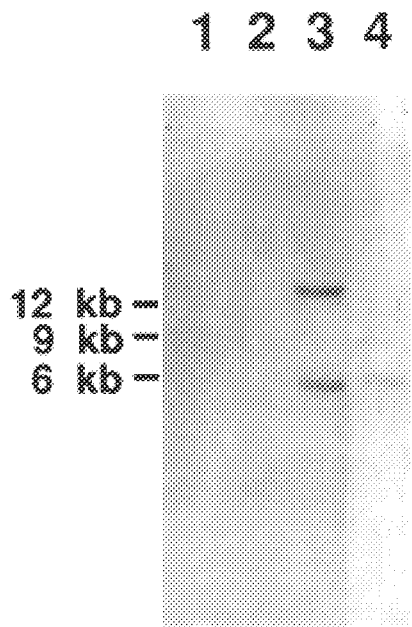

Further Southern blot analysis, using the vector pOCA18 which contains the T-DNA border sequences as a probe, showed that only two border fragments were present in the genomes of both transgenic plants (FIG. 4C). These results indicated that the wild-type GA1 DNA was integrated at a single locus in the genomes of both transgenic plants.

Third, to obtain unequivocal evidence that the 5.0 kb deletion in 31.89 corresponds to the GA1 locus, we showed that four additional ga1 alleles contain alterations from the wild-type sequence within the region deleted in 31.89 in the order predicted by the genetic map. To aid in this analysis, a partial GA1 cDNA clone (0.9 kb) (Sequence in FIG. 6A–6B (SEQ ID NO: 1), containing poly A and corresponding to the 1.2 kb HindIII fragment (FIG. 2B), was isolated from a cDNA library constructed from RNA isolated from siliques (seed pods) of *A. thaliana* ecotype Columbia. Four exons and three introns in the 1.2 kb HindIII fragment were deduced by comparison of the cDNA and genomic DNA sequences (FIG. 2B, sequence data not shown). The identification of this cDNA clone showed that the 1.2 kb HindIII fragment is located at the 3' end of the GA1 gene and suggested that the mutations in the ga1 alleles 31.89, Bo27, 6.59, d352, and A428 should also be located at the 3' end of the GA1 gene.

In addition to the 31.89 allele, two other ga1 alleles, 6.59 and 29.9, were induced by fast neutron mutagenesis (Koornneef et al., *Genet. Res. Camb.* 41:57–68 (1983)). As shown in FIG. 3B, the 1.2 kb HindIII fragment in 6.59 DNA was replaced by two new fragments of 1.3 kb and 3.3 kb without alteration of the adjacent 1.4 kb and 5.6 kb fragments. Further Southern blot analysis and direct DNA sequencing of PCR products from 6.59 DNA templates indicated that the 6.59 allele contains a 3.4 kb or larger insertion in the 1.2 kb HindIII fragment in the last intron defined by the cDNA clone (FIG. 2B). Southern blot analyses, using pGA1-2 (ATCC No. 75394) (FIG. 2B) and pGA1-4 (ATCC No. 75395) as probes, showed that there are no visible deletions or insertions in 29.9 DNA. Three additional ga1 alleles, A428, d352 and Bo27, are located at or near the 6.59 allele on the genetic map (FIG. 2A). Direct sequencing of PCR products amplified from Bo27, A428, and d352 mutant DNA templates revealed single nucleotide changes within the last two exons in the 1.2 kb HindIII fragment in all three mutants (FIG. 2B). Mutant Bo27, which defines one side of the genetic map, contained a single nucleotide change in the most distal GA1 exon. The single nucleotide changes in mutants Bo27, A428, and d352 result in missense mutations, consistent with the leaky phenotypes of mutants A428 and d352 (Koornneef et al., *Genet. Res. Camb.* 41:57–68 (1983)). It is unlikely that the base changes observed in mutants Bo27, A428, and d352 are PCR artifacts or are due to the highly polymorphic nature of the GA1 locus because the 1.2 kb HindIII fragment amplified and sequenced from mutants NG4 and NG5 both had the wild-type sequence. Moreover, the PCR products were sequenced directly and the sequence analysis was carried out twice using the products of two independent amplifications for each allele examined.

We used the recombination frequency between different ga1 alleles reported by Koornneef et al. (*Genet. Res. Camb.* 41:57–68 (1983)) to calculate that the recombination frequency per base pair was approximately $10^{-5}$ cM within the GA1 locus. This calculation was based on the reported recombination frequency of $0.5 \times 10^2$ cM between ga1 alleles A428 or d352 and Bo27 (FIG. 2A) and our observation that the mutations in d352 and Bo27 and in A428 and Bo27 are separated by 432 and 427 bp, respectively. This calculation suggested that the extent of the entire GA1 locus defined by mutants 29.9 and Bo27 was approximately 7 kb. The predicted size of this locus can accommodate the 2.8 kb mRNA detected in wild-type plants using the GA1 cDNA as a hybridization probe (FIG. 5).

Poly(A)$^+$RNA of four-week-old and five-week-old plants was prepared from the entire plant except the roots and silique RNA was prepared from immature siliques plus some flower buds and stems as previously described (Ausubel et al., in *Current Protocols in Molecular Biology*, Vol. 1 (Greene Publishing Associates/Wiley-Interscience, New York, 1990); Maniatis et al., in *Molecular Cloning: A Laboratory Manual*, 197–201 (Cold Spring Harbor Laboratory, Cold Spring Harbor, N.Y., 1982)). Approximately 2 micrograms of RNA of each sample was size-fractionated on a 1% agarose gel (Maniatis et al., in *Molecular Cloning: A Laboratory Manual*, 197–201 (Cold Spring Harbor Laboratory, Cold Spring Harbor, N.Y., 1982)), transferred to GeneScreen membrane, and hybridized with a $^{32}$P-labelled 0.9 kb EcoRI DNA fragment from the GA1 cDNA (FIG. 5). The RNA blot was also hybridized with a $^{32}$P-labelled 1.65 kb EcoRI fragment containing the *A. thaliana* cab gene (AB 165) (Leutwiler et al., *Nucl. Acid Res.* 14:4051–4064 (1986)). Decreased hybridization of the cab probe in lane 3 reflects the fact that the cab gene is not highly expressed in siliques.

Figure 5:
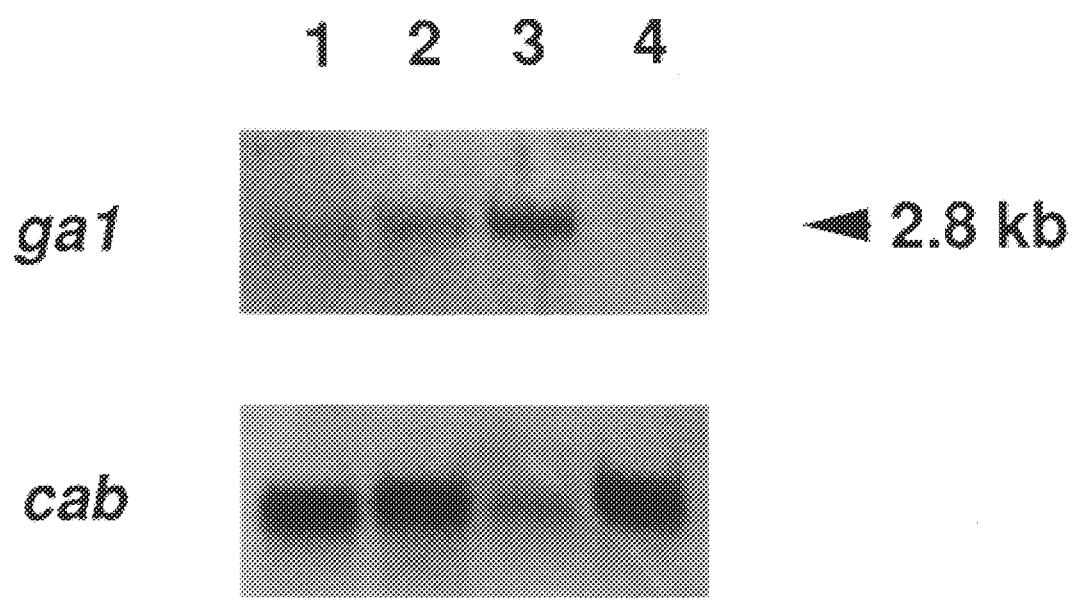
FIG. 5. Detection of a 2.8 kb mRNA using GA1 cDNA probes. Autoradiogram of an RNA blot probed with a $^{32}$P-labelled 0.9 kb GA1 cDNA or cab cDNA (chlorophyll a/b-binding protein gene). RNA was from wild type four-week-old plants (lane 1), five-week-old wild type plants, (lane 2), immature wild-type siliques (lane 3), and four week-old ga-1 mutant 31.89 plants (lane 4).

As expected, the 2.8 kb RNA could not be detected in the deletion mutant (FIG. 5). The linkage map of *A. thaliana* is approximately 600 cM and the genome size is approximately $1.08 \times 10^8$ bp (Goodman et at., unpublished results). This is equivalent to approximately $6 \times 10^{-6}$ cM per base pair, in good agreement with the observed recombination frequency in the GA1 locus.

Cloning the *A. thaliana* GA1 gene presented a variety of experimental opportunities to investigate the regulation and the site of GA biosynthesis. Because ent-kaurene is the first committed intermediate in GA biosynthesis, it is likely that the GA1 gene, required for the formation of ent-kaurene, is a point of regulation for GA biosynthesis (Graebe, J. E., *Ann. Rev. Plant Physiol.* 38:419–465 (1987); Moore, T. C., in *Biochemistry and Physiology of Plant Hormones*, 113–135 (Springer-Verlag, New York, 1989)). Indeed, the biosynthesis of ent-kaurene has been shown to occur preferentially in rapidly developing tissues, such as immature seeds, shoot tips, petioles, and stipules near the young elongating internodes (Moore, T. C., in *Biochemistry and Physiology of Plant Hormones*, 113–135 (Springer-Verlag, New York, 1989); Chung and Coolbaugh, *Plant Physiol.* 80:544–548 (1986)).

Genomic subtraction is not labor intensive and the results reported here indicate that genomic subtraction could be routinely used to clone other non-essential *A. thaliana* genes. All that is needed is a method for generating deletions at high frequency. In addition to the ga1 deletion in mutant 31.89 induced by fast neutron mutagenesis (Koornneef et al., *Genet. Res. Camb.* 41:57–68 (1983); Dellaert, L. W. M., "X-ray- and Fast Neutron-Induced Mutations in *Arabidopsis thaliana*, and the Effect of Dithiothreitol upon the Mutant Spectrum," Ph.D. thesis, Wageningen (1980); Koornneef et al., *Mutation Research* 93:109–123 (1982)), X-ray- and γ-ray- irradiation have also been shown to induce short viable deletions in *A. thaliana* at the chl-3 (Wilkinson and Crawford, *Plant Cell* 3:461–471 (1991)), tt-3 (B. Shirley and H. M. Goodman, unpublished result) and gl-1 loci (D. Marks, *Mol. General Genetics* 241: 586–594 (1993)).

Example 2

EXPRESSION OF ANTISENSE GA1 RNA

An expression vector is constructed as previously described such that it expresses an RNA complementary to the sense strand GA1 RNA. The antisense GA1 RNA is expressed in a constitutive fashion using promoters that are constitutively expressed in a given host plant, for example, the cauliflower mosaic virus 35S promoter. Alternatively, the antisense RNA is expressed in a tissue specific fashion using tissue specific promoters. As described earlier, such promoters are well known in the art.

In one example, the antisense construct pPO35 (Oeller et al., *Science* 254:437–439 (1991)) is cut with BamH1 and SAC1 to remove the tACC2 cDNA sequence. After removing the tACC2 cDNA, the vector is treated with the Klenow fragment of *E. coli* DNA polymerase I to fill in the ends, and the sequence described in FIG. 6A–6B (SEQ ID NO: 1) is blunt end ligated into the vector such that the strand operably linked to the promoter is that which transcribes the GA1 antisense RNA sequence. The ligated vector is used to transform an appropriate *E. coli* strain.

Colonies containing the ligated vector are screened using colony hybridization or Southern blotting to obtain vectors which contain the GA1 cDNA in the orientation which will produce antisense RNA when transcribed from the 35S promoter contained in the vector.

The antisense GA1 vector is isolated from a colony identified as having the proper orientation and the DNA is introduced into plant cells by one of the techniques described earlier, for example, electroporation or Agrobacterium/Ti plasmid mediated transformation.

Plants regenerated from the transformed cells express antisense GA1 RNA. The expressed antisense GA1 RNA binds to sense strand GA1 RNA and thus prevent translation.

Example 3

FULL LENGTH cDNA AND PROTEIN SEQUENCE OF THE *A. THALIANA* GA1 GENE

Using the above described and following techniques, a cDNA clone was constructed that contained the complete cDNA sequence of GA1 (pGA1-29). The GA1 sequences in this clone were determined and compared to that of the genomic sequence of cosmid clone pGA1-4. FIG. 9A–9C shows the complete cDNA sequence of the GA1 protein (obtained from clone pGA1-41, which is derived from pGA1-29) (SEQ ID NO: 3). The location of introns was determined by comparing the sequence of the genomic clone and a cDNA clone (pGA1-29). The inverted arrows over the sequences are the intron junctions. Mutations that have been identified (for example ga1-6 C to T and ga1-8 C to A) are designated by name and base change above the corresponding base in the native sequence shown. The location of ga1-4, ga1-7 and ga1-9 DNA are also designated.

The complete amino acid sequence of the GA1 protein was determined from the cDNA sequence and is shown in FIG. 8 (SEQ ID NO: 4).

Example 4

CHARACTERIZATION OF THE GA1 GENE

A. Isolation of the 2.6 kb GA1 cDNA Clone

The 2.6 kb cDNA clone, pGA1-29, was isolated by screening a cDNA library, constructed from RNA isolated from green siliques of *Arabidopsis thaliana* ecotype Columbia (Giraudat et al., *Plant Cell* 4:1251–1261 (1992)) using $^{32}$P-labeled 0.9 kb GA1 cDNA (Sun et al., *Plant Cell* 4:119–128 (1992), pGA1-24) as the hybridization probe.

B. Plasmid Construction

The DNA sequence around the first ATG codon of the GA1 gene was modified to contain either an AflIII site or an NcoI site by PCR. Conversion to the AflIII site did not change the coding sequence. The introduction of the NcoI site at the ATG codon created a single base change in the second codon (TCT to GCT; Ser to Ala). The PCR-amplified 0.5 kb AflIII-SphI and NcoI-SphI DNA fragments were cloned into the AflIII-SphI sites of pUC19 (pGA1-41) and NcoI (converted from HindIII site)-SphI sites of pUC18 (pGA1-32). The cloned PCR fragments were sequenced to ensure that no mutations were introduced during amplification. The rest of the coding sequence for the full-length GA1 protein was excised from pGA1-29 by SphI and EcoRI (blunt-ended by Klenow enzyme) and ligated to SphI and HincII sites of pGA1-41 to create the full-length GA1 cDNA with an AflIII site at the initiation codon. The entire coding region of the GA1 cDNA was excised by AflIII and BamHI as a 2.5 kb DNA and inserted into NcoI and BamHI sites of the pET-8c vector (Studier et al., *Methods Enzymol.* 185: 60–89 (1990)). The resulting plasmid, which contained 2.5 kb GA1 cDNA under control of T7 promoter by translational fusion, was named pGA1-43. This plasmid was used to express full-length GA1 protein in *E. coli* cells. The rest of the coding sequence in the 0.9 kb cDNA was excised from pGA1-24 by SphI and BamHI and ligated to SphI and BamHI sites of pGA1-32. The 0.9 kb coding sequence was excised by NcoI and BamHI and was cloned into pET-8c vector. This plasmid was named pGA1-40 and was used to express a 30 kD truncated GA1 protein in *E. coli* cells.

The 2.5 kb AflIII-BamHI GA1 cDNA was fused to CaMV-35S promoter with dual enhancer and 5'-untranslated region from tobacco etch virus by the following procedure. A 1.2 kb HindIII cassette containing CaMV-35S promoter with dual enhancer, TEV-NTR, and CaMV 35S polyA signal was excised from pRTL2 (Restrepo et al., *Plant Cell* 2:987–998 (1990)) and ligated to the HindIII site of pSK vector. The 2.5 kb AflIII-BamHI cDNA was inserted into NcoI-BamHI sites of the above plasmid so that the GA1 cDNA was in a sense orientation behind the CaMV-35S promoter and the TEV-NTR leader sequence (pGA1-48). A 2.6 kb EcoRI-BamHI fragment carrying TEV-NTR-GA1 DNA was excised from pGA1-48 and incubated with T4 DNA polymerase to create blunt ends. This DNA was then ligated into HincII site of pSP64 (polyA) (Promega) in order to generate GA1 transcripts with polyA tail in vitro using SP6 RNA polymerase (pGA1-84). A 4 kb SmaI-SalI fragment of pGA1-48 containing the CaMV 35S-TEV-NTR-GA1 gene fusion was inserted into the SmaI-SalI sites of the binary vector pBIN19 (Bevan, M., *Nucl. Acids Res.* 12:8711–8721 (1984)) and the resulting plasmid was named pGA1-49.

The 2.6 kb cDNA in pGA1-29 is located in the EcoRI site of pSK and is in an antisense orientation behind the T7 promoter. This plasmid was cut with EcoRI, religated and screened for plasmids with inserts in opposite orientation. The resulting plasmid was named pGA1-30. A 2.6 kb GA1 cDNA was excised from pGA1-29 and -30 by XbaI and KpnI restriction enzymes and inserted into XbaI and KpnI sites located between the CaMV 35S promoter and the nos terminator in pBIN19-35S. The vector pBIN19-35S was a gift from Dr. Mark Conkling and was created by inserting a nos terminator into pWPF126 (Fitzmaurice et al., *Plant Mol. Biol.* 20:177–198 (1992)). The resulting plasmids were named pGA1-45 (sense orientation), and pGA1-47 (antisense).

C. DNA Sequencing Analysis of Wild-Type and Mutant GA1 DNA

DNA sequences of GA1 genomic DNA and cDNA were obtained using the dideoxy method (Ausubel et al., *Current Protocols in Molecular Biology*, Green Publ. Assoc./Wiley-Interscience, 1990) with Sequenase (U.S. Biochemical Corp.) and both single- and double-stranded DNA templates. The 1.4 kb HindIII DNA in the ga1-9 mutant was amplified by polymerase chain reaction (PCR), reamplified by asymmetric PCR and the single-stranded DNA templates were sequenced directly (Innis et al., PCR *Protocols: A Guide to Methods and Applications*, Academic Press, San Diego, 1990). 1.4 kb DNA fragments spanning intron 12 to exon 15 were amplified from genomic DNA isolated from ga1-1 and ga1-4 by PCR. These PCR-amplified DNA fragments were cloned into the SmaI site of the pSK vector, and DNA sequences were obtained by using double-stranded DNA templates isolated from several independent clones.

Figure 10:
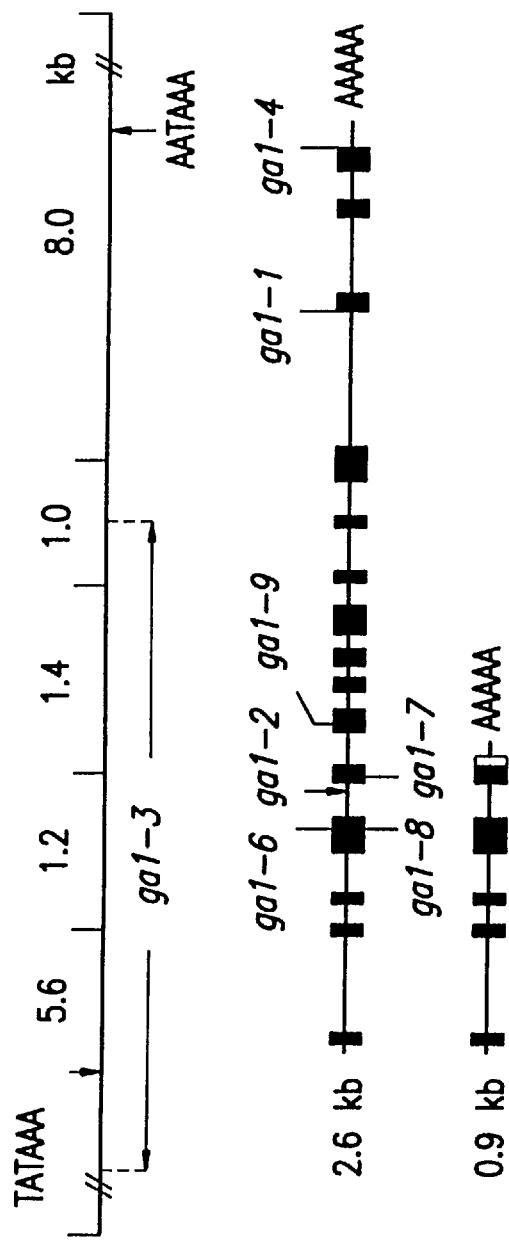
FIG. 10. Physical map of the GA1 locus. The top horizontal line shows the HindIII restriction map and the heavy line indicates the coding region of the GA1 gene. The putative TATA box (TATAAA) and the polyA signal (AATAAA) are labeled by arrows. The location of the 5 kb deletion in the ga1-3 mutant is indicated by two arrows. The diagrams below the restriction map depict the introns (lines) and exons (shaded boxes) derived from two cDNA clones (2.6 kb and 0.9 kb) of the GA1 gene. The 5th exon of the 0.9 kb cDNA extended an additional 48 nucleotides (open box). The positions of mutations in ga1-2 (inversion or insertion), ga1-4 (14-bp deletion), and ga1-1, 6, 7, 8, 9 (point mutations) are indicated along the diagram for the 2.6 kb cDNA.

The genomic DNA clones (10–20 kb) and a partial cDNA clone (0.9 kb) corresponding to the Arabidopsis GA1 locus were previously isolated (Sun et al., *Plant Cell* 4:119–128 (1992)). One additional GA1 cDNA clone of 2.6 kb was obtained by screening 5×10$^5$ cDNA clones from a silique library of the Arabidopsis ecotype Columbia. DNA sequence analyses of the cDNA clones and the GA1 genomic clones were carried out to characterize the complete structure of the GA1 locus (FIGS. 9A–9C and 10). The 2.6 kb cDNA is nearly-full length as we previously determined the GA1 mRNA to be 2.8 kb (Sun et al., *Plant Cell* 4:119–128, 1992). The ATG codon at position 48–50 of the 2.6 kb cDNA is believed to be the translational start site for the GA1 protein because it is the first ATG codon, is followed by a long open reading frame of 2406 bps and a polyA tail (FIG. 9A–9C) (SEQ ID NO: 3), and this clone encodes a 86 kD protein, which as discussed below, is the initial size of the GA1 protein. The 2.4 kb open reading frame spans approximately 7 kb of the genomic DNA and contains 15 exons and 14 introns (FIG. 10). All introns contain 5'-GT and 3'-AG splice-junction consensus sequences. There is a putative TATA box (TATAAACA) located at nucleotides −287 to −280 upstream from the presumptive translational start codon, and tandem repeats of polyadenylation signal (AATAAA) at nucleotides 117 to 128 downstream from the translational stop codon.

Additionally, Southern blot analysis using a partial GA1 cDNA (the 0.9 kb fragment of FIG. 10) as a probe under low stringency hybridization conditions (hybridization and wash at 52° C. in the same buffer) shows an additional DNA fragment that is present in both wild-type Arabidopsis ecotype Landsberg erecta and in the gal1-3 mutant. This gene could encode either a GA1 homologue or another related terpene cyclase.

Koornneef et al., *Genet. Res., Camb.* 41:57–68 (1983) constructed a fine-structure genetic map of the GA1 locus using nine ga1 alleles, which were subsequently renamed in Sun et al., *Plant Cell* 4:119–128 (1992). Table 1 and FIGS. 9 and 10 summarize the nature and position of eight of the nine ga1 mutations. Five of the mutations, ga1-2 (inversion or insertion), ga1-3 (5 kb deletion), and ga1-6, 7, 8 (point mutations), were placed on the physical map as described previously (Sun et al., *Plant Cell* 4:119–128 1992). Mutant ga1-7, which defines one side of the genetic map, contained a point mutation in the most distal exon (exon 5) in the 0.9 kb cDNA (FIG. 10). However, isolation of the 2.6 kb cDNA revealed that the 0.9 kb cDNA likely resulted from either a cloning artifact or a premature termination of transcription in intron 6. PCR and DNA sequencing analyses were carried out to determine the positions of 3 additional ga1 alleles, ga1-1, 4, 9. Two of these alleles, ga1-1 and 4, define the other side of the GA1 genetic map, while ga1-9 is located at the middle of the genetic map and overlapped with the ga1-3 deletion mutation. Sequence analysis showed that ga1-4 contains a small deletion of 14 nucleotides in the last exon (exon 15, FIGS. 9 and 10). ga1-1 and ga1-9 contain single-base changes at the 3' splice junction in intron 12 (AG to A A) and in exon 6 (TGG to TAG, amber codon), respectively. Mutations in all three alleles are located downstream from the coding sequences defined by the 0.9 kb cDNA (FIG. 10). The results indicate that the 0.9 kb cDNA does not encode a functional GA1 protein.

TABLE 1

The Nature and Position of Mutations in Various ga1 Mutants

| Mutant | Nature of Mutation | Position in Coding Sequence | Position in Genomic Sequence |
|---|---|---|---|
| gal-1 | AG → AA 3' splice junction | | intron 12 |
| gal-2 | ≧3.4 kb insertion or inversion | | intron 4 |
| gal-3 | 5 kb deletion | ~1 kb 5'-upstream of ATG to 1621 | ~1 kb 5'-upstream of ATG to exon 11 |
| gal-4 | 14 nucleotide deletion | 2375–2388 | exon 15 |
| gal-6 | TCT → TTT Ser Phe | 452 | exon 4 |
| gal-7 | GAA → AAA Glu Lys | 631 | exon 5 |
| gal-8 | GGA → AGA Gly Arg | 457 | exon 4 |
| gal-9 | TGG → TAG Trp stop | 818 | exon 6 |

The position of various ga1 mutations (Table 1 and FIG. 10) corresponds well to their locations on the genetic map (Koornneef et al., *Genet. Res., Camb.* 41:57–68 (1983)); with an exception that the ga1-7 mutation is located between ga1-2 and ga1-9 on our physical map in contrast to being at one end of the genetic map. Using the recombination frequency between ga1-6, 7, and 8, we previously estimated the recombination frequency within the GA1 locus to be ~$10^{-5}$ cM per nucleotide (Sun et al., *Plant Cell* 4:119–128 (1992)). We examined this value using ga1-6, ga1-9 and ga1-4 and the recombination frequency within the GA1 locus is ~$1.2 \times 10^{-5}$ cM per nucleotide. This is in good agreement with the average recombination frequency of the Arabidopsis genome (~$5.2 \times 10^{-5}$ cM per nucleotide, Hauge et al., *Plant J.* 3:745–754 (1993)).

Example 5

COMPLEMENTATION ANALYSIS

To test if the 2.4 kb open reading frame of the GA1 cDNA encodes a functional protein in Arabidopsis, we expressed the GA1 cDNA in ga1-3 deletion mutant plants. The 2.6 kb GA1 cDNA was fused transcriptionally to CaMV-35S promoter in both sense (pGA1-45) and antisense (pGA1-47) orientations in the binary vector pBIN19. To maximize the expression of the GA1 cDNA, the 2.4 kb coding sequence was also fused translationally to CaMV-35S promoter with duplicated enhancer and 5'-nontranslated regions from tobacco etch virus (TEV-NTR). TEV-NTR has been shown to enhance efficiency of translation in vivo and in vitro (Carrington and Freed, *J. Virol.* 64:1590–1597, 1990).

The DNA cassette containing the CaMV-35S-TEV-NTR-GA1 gene fusion was inserted into the binary vector pBIN19 and the resulting plasmid was named pGA1-49. Gene fusions in plasmids pGA1-45, 47, and 49 were each transferred into the ga1-3 genome via *Agrobacterium tumefaciens*-mediated transformation. Several (3, 7, and 8 for pGA1-45, 47 and 49, respectively) independent kanamycin-resistant (Km$^r$) transgenic plants (T1 generation) were regenerated. All T1 plants derived from the sense GA1 constructs, pGA 1-45 and pGA 1-49, set seeds in the absence of exogenous GA. Seeds (ranging from thirty to four hundred) from each T1 transgenic line showed 100% linkage of the GA1$^+$and Km$^r$ phenotypes, most of which (all pGA1-45 lines and seven of the pGA1-49 lines) segregated approximately 3:1 in relation to the GA$^-$/kanamycin-sensitive (Km$^s$) phenotype (T2 generation). All T2 generation GA1$^+$/Km$^r$ transgenic plants grew and set seeds without exogenous GA treatment. This result indicated that the 2.4 kb open reading frame encodes an active GA1 protein which complemented the ga1-3 mutation in these transgenic plants. Seven Km$^r$T1 plants derived from the control pGA1-47 (antisense GA1) were regenerated. Similar to the phenotype of the original ga1-3 plants, these transgenic plants all required exogenous GA$_3$ treatment for vegetative growth, flowering and seed set.

Example 6

FUNCTIONAL ANALYSIS OF THE GA1 PROTEIN

Figure 11:
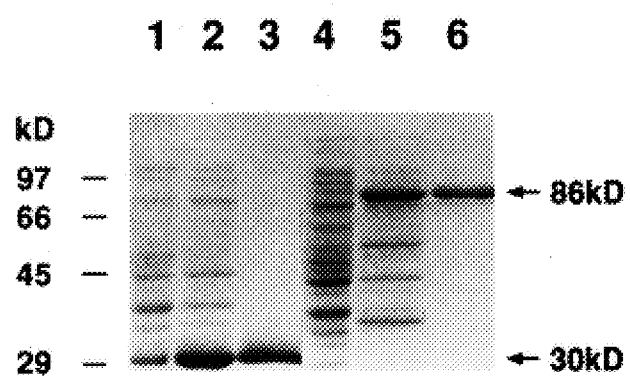
FIG. 11. Over-expression of the Arabidopsis GA1 gene in *E. coli* using the T7 RNA polymerase expression system. Lanes 1 and 4 contain uninduced (− IPTG) crude extracts and lanes 2 and 5 contain induced (+ IPTG) inclusion body fractions from cells carrying the 0.9 kb and the 2.6 kb GA1 cDNAs, respectively. Lanes 3 and 6 contain gel-purified GA1 proteins of 30 kD (truncated) and 86 kD, respectively.

In order to study the function of the GA1 protein, the full-length (2.6 kb) and truncated (0.9 kb) GA1 cDNAs were over-expressed in *E. coli*. FIG. 3 shows that the 2.6 kb cDNA in pGA1-43 encodes the full-length GA1 protein of 86 kD (lane 2) and the 0.9 kb cDNA in pGA1-40 produces a truncated GA1 protein of 30 kD (lane 5). Both the 30 kD protein and the 86 kD protein were purified from *E. coli* extracts by isolation of inclusion bodies (Marston, *DNA Cloning: A Practical Approach*, IRL Press, Oxford England, 1987), followed by SDS-polyacrylamide gel electrophoresis, and electroelution. The gel-purified proteins were detected as single bands on SDS-polyacrylamide gel by Coomassie Blue staining (FIG. 11, lanes 3 and 6). The 30 kD protein was further examined by N-group analysis and was shown to have the six amino acid sequence at the N-terminus that were predicted by the cDNA sequence. Whereas the N-terminus of the 86 kD protein was blocked. Antibodies to the 30 kD and the 86 kD GA1 proteins were obtained by immunization of rabbits with the gel-purified proteins.

Figure 12:
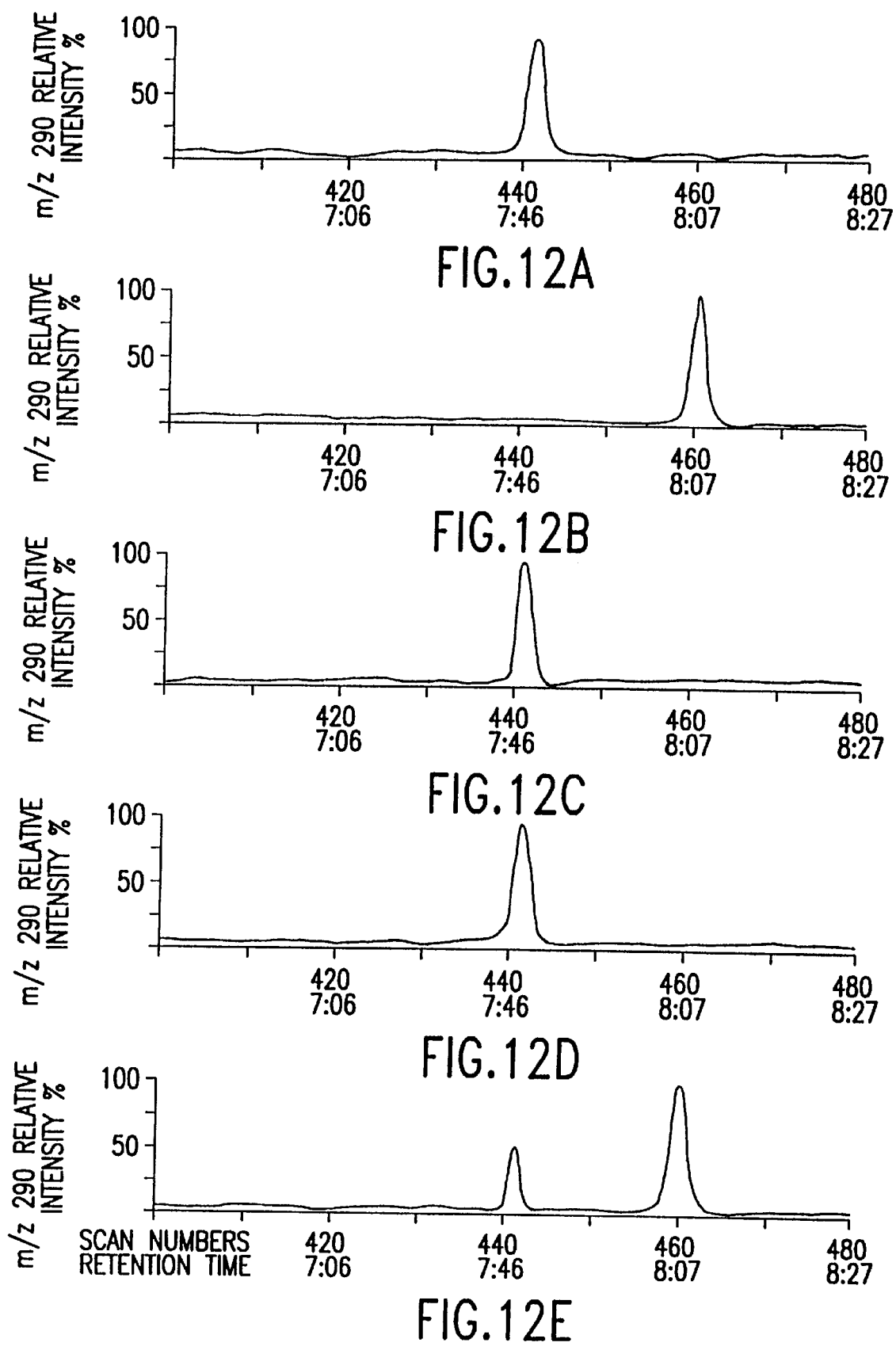
FIG. 12A–12E. GC-MS identification of GGol and copalol from hydrolyzed methanol extracts of *E. coli*.

Sandmann and Misawa, *FEMS Micro. Lett.* 90:253–258 (1992) demonstrated that the crtE gene of *Erwinia uredovora* encodes GGPP synthase which catalyzes the conversion of farnesyl pyrophosphate to GGPP. *E. coli* cells harboring the crtE gene accumulate large amount of GGPP (Sandmann and Misawa, *FEMS Micro. Lett.* 90:253–258 (1992)). This is in contrast to normal *E. coli* cells which only produce trace amounts of GGPP. A plasmid pACCRT-E, which contains the crtE gene, was co-transformed with either the control plasmid pGA1-40 (0.9 kb GA1 cDNA) or pGA1-43 (2.6 kb GA1 cDNA) into *E. coli* cells. GGPP and CPP were extracted from cells carrying pACCRT-E alone, pACCRT-E and pGA1-40, or pACCRT-E and pGA1-43 and the hydrolyzed extracts were analyzed using gas chromatography/mass spectrometry (GC/MS). The products were identified by full-scan GC/MS. FIGS. 12A–12E shows the pattern of the mass chromatography at m/z 290 which is the size of the molecular ions of geranylgeraniol (GGol) and copalol. The extracts from cells haboring only pACCRT-E or both pACCRT-E and pGA1-40 contained high levels of GGol, but did not have any detectible copalol (FIGS. 12C and D). In contrast, copalol was accumulated to a quite high level in cells carrying both PACCRT-E and pGA1-43 and consequently producing both GGPP synthase and the 86 kD GA1 protein (FIG. 4E). These results indicate that the 86 kD protein encoded by the 2.4 kb open reading frame in GA1 cDNA is the enzyme, ent-kaurene synthetase A, which catalyzes the conversion of GGPP to CPP. The truncated 30 kD GA1 protein does not have this enzyme activity.

Example 7

GA1 PROTEIN LEVEL IN WILD-TYPE AND TRANSGENIC LINES CONTAINING VARIOUS GENE FUSIONS

A. *Agrobacterium tumefaciens*-Mediated Transformation of Arabidopsis Root Explants The transformation procedure was as described previously (Valvekens et al., 1988) with slight modifications (Sun et al., *Plant Cell* 4:119–128 (1992)). pGA1-45, 47 and 49 were introduced into Agrobacterium LBA4404 by electroporation (Ausubel et al., Current Protocols in Molecular Biology (New York: Green Publishing Associates/Wiley-Interscience) (1990). Stability of the insert of the plasmid in LBA4404 was tested by restriction digestion and gel electrophoresis of plasmid DNA purified by NaOH/SDS mini-preparation procedure (Ausubel et al., Current Protocols in Molecular Biology (New York: Green Publishing Associates/Wiley-Interscience) (1990).

A fresh overnight culture of LBA4404 carrying individual plasmids was used to infect root explants of four-week-old ga1-3 mutants. Km$^r$ transgenic plants were regenerated as described (Valvekens et al., *Proc. Natl. Acad. Sci. USA* 85:5536–5540 (1988)). Seeds of transgenic plants were germinated on MS agar plates containing kanamycin (50 µg/ml). Non-germinating seeds after 8 days were transferred onto MS plates containing 100 µM GA$_3$ and 50 µg/ml kanamycin to score for GA$^+$/Km$^r$ and GA$^-$/Km$^s$ segregation.

Figure 13:
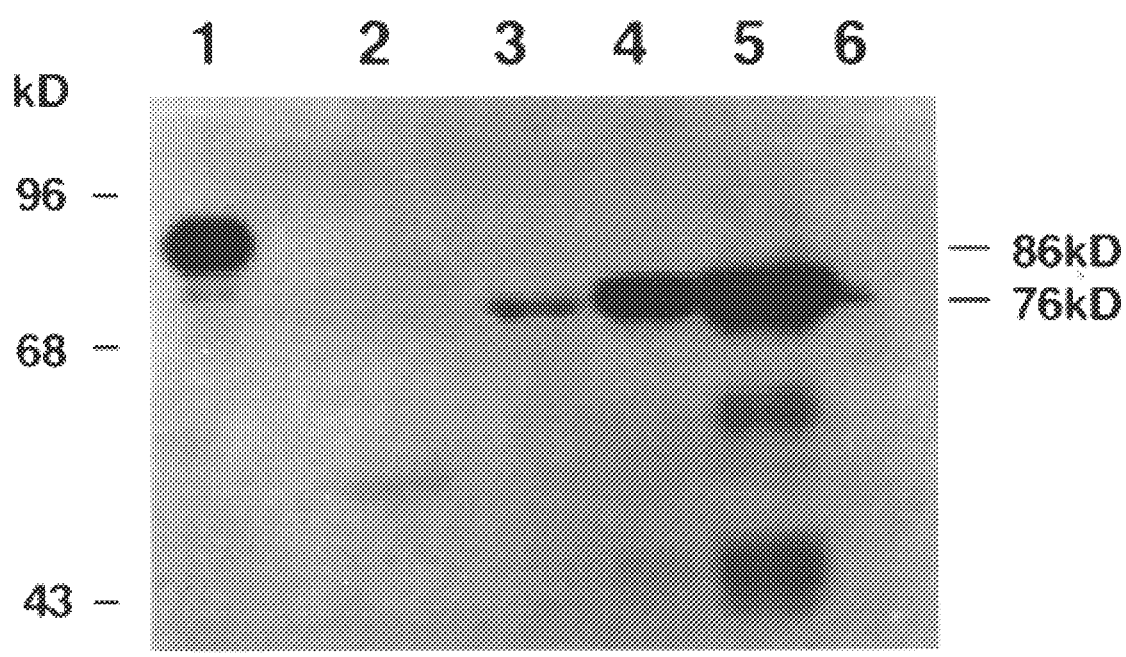
FIG. 13. Immunoblot analysis of GA1 protein levels in soluble protein fractions from Arabidopsis using GA1 antisera. Protein extracts from 2-week-old Arabidopsis seedlings were fractionated by centrifugation at 100,000 g, and the supernatant fraction was separated on an 8% SDS-PAGE gel. Protein gel blot was incubated with 30 kD GA1 antisera and peroxidase-conjugated goat anti-rabbit antisera, and detected using ECL reagent followed by autoradiography. The blot contains 15 ng of gel-purified 86 kD protein produced from *E. coli* carrying pGA1-43 (lane 1); 50 mg of the 100,000 g supernatant fractions from transgenic plants containing CaMV 35S promoter-antisense GA1 (lane 2); CaMV 35S promoter-GA1 (lane 3); CaMV 35S-TEV-NTR-GA1 (lanes 4 and 5); Landsberg erecta (lane 6).

The levels of GA1 proteins in both sense and antisense transgenic Arabidopsis plants were compared to the level in wild-type plants (ecotype Landsberg erecta) by immunoblot analysis (FIG. 13). Supernatant fractions, which contained most of the ent-kaurene synthetase activity, were obtained by tissue extraction and centrifugation (Bensen and Zeevaart, *J. Plant Growth Regul.* 9:237–242 (1990)). A major protein band of 76 kD was labeled by the GA1 antibodies in three over-expression lines tested (FIG. 13, lanes 3, 4, and 5). This protein accumulated at higher levels in the plants containing CaMV-35S-TEV-NTR-GA1 construct (lanes 4 and 5) than in the plants carrying CaMV-35S-GA1. This protein is absent in lanes 2 and 6, which contain proteins extracted from an antisense transgenic line and wild-type plants, respectively. The sensitivity of this analysis could detect as low as about 1 ng of the gel-purified 86 kD GA1 protein produced in *E. coli*. Since the endogenous GA1 gene is expressed at extremely low levels (Sun et al., *Plant Cell* 4:119–128 (1992)), it is not surprising that the GA1 antibodies could not detect the endogenous GA1 protein in wild-type plants.

In addition, one can examine the pattern of expression of the endogenous GA1 gene using a promoter-glucuronidase (GUS) gene fusion. The data from this analysis is used to design plant organ-specific promoters and cDNA gene fusions in order to manipulate the GA biosynthesis in specific plant organs.

Immunoblot Analyses

Proteins from 2-week-old Arabidopsis seedlings were extracted and fractionated by centrifugation at 10,000 g for 10 min and then at 100,000 g for 90 min at 4° C. (Bensen and Zeevaart, *J. Plant Growth Regul.* 9:237–242, 1990). The 100,000 g supernatant fractions (50 mg each) were loaded on an 8% SDS-PAGE gel, electrophoresed and transferred to a GeneScreen membrane (Du Pont-New England Nuclear). Immunoblot analysis was carried out as described (Sambrook et al. *Molecular Cloning: A Laboratory Manual*, Cold Spring Harbor Press, Cold Spring Harbor, N.Y. 1989). The membrane was incubated with 1000-fold diluted 30 kD GA1 antisera (primary antibody), then with 2500-fold diluted peroxidase-conjugated goat anti-rabbit antisera (secondary antibody, Sigma), and detected using the enhanced chemiluminescence reagent (ECL, Amersham) followed by autoradiography.

Example 8

OVER-EXPRESSION OF GA1 PROTEINS IN *E. COLI* AND THE PROCEDURE FOR GENERATING GA1 ANTIBODIES

The pGA1-40 and pGA1-43 constructs were transformed into DE3 lysogenic *E. coli* strain BL21(DE3) (Studier et al., *Methods Enzymol.* 185:60–89 (1990). The expression of the GA1 cDNA was induced by the addition of 0.4 mM isopropyl-β-D-thiogalactopyranoside (IPTG) at absorbance (600 nm)=0.8 with 2 hour incubation at 37° C. Thirty ml of cell cultures was harvested by centrifugation, washed and resuspended in 10 ml of 50 mM Tris (pH 8.0), 2 mM EDTA. The cells were sonicated on ice with a Branson microtip at a setting of 4, with four 20-sec pulses. The sonicate was mixed with 1% Triton X-100, incubated on ice for 5 min and then centrifuged at 12000 g for 10 min at 4° C. to isolate inclusion bodies (Marston, *DNA Cloning: A Practical Approach*, Oxford England: IRL Press, 1987, with slight modification).

The 30 kD and the 86 kD GA1 proteins were purified from the inclusion body fraction of *E. coli* extracts by SDS-polyacrylamide gel electrophoresis, and electroelution with the Electro-separation system (Schleicher & Schuell). The purified proteins were detected as single bands on SDS-polyacrylamide gels by Coomassie Blue staining. Rabbit antibodies to either the 30 kD or the 86 kD GA1 proteins were obtained by subcutaneous injection of gel-purified proteins in complete Freund's adjuvant (Harlow and Lane, *Antibodies: A Laboratory Manual*, Cold Spring Harbor, N.Y., Cold Spring Harbor Laboratory, 1988). For N-group analysis, proteins were fractionated by SDS-polyacrylamide gel electrophoresis and then transferred to Immobilon membrane (Millipore) in Tris-Glycine and 10% methanol. The membrane was first stained with Ponceau S, destained in deionized water and the 30 kD and 86 kD protein bands were excised for N-group analysis.

Example 9

CO-EXPRESSION OF GA1 cDNA AND GGPP SYNTHASE GENE IN *E. COLI* CELLS

For detection of the accumulation of CPP, pGA1-43 and pACCRT-E containing 2.5 kb GA1 cDNA and the GGPP synthase gene, CrtE, respectively, were co-transformed into *E. coli* strain HMS174 (DE3). As a control, pGA1-40 containing the truncated GA1 cDNA and pACCRT-E plasmids were also co-transformed into HMS174 (DE3). For each 200 ml culture, 4 ml of fresh overnight culture was inoculated into 200 ml LB broth with 30 μg/ml of chloramphenicol and 100 μg/ml of ampicillin, and incubated at 37° C. with vigorous shaking. When the absorbance (600 nm) reached 0.9, 200 μl of 0.1M IPTG was added and the culture was incubated at 37° C. for 1 hour further. The cells were pelleted by centrifugation, washed with 100 ml of 10 mM Tris (pH 8.0), 0.1M NaCl, 1 mM EDTA (pH 8.0), and freeze-dried.

A. Extraction of GGPP and CPP from *E. coli* Cells

Freeze-dried cells were resuspended in 1 ml $H_2O$ and extracted three times with 2 ml methanol at 0°C. After centrifugation, the clear methanol-water extracts were concentrated under reduced pressure by rotary evaporation at 30° C. A small amount of water was added to the concentrated solution and concentrated again to remove any remaining methanol from aqueous solution. The final residue was diluted in 2 ml of 25 mM $Na_2CO_3$ and extracted three times with 1 ml of hexane. The resulting aqueous phase was collected for GC/MS analysis.

B. Hydrolysis of Pyrophosphate Solution and Analysis of Geranylgeraniol and Copalol by GC/MS Analysis One fifth of the pyrophosphate solution was hydrolyzed with 18 units of bacterial alkaline phosphatase (Takara, Japan) in 100 mM Tris-HCl, pH 9.0 and 2 mM $MgCl_2$ at 30° C. for 15 hours, followed by three hexane extractions. The pooled hexane extracts were concentrated by gentle $N_2$ flow and dissolved in 200 μl hexane and 1 μl of this sample was analyzed by full-scan GC/MS. GC/MS was performed with a Finnigan MAT INCOS 50 mass spectrometer coupled to an HP-5890A gas chromatograph (Finnigan MAT) equipped with a capillary column (DB-1, 0.32 mm idx30 m, J & W Scientific Inc. USA) as described (Saito et al., *Plant Cell Physiol.* 32:239–245, 1991). Experiments were repeated twice. Authentic geranylgeraniol and copalol were gifts from Dr. T. Takigawa (Kurare Central Research Institute) and Dr. T. Nakano (Venezuela Science Institute), respectively.

Example 10

SEQUENCE COMPARISON WITH OTHER TERPENE CYCLASES

The BLAST network service (Altschul et al., *J. Mol. Biol.* 215:403–410 (1990)) at the National Center for Biotechnology and the FastA and BestFit GCG programs were used to search for sequence homology between the peptides. The sequence alignment was generated by using the PileUp and LineUp in the GCG program.

Comparison of the predicted GA1 amino acid sequence (802 amino acids) with sequences in the GenBank Database revealed that stretches of 124 amino acids (328–451) and 165 amino acids (334–498) in the GA1 protein (SEQ ID NO: 8) share sequence similarities of 72% (36% identity) and 72% (32% identity) with that of tobacco sesquiterpene cyclase (SEQ ID NO: 5) (Facchini and Chappell, *Proc. Natl. Acad. Sci.* USA 89:11088–11092 (1992)) and a monoterpene cyclase, spearmint limonene synthase (SEQ ID NO: 7) (Colby et al., *J. Biol. Chem.* 268:23016–23024 (1993)), respectively. A diterpene cyclase, castor bean casbene synthase (SEQ ID NO: 6) (Colby et al., *J. Biol. Chem.* 268:23016–23024 (1993)) also has a sequence similarity of 72% (30% identity) with a stretch of 182 amino acids (329–510) in the GA1 protein. FIG. 15 (SEQ ID NOS: 5–9) shows alignment of the predicted GA1 sequence (327–604) to partial peptide sequences of these three terpene cyclases. The sequence DDXXD, which was proposed to function in binding the divalent metal ion-pyrophosphate complex of the prenyl substrate (Ashby et al., *Molecular Biology of Atherosclerosis*, Elsevier Science Publishers B. V., Amsterdam, 1990) as absent in the GA1 protein sequence. This sequence is highly conserved among the other three terpene cyclases and several other prenyltransferases (Facchini and Chappell, *Proc. Natl. Acad. Sci.* USA 89:11088–11092 (1992); Jennings et al., *Proc. Natl. Acad. Sci.* USA 88:6038–6042 (1991)). These enzymes all catalyze the condensation reaction of allylic pyrophosphates to produce cyclized terpenes or higher prenyl pyrophosphates. In contrast, GA1 catalyzes the cyclization reaction without removal of the pyrophosphate group. An alternative aspartate-rich motif, DXDDTA was identified at residues 377–382 in the GA1 sequence. This sequence is also found in squalene-hopene cyclases isolated from *Zymomonas mobilis* (GenBank/EMBL no. X73561) and *Bacillus acidocaldarius* (Ochs et al., 1992). These enzymes catalyze the direct cyclization of a triterpene, squalene, to form hopanoids; the substrate squalene does not contain pyrophosphate. The common catalytic property between these enzymes and the GA1 protein is the ring-closure reaction of terpenoid compounds. Although the squalene-hopene cyclases do not have large regions of sequence similarity with the GA1 protein, the DXDDTA motif may be involved in the catalytic activity of these enzymes.

Example 11

IMPORT OF IN VITRO SYNTHESIZED GA1 PROTEIN INTO INTACT PEA CHLOROPLASTS

Plasmid pGA1-84, which contains TEV-NTR-GA1 cDNA, was linearized by incubating with EcoRI enzyme and used as a template for in vitro transcription in the presence of diguanosine triphosphate (Pharmacia) and SP6 RNA polymerase (New England BioLab; Krainer et al., *Cell* 36: 993–1005 (1984)). The resulting 5'-capped GA1 transcripts were translated in vitro using a Promega rabbit reticulocyte translation system with $^{35}$S-labeled methionine/cysteine (ICN) according to the Promega manual. The translation mixture was centrifuged at 100,000 g for 15 min at 4° C. The post-ribosomal supernatant was used for import experiments. Protein import into intact pea chloroplasts was carried out as described (Grossman et al., *J. Biol. Chem.* 257: 1558–1563 (1982)) with slight modification (Kohorn et al., *J. Cell Biol.* 102: 972–981 (1986)). After incubation with isolated pea chloroplasts, 200 μg/ml of protease type X (thermolysin, Sigma) was added to degrade proteins not sequestered by the intact chloroplasts. Triton X-100 (0.1%) was added to one tenth of the sample during thermolysin treatment. Intact chloroplasts were repurified by centrifugation through 35% Percoll before analyzing on SDS-polyacrylamide gels, followed by autoradiography.

Figure 14:
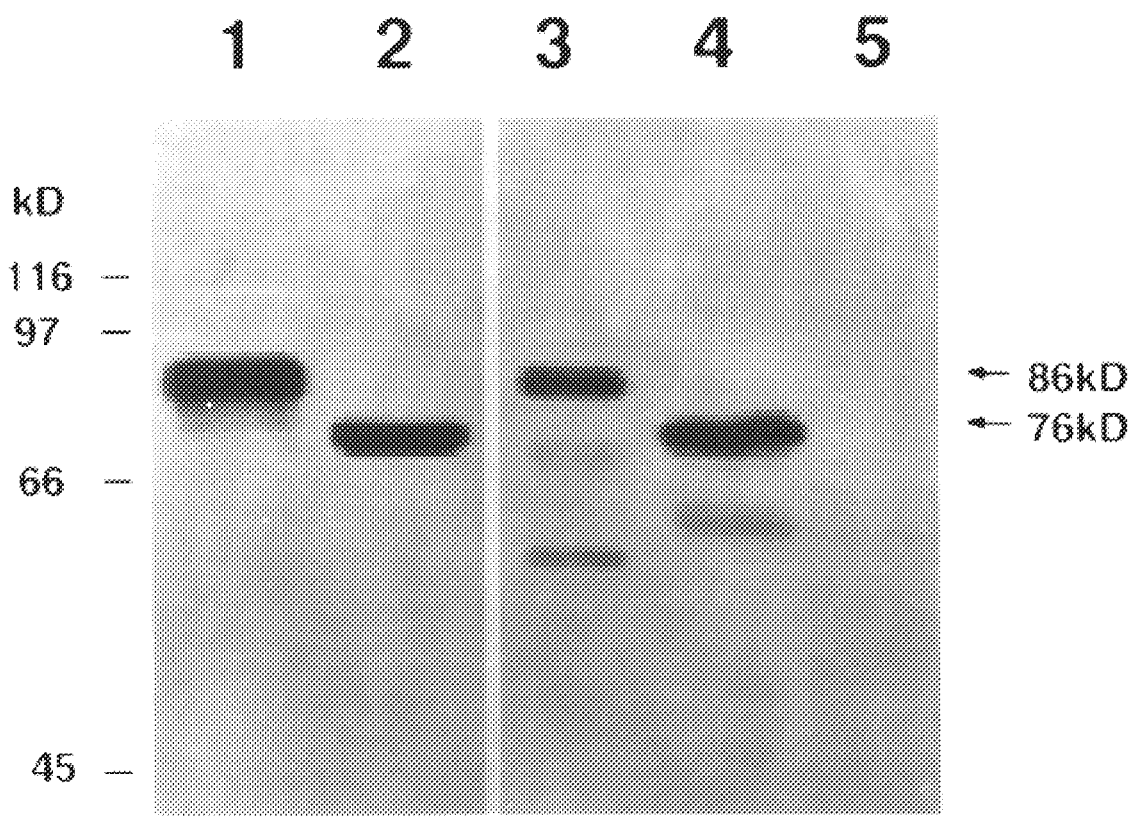
FIG. 14. Import of GA1 protein into isolated pea chloroplasts. Lanes 1 and 2 are a immunoblot of 10 ng of gel-purified 86 kD protein produced by *E. coli* carrying pGA1-43 and 15 mg of the 100,000 g supernatant fraction from an *Arabidopsis transgenic* line carrying the CaMV 35S-TEV-NTR-GA1 gene fusion, respectively. Lanes 3–5 are from a fluorogram of $^{35}$S-labeled GA1 protein subjected to different treatments. Lane 3 is an aliquot of the total in vitro translated products containing $^{35}$S-labeled GA1 protein. Lanes 4 and 5 are the labeled protein sample after uptake by isolated intact pea chloroplasts, followed by protease treatment in the absence or presence of 0.1% Triton X-100, respectively.

Immunoblot and in vitro protein import experiments show that the GA1 protein can be translocated into and processed in the chloroplasts. The first 50 N-terminal amino acids of the GA1 protein are rich in serine (26%) and threonine (12%) with an estimated pI of 10.2. These properties are common features of the transit peptides of many chloroplast proteins (Keegstra et al., *Ann. Rev. Plant Physiol. Plant Mol. Biol.* 40: 471–501 (1989)). A $^{35}$S-methionine/cysteine-labeled GA1 protein of 86 kD was synthesized in vitro using SP6 RNA polymerase and a rabbit reticulocyte translation system (FIG. 14, lane 3). The size of this in vitro translated protein is the same as that expressed in *E. coli* cells (FIG. 14, lane 1). When the 86 kD in vitro translated product was incubated with isolated pea chloroplasts, it was processed to a smaller, 76 kD protein that was protected from digestion by externally added protease (FIG. 6, lane 4). This protein was degraded by the protease when chloroplasts were disrupted by 0.1% Triton X-100 (FIG. 14, lane 5). Immunoblot analysis showed that the GA1 protein produced by the GA1 cDNA in transgenic plants migrated as a 76 kD protein (FIG. 14, lane 2). These results suggest that the GA1 proteins are targeted to and processed in chloroplasts in planta.

Example 12

Modulating the Translation of RNA Encoding GA1 Protein

The translation of RNA encoding GA1 protein in a plant is modulated by generating an expression vector providing for transcription of antisense GA1 RNA from an operably linked promoter. The plant is then transfected with the expression vector encoding the antisense GA1 RNA vector.

Example 13

Cloning DNA Encoding GA1 Protein

A DNA molecule encoding the GA1 protein is cloned by hybridizing a desired DNA molecule to the sequences or antisense sequences of FIG. 9 or fragments thereof, under stringent hybridization conditions. Those DNA molecules hybridizing to the probe sequences are selected and transformed into a host cell. The transformants that express GA1 are selected and cloned.

Example 14

Hybridization Conditions for Cloning DNA Encoding GA1 Protein

Hybridization conditions for the cloning of the DNA encoding GA1 protein are as follows:
1) prehybridizing at 65° C. for 1 hour;
2) hybridizing overnight at 65° C. in the hybridization buffer;
3) washing two times for 5 minutes in 2× SSC at 65° C., then two times for 30 minutes in 2× SSC and 1.0% SDS at 65° C.; and
4) washing two times for 5 minutes at room temperature in 0.1× SSC.

Example 15

Molecular Weight Markers

The GA1 protein produced recombinantly is purified by routine methods in the art (*Current Protocol in Molecular Biology*, Vol. 2, Chap. 10, John Wiley & Sons, Publishers (1994)). Because, the deduced amino acid sequence is known, the molecular weight of this protein can be precisely determined and the protein can be used as a molecular weight marker for gel electrophoresis. The calculated molecular weight of the GA1 protein based on the deduced nucleic acid sequence is about 93 kDa.

CONCLUSION

All references mentioned herein are incorporated by reference in the disclosure.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A DNA purified molecule comprising the DNA encoding the amino acid sequence of the GA1 (SEQ ID NO: 4) protein of *Arabidopsis thaliana*.

2. The DNA molecule of claim 1, wherein the gene encoding said GA1 protein comprises the GA1 DNA sequence of pGA1-29 or the DNA sequence shown on FIGS. 9A–9C (SEQ ID NO: 3).

3. A DNA purified molecule consisting of DNA encoding the amino acid sequence of FIG. 8 (SEQ ID NO: 4).

4. A vector containing the sequences of any one of claims 1–3.

5. A non-*Arabidopsis thaliana* host transformed with one of the vectors of claim 4.

6. The host of claim 5, wherein said host is selected from the group consisting of a bacteria cell, a yeast cell or a plant cell.

7. The host of claim 6, wherein said host is a plant cell.

8. The host of claim 7, wherein said plant cell is a dicotyledonous plant cell.

9. A plant regenerated from the plant cell of claim 8.

10. Progeny of the plant of claim 9.

11. A propagule of the plant of claim 10.

12. A seed produced by the progeny of claim 11.

13. A method for expressing GA1 protein, wherein said method comprises:
   1) transforming a host with the DNA molecule of any one of claims 1–3 operably linked to a promoter;
   2) expressing said GA1 protein from said DNA in said transformed host cell.

14. A method of modulating the translation of RNA encoding GA1 in a plant comprising the steps of:
   1) generating an expression vector encoding antisense GA1 RNA;
   2) transfecting said plant with said expression vector (1).

15. An isolated DNA molecule wherein said molecule consists essentially of a nucleic acid sequence, and wherein said nucleic acid sequence:
   1) encodes a GA1 polypeptide, and
   2) hybridizes to the sense or antisense sequence of the DNA of FIG. 9 (SEQ ID NO: 3) or fragments thereof, when hybridization is performed under stringent hybridization conditions.

16. An isolated DNA molecule encoding a GA1 protein, said DNA molecule prepared by a process comprising:
   1) hybridizing a desired DNA molecule to the sense or antisense sequence of FIGS. 9A–9C (SEQ ID NO: 3) or fragments thereof, wherein the hybridization is performed under stringent hybridization conditions;
   2) selecting those DNA molecules of said population that hybridize to said sequence; and
   3) selecting DNA molecules of part (2) that encode said GA1 protein.

17. An isolated DNA molecule encoding a GA1 protein as claimed in claims 15 or 16, said DNA molecule prepared by a process comprising:
   1) prehybridizing for 1 hour at 65° C.;
   2) hybridizing overnight at 65° C. in the hybridization buffer;
   3) washing two times for 5 minutes in 2× SSC at 65° C., then two times for 30 minutes in 2× SSC and 1.0% SDS at 65° C.; and
   4) washing two times for 5 minutes at room temperature in 0.1× SSC.

18. An *Arabidopsis thaliana* host transformed with one of the vectors of claim 4, wherein the expression of the transformed GA1 gene results in overexpression of the GA1 protein compared to the wild-type *Arabidopsis thaliana*.

19. The host of claim 18, wherein said host is a plant cell.

20. The plant generated from the plant cell of claim 19.

21. Progeny of the plant of claim 20.

22. A propagule of the plant of claim 21.

23. A seed produced by the progeny of claim 22.

24. A purified DNA molecule comprising the DNA sequence of FIGS. 6A–6B (SEQ. ID. No. 1) or the DNA sequence of FIGS. 7A–7B (SEQ. ID. No. 2).

25. A vector containing a sequence of claim 24.

26. A non *Arabidopsis thaliana* host transformed with the vector of claim 25.

27. The host of claim 26, wherein said host is selected from the group consisting of a bacteria cell, a yeast cell and a plant cell.

28. The host of claim 27, wherein said host is a plant cell.

29. The host of claim 28, wherein said plant cell is a dicotyledonous plant cell.

30. A plant regenerated from the plant cell of claim 29.

31. Progeny of the plant of claim 30.

32. A propagule of the plant of claim 31.

33. A seed produced by the progeny of claim 32.

34. A method for expressing a protein, wherein said method comprises:
   1) transforming a host with a DNA molecule of claim 24 operably linked to a promoter;
   2) expressing said protein from said DNA in a transformed host cell.

35. An *Arabidopsis thaliana* plant transformed with the DNA of claim 24 wherein the expression of said DNA results in overexpression of the GA1 protein compared to the wild-type *Arabidopsis thaliana*.

* * * * *